(12) United States Patent
Kim

(10) Patent No.: US 10,973,913 B2
(45) Date of Patent: Apr. 13, 2021

(54) JAK INHIBITORS AND USES THEREOF

(71) Applicant: Brian Kim, St. Louis, MO (US)

(72) Inventor: Brian Kim, St. Louis, MO (US)

(73) Assignee: Washington University, St. Louis, MO (US)

( * ) Notice: Subject to any disclaimer, the term of this patent is extended or adjusted under 35 U.S.C. 154(b) by 238 days.

(21) Appl. No.: 15/998,614

(22) PCT Filed: Feb. 16, 2017

(86) PCT No.: PCT/US2017/018097
§ 371 (c)(1),
(2) Date: Aug. 16, 2018

(87) PCT Pub. No.: WO2017/143014
PCT Pub. Date: Aug. 24, 2017

(65) Prior Publication Data
US 2020/0282051 A1    Sep. 10, 2020

Related U.S. Application Data

(60) Provisional application No. 62/295,875, filed on Feb. 16, 2016.

(51) Int. Cl.
*A61K 31/519*    (2006.01)
*A61K 39/395*    (2006.01)
*A61P 17/04*    (2006.01)

(52) U.S. Cl.
CPC ........ *A61K 39/3955* (2013.01); *A61K 31/519* (2013.01); *A61P 17/04* (2018.01)

(58) Field of Classification Search
CPC ............................ A61K 31/519; C07D 487/04
USPC ...................................... 514/265.1; 544/280
See application file for complete search history.

(56) References Cited

U.S. PATENT DOCUMENTS

2015/0126535 A1    5/2015    Gonzales et al.
2015/0246048 A1    9/2015    Brown et al.

FOREIGN PATENT DOCUMENTS

WO    WO 2015/042596 A1    3/2015

OTHER PUBLICATIONS

Agarwal et al. (2004)—Conditional Gene Deletion in Primary Nociceptive Neurons of Trigeminal Ganglia and Dorsal Root Ganglia, Genesis, pp. 122-129, vol. 38, No. 3.
Amon, Wolff (1994). Healing of chronic atopic dermatitis lesions in skin areas of paraplegia after trauma. Journal of Dermatology, pp. 982-983, vol. 21.
Artis, Spits (2015)—The biology of innate lymphoid cells, Nature, pp. 293-301, vol. 517, No. 7534.
Azimi et al. (2015)—Altered manifestations of skin disease at sites affected by neurological deficit, British Journal of Dermatology, pp. 988-993, vol. 172, No. 4.
Bautista et al. (2014)—Why we scratch an itch: The molecules, cells and circuits of itch, Nature Neuroscience, pp. 175-182, vol. 17, No. 2.
Beck et al. (2014)—Dupilumab Treatment in Adults with Moderate-to-Severe Atopic Dermatitis, New England Journal of Medicine, pp. 130-139, vol. 371, No. 2.
Berger, Steinhoff (2011)—Pruritus in elderly patients—eruptions of senescence, Seminars in Cutaneous Medicine and Surgery, pp. 113-117, vol. 30, No. 2.
Bissonnette et al. (2016)—Topical tofacitinib for atopic dermatitis: a phase IIa randomized trial, British Journal of Dermatology, pp. 902-911, vol. 175, No. 5.
Cevikbas et al. (2014)—A sensory neuron-expressed IL-31 receptor mediates T helper cell-dependent itch: Involvement of TRPV1 and TRPA1, Journal of Allergy and Clinical Immunology, pp. 448-460, vol. 133, No. 2.
Cyphert et al. (2009)—Cooperation between mast cells and neurons is essential for antigen-mediated bronchoconstriction, Journal of immunology, pp. 7430-7439, vol. 182, No. 12.
Dillon et al. (2004)—Interleukin 31, a cytokine produced by activated T cells, induces dermatitis in mice, Nature Immunology, pp. 752-760, vol. 5, No. 7.
Fukuyama et al. (2015)—Topically Administered Janus-Kinase Inhibitors Tofacitinib and Oclacitinib Display Impressive Antipruritic and Anti-Inflammatory Responses in a Model of Allergic Dermatitis., The Journal of pharmacology and experimental therapeutics, pp. 394-405, vol. 354, No. 3.
Fukuyama et al. (Epub Jan. 26, 2017)—Janus kinase inhibitors display broad anti-itch properties: A possible link through the TRPV1 receptor, Journal of Allergy and Clinical Immunology, pp. 306-309, vol. 140, No. 1.
Gabanyi et al. (2016)—Neuro-immune Interactions Drive Tissue Programming in Intestinal Macrophages, Cell, pp. 378-391, vol. 164, No. 3.
Gittler et al. (2012)—Progressive activation of Th2/Th22 cytokines and selective epidermal proteins characterizes acute and chronic atopic dermatitis, Journal of Allergy and Clinical Immunology, pp. 1344-1354, vol. 130, No. 6.
Hammad, Lambrecht (2015)—Barrier Epithelial Cells and the Control of Type 2 Immunity, Immunity, pp. 29-40, vol. 43, No. 1.
Hirahara et al. (2016)—Targeting cytokine signaling in autoimmunity: back to the future and beyond, Current Opinion in Immunology, pp. 89-97, vol. 43.
Imai et al. (2013)—Skin-specific expression of IL-33 activates group 2 innate lymphoid cells and elicits atopic dermatitis-like inflammation in mice, Proceedings of the National Academy of Sciences, pp. 13921-13926, vol. 110, No. 34.
International Search Report and Written Opinion dated May 5, 2017 in corresponding International Application No. PCT/US17/18097 filed Feb. 16, 2017, 8 pages.

(Continued)

*Primary Examiner* — Jeffrey H Murray

(57) ABSTRACT

The present invention provides methods for treating pruritus in a subject in need thereof comprising administering a therapeutically effective amount of a JAK inhibitor. Also provided are methods of intranasal administration of JAK inhibitors for use in treating pruritus.

21 Claims, 20 Drawing Sheets

Specification includes a Sequence Listing.

(56) References Cited

OTHER PUBLICATIONS

Kabouridis, Pachnis (2015)—Emerging roles of gut microbiota and the immune system in the development of the enteric nervous system, Journal of Clinical Investigation, pp. 956-964, vol. 125, No. 3.
Kaplan (2004)—Chronic urticaria: Pathogenesis and treatment, Journal of Allergy and Clinical Immunology, pp. 465-474, vol. 114, No. 3.
Kashem et al. (2015)—Nociceptive Sensory Fibers Drive Interleukin-23 Production from CD301b+ Dermal Dendritic Cells and Drive Protective Cutaneous Immunity, Immunity, pp. 515-526, vol. 43, No. 3.
Kelly-Welch et al. (2003)—Interleukin-4 and Interleukin-13 Signaling, Science, pp. 1527-1529, vol. 300.
Kim, Artis (2015)—Group 2 Innate Lymphoid Cells in Health and Disease, Cold Spring Harbor Laboratory Press, vol. 7.
Kim et al. (2014)—Basophils Promote Innate Lymphoid Cell Responses in Inflamed Skin, The Journal of Immunology, pp. 3717-3725, vol. 193, No. 7.
Kim et al. (2013)—Innate lymphoid cells and allergic inflammation, Current Opinion in Immunology, pp. 738-744, vol. 25, No. 6.
Kim et al. (2013)—TSLP Elicits IL-33—Independent Innate Lymphoid Cell Responses to Promote Skin Inflammation, Published Sci. Transl. Med, pp. 1-11, vol. 5, No. 5.
Kini et al. (2011)—The impact of pruritus on quality of life: The skin equivalent of pain, Archives of Dermatology, pp. 1153-1156, vol. 147, No. 10.
Levy et al. (2015)—Treatment of recalcitrant atopic dermatitis with the oral Janus kinase inhibitor tofacitinib citrate, Journal of the American Academy of Dermatology, pp. 395-399, vol. 73, No. 3.
Li et al. (2006)—Topical vitamin D3 and low-calcemic analogs induce thymic stromal lymphopoietin in mouse keratinocytes and trigger an atopic dermatitis, Proceedings of the National Academy of Sciences, pp. 11736-11741, vol. 103, No. 31.
Li et al. (2009)—Induction of thymic stromal lymphopoietin expression in keratinocytes is necessary for generating an atopic dermatitis upon application of the active vitamin D3 analogue MC903 on mouse skin, Journal of Investigative Dermatology, pp. 498-502, vol. 129, No. 2.
Liu et al. (2016)—IL-33/ST2 signaling excites sensory neurons and mediates itch response in a mouse model of poison ivy contact allergy, Proceedings of the National Academy of Sciences, pp. E7572-E7579, vol. 113, No. 47.
Liu et al. (2009)—Sensory Neuron-Specific GPCR Mrgprs Are Itch Receptors Mediating Chloroquine-Induced Pruritus, Cell, pp. 1353-1365, vol. 139, No. 7.
Lock, Unsworth (2003)—Immunoglobulins and immunoglobulin subclasses in the elderly, Annals of Clinical Biochemistry, pp. 143-148, vol. 40, No. 2.
Malin et al. (2007)—Production of dissociated sensory neuron cultures and considerations for their use in studying neuronal function and plasticity, Nature Protocols, pp. 152-160, vol. 2, No. 1.
Matterne et al. (2011)—Prevalence, correlates and characteristics of chronic pruritus: A population-based cross-sectional study, Acta Dermato-Venereologica, pp. 674-679, vol. 91, No. 6.
Maurer et al. (2013)—Omalizumab for the Treatment of Chronic Idiopathic or Spontaneous Urticaria, New England Journal of Medicine, pp. 924-935, vol. 368, No. 10.
Mohrs et al. (2001)—Analysis of type 2 immunity in vivo with a bicistronic IL-4 reporter, Immunity, pp. 303-311, vol. 15, No. 2.
Mollanazar et al. (2016)—Retrospective analysis of data from an itch center: Integrating validated tools in the electronic health record, Journal of the American Academy of Dermatology, pp. 842-844, vol. 75, No. 4.
Mollanazar et al. (2015)—Mediators of Chronic Pruritus in Atopic Dermatitis: Getting the Itch Out? Clinical Reviews in Allergy and Immunology, pp. 263-292, vol. 51, No. 3.
Morita et al. (2015)—HTR7 Mediates Serotonergic Acute and Chronic Itch, Neuron, pp. 124-138, vol. 87, No. 1.
Norman (2003)—Xerosis and pruritus in the elderly: Recognition and management, Dermatologic Therapy, pp. 254-259, vol. 16.
Noti et al. (2014)—Exposure to food allergens through inflamed skin promotes intestinal food allergy through the thymic stromal lymphopoietin-basophil axis, Journal of Allergy and Clinical Immunology, pp. 1390-1399, vol. 133, No. 5.
Noti et al. (2013)—Thymic stromal lymphopoietin-elicited basophil responses promote eosinophilic esophagitis, Nature Medicine, pp. 1005-1013, vol. 19, No. 8.
Oetjen et al. (2016)—New insights into basophil heterogeneity, Seminars in Immunopathology, pp. 549-561, vol. 38, No. 5.
Ordovas-Montanes et al. (2015)—The Regulation of Immunological Processes by Peripheral Neurons in Homeostasis and Disease, Trends in Immunology, pp. 578-604, vol. 36, No. 10.
Palm et al. (2012)—Allergic host defences, Nature, pp. 465-472, vol. 484, No. 7395.
Patel, Yosipovitch (2010)—The management of chronic pruritus in the elderly, Skin therapy letter, pp. 5-9, vol. 15, No. 8.
Provinciali et al. (2009)—Reference values for CD4+ and CD8+ T lymphocytes with naive or memory phenotype and their association with mortality in the elderly, Gerontology, pp. 314-321, vol. 55, No. 3.
Raychaudhuri, Farber (1993)—Are sensory nerves essential for the development of psoriatic lesions? Journal of the American Academy of Dermatology, pp. 488-489, vol. 28, No. 3.
Reich et al. (2011)—Pruritus in the elderly, Clinics in Dermatology, pp. 15-23, vol. 29, No. 1.
Riol-Blanco et al. (2014)—Nociceptive sensory neurons drive interleukin-23-mediated psoriasiform skin inflammation, Nature, pp. 157-161, vol. 510, No. 7503.
Roediger et al. (2013)—Cutaneous immunosurveillance and regulation of inflammation by group 2 innate lymphoid cells, Nature Immunology, pp. 564-573, vol. 14, No. 6.
Roosterman et al. (2006)—Neuronal Control of Skin Function: The Skin as a Neuroimmunoendocrine Organ, Physiological Reviews, pp. 1309-1379, vol. 86, No. 4.
Salimi et al. (2013)—A role for IL-25 and IL-33-driven type-2 innate lymphoid cells in atopic dermatitis, The Journal of Experimental Medicine, pp. 2939-2950, vol. 210, No. 13.
Sandmand et al. (2002)—Is ageing associated with a shift in the balance between Type 1 and Type 2 cytokines in humans? Clinical and Experimental Immunology, pp. 107-114, vol. 127, No. 1.
Schwartz et al. (2016)—Type I/II cytokines, JAKs, and new strategies for treating autoimmune diseases, Nature Reviews Rheumatology, pp. 25-36, vol. 12, No. 1.
Simpson et al. (2016)—Two Phase 3 Trials of Dupilumab versus Placebo in Atopic Dermatitis, New England Journal of Medicine, pp. 2335-2348, vol. 375, No. 24.
Siracusa et al. (2013)—Basophils and allergic inflammation, Journal of Allergy and Clinical Immunology, pp. 789-801, vol. 132, No. 4.
Siracusa et al. (2011)—TSLP promotes interleukin-3-independent basophil haematopoiesis and type 2 inflammation, Nature, pp. 229-233, vol. 477, No. 7363.
Siracusa et al. (2013)—Thymic stromal lymphopoietin-mediated extramedullary hematopoiesis promotes allergic inflammation, Immunity, pp. 1158-1170, vol. 39, No. 6.
Sonkoly et al. (2006)—IL-31: A new link between T cells and pruritus in atopic skin inflammation, Journal of Allergy and Clinical Immunology, pp. 411-417, vol. 117, No. 2.
Ständer et al. (2007)—Clinical classification of itch: A position paper of the international forum for the study of itch, Acta Dermato-Venereologica, pp. 291-294, vol. 87, No. 4.
Subramanian et al. (2005)—Gene set enrichment analysis: A knowledge-based approach for interpreting genome-wide expression profiles, Proceedings of the National Academy of Sciences, pp. 15545-15550, vol. 102, No. 43.
Talbot et al. (2015)—Silencing Nociceptor Neurons Reduces Allergic Airway Inflammation, Neuron, pp. 341-355, vol. 87, No. 2.
Thaçi et al. (2016)—Efficacy and safety of dupilumab in adults with moderate-to-severe atopic dermatitis inadequately controlled by

(56) References Cited

OTHER PUBLICATIONS topical treatments: A randomised, placebo-controlled, dose-ranging phase 2b trial, The Lancet, pp. 40-52, vol. 387, No. 10013.
Usoskin et al. (2015)—Unbiased classification of sensory neuron types by large-scale single-cell RNA sequencing, Nature Neuroscience, pp. 145-153, vol. 18, No. 1.
Valdes-Rodriguez et al. (2015)—Chronic Pruritus in the Elderly: Pathophysiology, Diagnosis and Management, Drugs and Aging, pp. 201-215, vol. 32, No. 3.
Valtcheva et al. (2016)—Surgical extraction of human dorsal root ganglia from organ donors and preparation of primary sensory neuron cultures, Nature Protocols, pp. 1877-1888, vol. 11, No. 10.
Veiga-Fernandes, Mucida (2016)—Neuro-Immune Interactions at Barrier Surfaces, Cell, pp. 801-811, vol. 165, No. 4.
Weidinger, Novak (2016)—Atopic dermatitis, The Lancet, pp. 1109-1122, vol. 387, No. 10023.
Wilson et al. (2013)—The epithelial cell-derived atopic dermatitis cytokine TSLP activates neurons to induce itch, Cell, pp. 285-295, vol. 155, No. 2.
Xu et al. (2016)—Immune dysregulation underlies a subset of patients with chronic idiopathic pruritus, Journal of the American Academy of Dermatology, pp. 1017-1020, vol. 74, No. 5.
Yosipovitch, Bernhard (2013)—Chronic Pruritus, New England Journal of Medicine, pp. 1625-1634, vol. 368, No. 17.
Zinselmeyer et al. (2009)—Chapter 16 Two-Photon Microscopy and Multidimensional Analysis of Cell Dynamics, in Methods in Enzymology, p. 349-378.
Bowser, Atopic Dermatitis patients achieved freedom from itch on JAK inhibitor upadacitinib, Dermatology News, Jun. 27, 2019, 4 pages.
Del Bel et al., JAK1 gain-of-function causes an autosomal dominant immune dys-regulatory and hypereosinophilic syndrome J Allergy Clin Immunol, Jan. 19, 2017, vol. 139, No. 6, 10 pages.
Incyte, Incyte Announces Positive Topline Results From Phase 3 TRuE-AD Program Evaluating Ruxolitinib Cream in Patients With Atopic Dermatitis, Businesswire, Feb. 19, 2020, 2 pages.
Keown, Pfizer's JAK1 Inhibitor Abrocitinib Hits the Mark in Fourth Atopic Dermatitis Trial, Filter News, Jun. 11, 2020, 4 pages.
Kim et al., Treatment of atopic dermatitis with ruxolitinib cream (JAK1/JAK2 inhibitor) or triamcinolone cream, available online Oct. 17, 2019, J Allergy Clin Immunol vol. 145, No. 2, pp. 572-582.
Oetjen et al., Sensory Neurons Co-opt Classical Immune Signaling Pathways to Mediate Chronic Itch, Sep. 21, 2017, Cell, vol. 171, 217-228.
Wang et al., Treatment of Refractory Chronic Pruritus of Unknown Origin With to Patients With Rheumatoid Arthritis, JAMA Dermatology, Dec. 2019 vol. 155, No. 12, pp. 1426-1428.
Worm et al., Efficacy and safety of topical delgocitinib in patients with chronic hand eczema: data from a randomized, double-blind, vehicle-controlled phase IIa study, British Journal of Dermatology, available online Aug. 29, 2019, vol. 182, pp. 1103-1110.

SEQUENCE LISTING

```
<160> NUMBER OF SEQ ID NOS: 23

<210> SEQ ID NO 1
<211> LENGTH: 20
<212> TYPE: DNA
<213> ORGANISM: Artificial Sequence
<220> FEATURE:
<223> OTHER INFORMATION: synthetic primer

<400> SEQUENCE: 1
tgcaaatggc agccctggtg                                                   20

<210> SEQ ID NO 2
<211> LENGTH: 24
<212> TYPE: DNA
<213> ORGANISM: Artificial Sequence
<220> FEATURE:
<223> OTHER INFORMATION: synthetic primer

<400> SEQUENCE: 2
gtggagtcat actggaacat gtag                                              24

<210> SEQ ID NO 3
<211> LENGTH: 19
<212> TYPE: DNA
<213> ORGANISM: Artificial Sequence
<220> FEATURE:
<223> OTHER INFORMATION: synthetic primer

<400> SEQUENCE: 3
aatggtgaag gtcggtgtg                                                    19

<210> SEQ ID NO 4
<211> LENGTH: 21
<212> TYPE: DNA
<213> ORGANISM: Artificial Sequence
<220> FEATURE:
<223> OTHER INFORMATION: synthetic primer

<400> SEQUENCE: 4
cagaaccagc aagcacgcag a                                                 21
```

<210> SEQ ID NO 5
<211> LENGTH: 21
<212> TYPE: DNA
<213> ORGANISM: Artificial Sequence
<220> FEATURE:
<223> OTHER INFORMATION: synthetic primer

<400> SEQUENCE: 5
gttacaggaa caagaccagc a                                      21

<210> SEQ ID NO 6
<211> LENGTH: 17
<212> TYPE: DNA
<213> ORGANISM: Artificial Sequence
<220> FEATURE:
<223> OTHER INFORMATION: synthetic primer

<400> SEQUENCE: 6
tggagcctga actcgca                                           17

<210> SEQ ID NO 7
<211> LENGTH: 23
<212> TYPE: DNA
<213> ORGANISM: Artificial Sequence
<220> FEATURE:
<223> OTHER INFORMATION: synthetic primer

<400> SEQUENCE: 7
tgagcaagct tctcccactg agc                                    23

<210> SEQ ID NO 8
<211> LENGTH: 22
<212> TYPE: DNA
<213> ORGANISM: Artificial Sequence
<220> FEATURE:
<223> OTHER INFORMATION: synthetic primer

<400> SEQUENCE: 8
agaattagta acacaggcac ca                                     22

<210> SEQ ID NO 9
<211> LENGTH: 22
<212> TYPE: DNA
<213> ORGANISM: Artificial Sequence
<220> FEATURE:
<223> OTHER INFORMATION: synthetic primer

<400> SEQUENCE: 9
caaggatcta accagggtct tc                                     22

<210> SEQ ID NO 10
<211> LENGTH: 23
<212> TYPE: DNA
<213> ORGANISM: Artificial Sequence
<220> FEATURE:
<223> OTHER INFORMATION: synthetic primer

<400> SEQUENCE: 10
acaggtggct gaacttctgt ggc                                    23

<210> SEQ ID NO 11
<211> LENGTH: 21
<212> TYPE: DNA
<213> ORGANISM: Artificial Sequence
<220> FEATURE:
<223> OTHER INFORMATION: synthetic primer

```
<400> SEQUENCE: 11
gagattttcg acagagacgc t                                              21

<210> SEQ ID NO 12
<211> LENGTH: 19
<212> TYPE: DNA
<213> ORGANISM: Artificial Sequence
<220> FEATURE:
<223> OTHER INFORMATION: synthetic primer

<400> SEQUENCE: 12
ctgttggtgc tgctactgt                                                 19

<210> SEQ ID NO 13
<211> LENGTH: 28
<212> TYPE: DNA
<213> ORGANISM: Artificial Sequence
<220> FEATURE:
<223> OTHER INFORMATION: synthetic primer

<400> SEQUENCE: 13
tcgtcatctg agaggccata aacaactc                                       28

<210> SEQ ID NO 14
<211> LENGTH: 22
<212> TYPE: DNA
<213> ORGANISM: Artificial Sequence
<220> FEATURE:
<223> OTHER INFORMATION: synthetic primer

<400> SEQUENCE: 14
gatcgtctgc ttctcttaca cc                                             22

<210> SEQ ID NO 15
<211> LENGTH: 20
<212> TYPE: DNA
<213> ORGANISM: Artificial Sequence
<220> FEATURE:
<223> OTHER INFORMATION: synthetic primer

<400> SEQUENCE: 15
tagtgccgtt ctgtgatcag                                                20

<210> SEQ ID NO 16
<211> LENGTH: 20
<212> TYPE: DNA
<213> ORGANISM: Artificial Sequence
<220> FEATURE:
<223> OTHER INFORMATION: synthetic primer

<400> SEQUENCE: 16
gacgtggtca gtgcggataa                                                20

<210> SEQ ID NO 17
<211> LENGTH: 20
<212> TYPE: DNA
<213> ORGANISM: Artificial Sequence
<220> FEATURE:
<223> OTHER INFORMATION: synthetic primer

<400> SEQUENCE: 17
ctgaaatctg ccgggtcgtt                                                20

<210> SEQ ID NO 18
```

```
<211> LENGTH: 20
<212> TYPE: DNA
<213> ORGANISM: Artificial Sequence
<220> FEATURE:
<223> OTHER INFORMATION: synthetic primer

<400> SEQUENCE: 18
cttgcggtgc ttgttaacgg                                              20

<210> SEQ ID NO 19
<211> LENGTH: 21
<212> TYPE: DNA
<213> ORGANISM: Artificial Sequence
<220> FEATURE:
<223> OTHER INFORMATION: synthetic primer

<400> SEQUENCE: 19
cgagtgaacg ggtacgtttc t                                            21

<210> SEQ ID NO 20
<211> LENGTH: 20
<212> TYPE: DNA
<213> ORGANISM: Artificial Sequence
<220> FEATURE:
<223> OTHER INFORMATION: synthetic primer

<400> SEQUENCE: 20
cctacggaaa ctcagccacc                                              20

<210> SEQ ID NO 21
<211> LENGTH: 21
<212> TYPE: DNA
<213> ORGANISM: Artificial Sequence
<220> FEATURE:
<223> OTHER INFORMATION: synthetic primer

<400> SEQUENCE: 21
cgagtgaacg ggtacgtttc t                                            21

<210> SEQ ID NO 22
<211> LENGTH: 21
<212> TYPE: DNA
<213> ORGANISM: Artificial Sequence
<220> FEATURE:
<223> OTHER INFORMATION: synthetic primer

<400> SEQUENCE: 22
cacaagaaaa gctcgcagac a                                            21

<210> SEQ ID NO 23
<211> LENGTH: 23
<212> TYPE: DNA
<213> ORGANISM: Artificial Sequence
<220> FEATURE:
<223> OTHER INFORMATION: synthetic primer

<400> SEQUENCE: 23
ggtggttcag ttttcgctat gtt                                          23
```

JAK INHIBITORS AND USES THEREOF

CROSS-REFERENCE TO RELATED APPLICATIONS

This application claims the benefit of priority to PCT International Application No. PCT/US2017/018097 filed 16 Feb. 2017, which claims the benefit of U.S. Provisional Application Ser. No. 62/295,875 filed on 16 Feb. 2016, each of which is incorporated herein by reference in its entirety.

STATEMENT REGARDING FEDERALLY SPONSORED RESEARCH OR DEVELOPMENT

Not Applicable.

MATERIAL INCORPORATED-BY-REFERENCE

The Sequence Listing, which is a part of the present disclosure, includes a computer readable form comprising nucleotide and/or amino acid sequences of the present invention. The subject matter of the Sequence Listing is incorporated herein by reference in its entirety.

FIELD OF THE INVENTION

The present disclosure generally relates to methods for treating pruritus, including chronic idiopathic pruritus, and pruritic components of other pruritic disorders as described herein, in a subject in need thereof comprising administering a therapeutically effective amount of a JAK inhibitor.

BACKGROUND OF THE INVENTION

Itchiness, i.e. the sensation that produces the desire to scratch, is clinically referred to as "pruritus." There are multiple etiologies of pruritus, and it is often a major clinical challenge to diagnose the underlying etiology in order to adequately treat.

The multidimensional character of the itch experience is reflected in the complexity of itch processing in the brain. Multiple neural pathways and molecular mechanisms responsible for producing the sensation of itch have been identified, including histamine-dependent and histamine-independent pathways. Ideally, effective treatment of pruritus would be informed by an understanding of the underlying etiology and the neuronal pathways involved in each specific disease. Although recent neurophysiological research has led to a better understanding of neural pathways involved in itch response, the pathophysiology is still not completely understood. Accordingly, the state of the art does not allow a medical practitioner to predict whether a treatment will effectively control pruritus of different etiologies, particularly when the origin of pruritus cannot be identified.

SUMMARY OF THE INVENTION

Among the various aspects of the present disclosure is the provision of a method of treatment of pruritus using JAK inhibitors.

In some embodiments, the method includes administering to the subject a therapeutically effective amount of a JAK inhibitor.

In some embodiments, the subject is diagnosed with pruritus or chronic idiopathic pruritus and treatment prevents or reduces pruritus in the subject.

In some embodiments, the subject has extremely severe itching or severe itching; or the subject has moderate or mild itching.

In some embodiments, the pruritus has lasted for at least at least seven weeks; the pruritus has lasted for at least at least eight weeks; the pruritus has lasted for at least at least nine weeks; or the pruritus has lasted for at least at least ten weeks.

In some embodiments, the treatment reduces severity of itching in a subject, increases number of itch-free days in the subject, improves quality of life of the subject, or any combination thereof.

In some embodiments, the subject is predisposed to pruritus or chronic idiopathic pruritus and treatment prevents a reoccurrence of chronic pruritus in the subject or reduces frequency of acute pruritus in the subject.

In some embodiments, the JAK inhibitor is of formula (I),

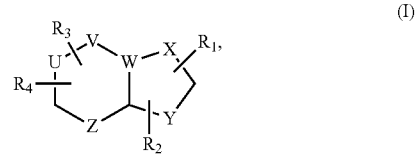

or a pharmaceutically acceptable salt thereof, including all tautomers and stereoisomers thereof wherein:

U, V, W, X, Y, and Z, are selected from the group consisting of C and N;

$R_1$, $R_2$, $R_3$, or $R_4$ are independently selected from the group consisting of hydrogen; unsubstituted or substituted alkyl; unsubstituted or substituted alkenes; unsubstituted or substituted alkyne; acetamide;

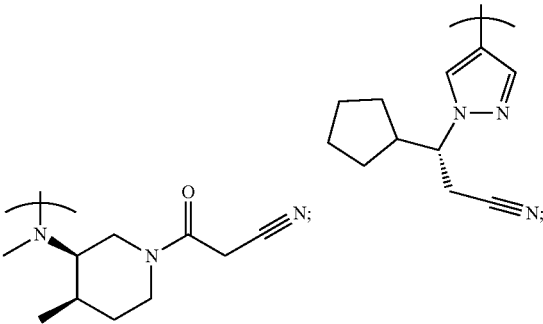

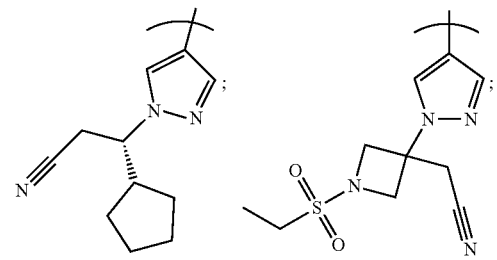

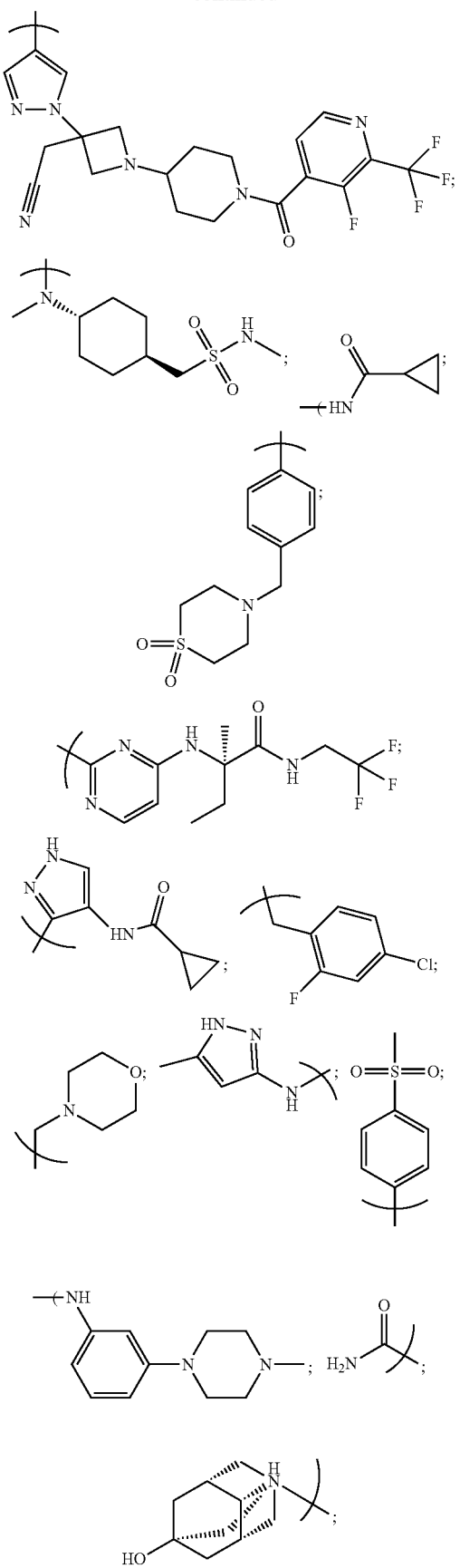

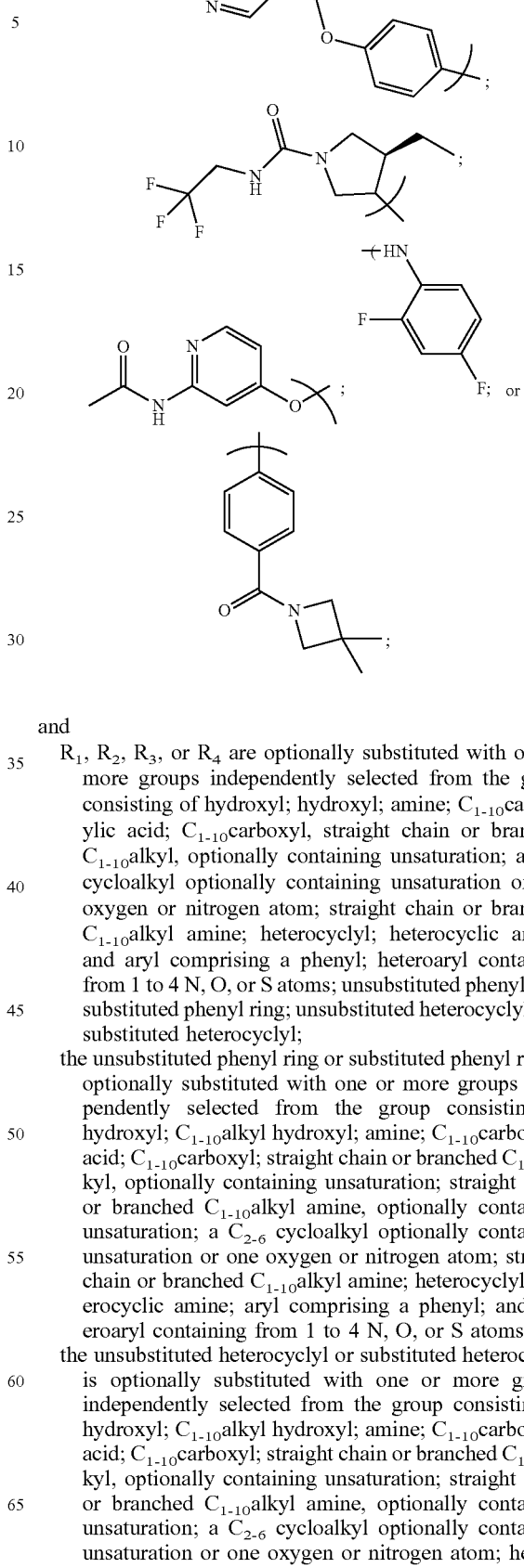

and

R₁, R₂, R₃, or R₄ are optionally substituted with one or more groups independently selected from the group consisting of hydroxyl; hydroxyl; amine; $C_{1-10}$carboxylic acid; $C_{1-10}$carboxyl, straight chain or branched $C_{1-10}$alkyl, optionally containing unsaturation; a $C_{2-6}$ cycloalkyl optionally containing unsaturation or one oxygen or nitrogen atom; straight chain or branched $C_{1-10}$alkyl amine; heterocyclyl; heterocyclic amine; and aryl comprising a phenyl; heteroaryl containing from 1 to 4 N, O, or S atoms; unsubstituted phenyl ring; substituted phenyl ring; unsubstituted heterocyclyl; and substituted heterocyclyl;

the unsubstituted phenyl ring or substituted phenyl ring is optionally substituted with one or more groups independently selected from the group consisting of hydroxyl; $C_{1-10}$alkyl hydroxyl; amine; $C_{1-10}$carboxylic acid; $C_{1-10}$carboxyl; straight chain or branched $C_{1-10}$alkyl, optionally containing unsaturation; straight chain or branched $C_{1-10}$alkyl amine, optionally containing unsaturation; a $C_{2-6}$ cycloalkyl optionally containing unsaturation or one oxygen or nitrogen atom; straight chain or branched $C_{1-10}$alkyl amine; heterocyclyl; heterocyclic amine; aryl comprising a phenyl; and heteroaryl containing from 1 to 4 N, O, or S atoms; and the unsubstituted heterocyclyl or substituted heterocyclyl is optionally substituted with one or more groups independently selected from the group consisting of hydroxyl; $C_{1-10}$alkyl hydroxyl; amine; $C_{1-10}$carboxylic acid; $C_{1-10}$carboxyl; straight chain or branched $C_{1-10}$alkyl, optionally containing unsaturation; straight chain or branched $C_{1-10}$alkyl amine, optionally containing unsaturation; a $C_{2-6}$ cycloalkyl optionally containing unsaturation or one oxygen or nitrogen atom; heterocyclyl; straight chain or branched C$_{1-10}$alkyl amine; heterocyclic amine; and aryl comprising a phenyl; and heteroaryl containing from 1 to 4 N, O, or S atoms.

In some embodiments, the JAK inhibitor is selected from one or more of the group consisting of: tofacitinib, ruxolitinib, baricitinib, INCB039110, oclacitinib, AZD1480, fedratinib, AT9283, AG-490, momelotinib, WP1066, TG101209, gandotinib, NVP-BSK805, AZ 960, CEP-33779, Pacritinib, WHI-P154, XL019, S-Ruxolitinib, ZM 39923, Decernotinib, Cerdulatinib, filgotinib, FLLL32, BMS-911543, peficitinib, GLPG0634, GLPG0634 analogue, Go6976, curcumol, cucurbitacin, lestaurtinib, upadacitinib, CHZ868, Solcitinib (GSK 2586184), NS-018; or a derivative thereof; or pharmaceutically acceptable salt thereof.

In some embodiments, the JAK inhibitor is

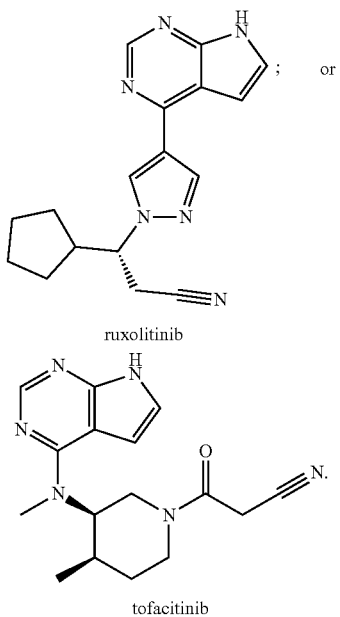

In some embodiments, the JAK inhibitor is parenterally administered.

In some embodiments, the JAK inhibitor is administered intrathecally.

In some embodiments, the JAK inhibitor is administered intranasally.

In some embodiments, the JAK inhibitor is administered orally.

In some embodiments, the JAK inhibitor is administered on a daily basis.

In some embodiments, the JAK inhibitor is administered daily for at least 7 consecutive days.

In some embodiments, the JAK inhibitor is administered daily for at least 14 consecutive days.

In some embodiments, the JAK inhibitor is administered daily for at least 30 consecutive days.

In some embodiments, the pruritus is a symptom of broad activation of immune responses or dysregulation of neuronal processes and sensory perception.

In some embodiments, the subject is diagnosed with, or the pruritus is a symptom of, a disease or condition selected from one or more of the group consisting of: allergic reaction, arthropod bites, athlete's foot, atopic dermatitis (AD), atopic itch, atopic dermatitis-associated itch, autoimmune connective tissue disease, bacterial infection, biliary itch, broad activation of immune responses, body louse, bullous diseases, brachioradial pruritus, brain tumors, chronic idiopathic pruritus, contact dermatitis, cholestasis, cutaneous larva migrans, cutaneous T-cell lymphoma, nervous system damage, dandruff, delusional parasitosis, dermatomyositis, dermatosis of pregnancy, diabetes mellitus, drug eruptions, dysregulation of neuronal processes and sensory perception, eczema, eosinophilic folliculitis, foreign objects or devices on skin, fungal infection, gestational pemphigoid, head lice, herpes, hidradenitis suppurativa, hives, Hodgkin's disease, hyperparathyroidism, idiopathic chronic itch, inflammation, insect infestation, insect bites, insect stings, intrahepatic cholestasis of pregnancy, iron deficiency anemia, increased accumulation of exogenous opioids or synthetic opioids, internal cancer, jaundice, lichen planus, lichen sclerosus, lupus erythematosus, lymphoma, lymphoma—associated itch, leukemia-associated itch, malignancy, mastocytosis, menopause, multiple sclerosis, neoplasm, nerve irritation, neurogenic itch, neuropathic itch, notalgia paresthetica, notalgia obsessive-compulsive disorders, paresthetica, parasitic infection, papular uritcaria, pediculosis, peripheral neuropathy, photodermatitis, polycythemia vera, psychiatric disease, psychogenic itch, pruritic popular eruption of HIV, pruritic urticarial papules and plaques of pregnancy (PUPPP), psoriasis, psoriasis-associated itch, psoriatic itch, pubic lice, punctate palmoplantar keratoderma, renal itch, rheumatoid arthritis, scabies, scar growth, shaving, seborrheic dermatitis, stasis dermatitis, sunburn, swimmer's itch, systemic immune senescence, tactile hallucinations, Th17-associated inflammation, thyroid illness, uraemia, pruritus or uremic itch, urticaria, urticarial itch, varicella, viral infection, wound or scab healing, and xerosis.

In some embodiments, the pruritus has an inflammatory etiology; the pruritus has neuronal dysfunction etiology; or the pruritus has an unknown etiology.

In some embodiments, the JAK inhibitor is a TRPV1 inhibitor; modulates signaling of IL-4 or IL-13 pathway; or targets the IL-4Rα signaling pathway.

In some embodiments, the method further includes administration of a TRPV1 inhibitor, dupilumab, or secukinumab.

Other objects and features will be in part apparent and in part pointed out hereinafter.

DESCRIPTION OF THE DRAWINGS

Those of skill in the art will understand that the drawings, described below, are for illustrative purposes only. The drawings are not intended to limit the scope of the present teachings in any way.

The application file contains at least one drawing executed in color. Copies of this patent application publication with color drawing(s) will be provided by the Office upon request and payment of the necessary fee.

(FIG. 2A) Clinical photograph of the patient described in Case 1 (see Example 1, TABLE 2). As is the case with many CIP patients, no distinct rash was appreciable. A skin biopsy was taken at the location depicted by the arrow. (FIG. 2B) and (FIG. 2C) Skin biopsy from the patient described in Case 4 (see Example 1, TABLE 2) demonstrating (FIG. 2B) spongiosis with dense lymphocytic infiltrates (arrows) on low power (scale bar represents 500 µm), and (FIG. 2C) abundant eosinophils at high power (scale bar represents 50 µm).

(FIG. 3A) Average itch scores decreased about 50% following treatment with a JAK inhibitor for one month. Itch was assessed using the Numerical Rating Scale (NRS). (FIG. 3B) Daily itch scores (y-axis; NRS) for a single subject from (FIG. 3A) over a 70 day period of time (x-axis). The subject reported no improvement in pruritus when treated with a cyclosporine alone but reported significant improvement when switched to a JAK inhibitor (Xeljanz or tofacitinib).

(FIG. 5A) Representative gel of RT-PCR product of whole mouse dorsal root ganglia (DRG), n=4. (FIG. 5B) Representative gel of RT-PCR product of whole human DRG, N=3. (FIG. 5C) Quantification of Il4ra, Il13ra1, and Il31ra by RT-qPCR in whole mouse DRG, n=4. (FIG. 5D) Representative calcium imaging trace of mouse DRG neurons in response to recombinant murine (rm)IL-4 and potassium chloride (KCl). (FIG. 5E) Representative calcium imaging trace of mouse DRG neurons in response to rmIL-13 and KCl. (FIG. 5F) Representative calcium imaging trace of mouse DRG neurons in response to rmIL-31 and KCl. (FIG. 5G) rmIL-4-, rmIL-13-, rmIL-31-, and histamine-responsive neurons as a percentage of total mouse DRG neurons, n>500 neurons. (FIG. 5H and FIG. 5I) Venn diagrams of overlapping responses of mouse DRG neurons to stimulation with (FIG. 5H) rmIL-4 or (FIG. 5I) rmIL-13 and subsequent rmIL-31 and histamine challenge, n>300 neurons. Data are represented as mean±SEM. See also FIG. 12 and FIG. 13.

(FIG. 6A) Experimental schematic indicating daily topical treatment with vehicle control (ethanol, EtOH) or MC903 to the ears of wild type (WT) mice. (FIG. 6B) Ear thickness measurements as percent change from baseline over the course of control or MC903 treatment, n∝4 per group. (FIG. 6C) Representative histopathology and (FIG. 6D) histology score of control and MC903-treated mice, n≥4 per group. (FIG. 6E) Scratching behavior of control and MC903-treated mice on Day 0, 4, 8, and 12, n≥4 per group. (FIG. 6F) Comparison of gene row Z-scores of regularized logarithm expression values of select atopic dermatitis (AD)-associated genes in the skin of control and MC903-treated mice, n=4 per group. (FIG. 6G) RT-qPCR for Il4ra, Il5ra, and Il13ra1 in sensory trigeminal ganglia from control and MC903-treated mice, n=8 per group. Scale bars indicate 100 µm. Data are represented as mean±SEM. See also FIG. 14.

(FIG. 7A) Experimental schematic indicating daily topical treatment with vehicle control (EtOH) to one ear and MC903 to the second ear of $Na_v1.8$-tdTomato$^+$ IL-4-eGFP$^+$ mice. (FIG. 7B and FIG. 7C) Representative images of intravital two-photon imaging of (FIG. 7B) control and (FIG. 7C) MC903-treated ears. Red arrows indicate $Na_v1.8$-tdTomato$^+$ sensory fibers. Green arrows indicate IL-4-eGFP$^+$ cells. Representative stills from movies are provided in FIG. 16 and FIG. 17. (FIG. 7D) Instantaneous speed of a representative IL-4-eGFP$^+$ cell during its interactions with a sensory nerve fiber in MC903-treated skin of a $Na_v1.8$-tdTomato$^+$ IL-4-eGFP$^+$ mouse. The graph is split into three components showing the speed of the cell as it approaches, interacts with, and then leaves the sensory nerve fiber. Stills from the movie of this cell track is provided in FIG. 18. (FIG. 7E) Mean speed over the duration of imaging of IL-4-eGFP$^+$ cells in association with sensory nerve fibers compared to those not associated with nerve fibers in the MC903-treated skin of a $Na_v1.8$-tdTomato$^+$ IL-4-eGFP$^+$ mouse, n>40 cells per group. Error bars represent SD. Scale bars indicate 100 µm. See also FIG. 16-FIG. 18.

(FIG. 8A) Experimental schematic indicating daily topical treatment with MC903 to the ears of IL-4Rα$^{\Delta neuron}$ and littermate control mice. (FIG. 8B) RT-qPCR of sensory trigeminal ganglia of IL-4Rα$^{\Delta neuron}$ mice, 7 per group. (FIG. 8C) Scratching behavior of IL-4Rα$^{\Delta neuron}$ mice compared to littermate controls over the course of MC903 treatment, 7 per group. (FIG. 8D) Ear thickness measurements, (FIG. 8E) representative histopathology, and (FIG. 8F) histology score of MC903-treated IL-4Rα$^{\Delta neuron}$ mice compared to littermate controls, n≥4 per group. Scale bars indicate 100 µm. Data are represented as mean±SEM.

(FIG. 9A) Experimental schematic indicating twice daily intraperitoneal (i.p.) injection of control vehicle or high dose ruxolitinib (rux) (100 µg) during MC903 treatment to the ears of wild type (WT) mice.

(FIG. 10A and FIG. 10B) Representative gross clinical pictures of (FIG. 10A) atopic dermatitis (AD) and (FIG. 10B) chronic idiopathic pruritus (CIP). (FIG. 10C and FIG. 10D) Representative histopathology images of (FIG. 10C) AD and (FIG. 10D) CIP. (FIG. 10E) Histology score of AD and CIP patient biopsies, N≥4 per group. (FIG. 10F) Numerical Rating Scale (NRS) itch scores of AD and CIP patients, N≥22 per group. (FIG. 10G) Clustering of AD, CIP, and healthy control skin samples by gene row Z-scores of regularized logarithm expression values of the top 100 differentially expressed genes in AD versus healthy control skin. (FIG. 10H) Gene set enrichment analysis (GSEA) of a direct comparison between CIP and AD skin. Positive enrichment scores indicate enrichment in CIP. Scale bars indicate 100 μm. Data are represented as mean±SEM. See also TABLE 3 and TABLE 4.

(FIG. 11A) NRS itch scores for a cohort of CIP patients (N=5) given the JAK inhibitor tofacitinib. Each point represents a patient before and after treatment with tofacitinib. Significance was calculated using the paired t-test. Error bars represent SD. (FIG. 11B) Daily NRS itch scores of two CIP patients treated with tofacitinib including one patient treated with cyclosporine immediately preceding treatment with tofacitinib (black). See also TABLE 5.

DETAILED DESCRIPTION OF THE INVENTION

Figure 1A:
FIG. 1A-B depicts a representative photograph of (A) a subject with atopic dermatitis, and (B) a subject with CIP. Subjects with CIP lack the overt skin inflammation seen in atopic dermatitis.
Figure 1B:

The present disclosure is based, at least in part, on the discovery that immune defense mechanisms directly modulate host behavior; type 2 immune cells interact with sensory nerve fibers in the skin; sensory neuron-specific deletion of IL-4Rα or JAK1 reduces chronic itch; and clinical studies demonstrate that JAK inhibitors relieve chronic itch. As shown herein, the present disclosure provides methods for treating chronic idiopathic pruritus (CIP) in a subject in need thereof.

In particular, until now, treatment of CIP has not been successful. As described herein is a solution to an unmet need of treating CIP. Furthermore, successful treatment using an intranasal administration of JAK inhibitors has been shown herein. Intranasal administration is clinically advantageous because of the ease of use and increase in patient compliance.

In contrast to many inflammatory pruritic diseases, which are typically responsive to both topical and systemic anti-inflammatory drugs, chronic idiopathic pruritus is often resistant to many different types of anti-inflammatory treatments. Surprisingly, applicants have discovered that JAK inhibitors, which can also be anti-inflammatory compounds, can be used to effectively treat chronic idiopathic pruritus. Additional aspects of the invention are described in further detail below.

Mammals have evolved neurophysiologic reflexes such as coughing and scratching to expel invading pathogens and noxious environmental factors. It is well established that these responses are also associated with chronic inflammatory diseases such as asthma and atopic dermatitis. However, the mechanisms by which inflammatory pathways promote sensations such as itch remain poorly understood.

As described herein, type 2 cytokines, IL-4 and IL-13, directly stimulate sensory neurons and that chronic itch is dependent on neuronal IL-4Rα and JAK1 signaling. As described herein, patients with recalcitrant chronic itch markedly improve when treated with JAK inhibitors. Thus, signaling mechanisms previously ascribed to the immune system may represent novel therapeutic targets within the nervous system. Collectively, these studies reveal an evolutionarily conserved paradigm in which the sensory nervous system employs classical immune signaling pathways to influence mammalian behavior.

As described herein, it was demonstrated that sensory neurons are directly activated by the classical immune signaling molecules IL-4 and IL-13 along previously defined itch-sensory pathways, provoking the hypothesis that neuronal type 2 cytokine signaling mediates chronic itch. Indeed, employing sensory neuron-specific genetic deletion of IL-4Rα, it was found that neuronal expression of IL-4Rα is required for the development of chronic itch in an established mouse model of atopic dermatitis (AD) associated with robust itch. Based on IL-4Rα signaling biology, it was thus hypothesized that dysregulated neuronal Janus kinase (JAK) signaling may be a conserved mechanism by which chronic itch is mediated. Strikingly, both pharmacologic JAK inhibition and sensory neuron-specific genetic deletion of JAK1 demonstrated abatement of chronic itch. Although JAK inhibitors are well-established as anti-inflammatory agents (Hirahara et al., 2016; Schwartz et al., 2016), whether they exhibit additional neuromodulatory properties is not known. In support of this possibility, it was observed dramatic improvement of itch symptoms in a small cohort of CIP patients treated off-label with the JAK inhibitor tofacitinib after having failed other broad anti-inflammatory therapies. Thus, these signaling mechanisms previously ascribed to the immune system may also represent novel targets within the sensory nervous system for the treatment of chronic itch. Beyond itch, the discovery of these novel neuroimmunologic pathways including IL-4Rα and JAK1 signaling may reveal new insights into sensory perception at multiple barrier surfaces and how these pathways modulate host behavior. It is important to note that many cytokines beyond IL-4 and IL-13, even neurotransmitters (e.g., serotonin), have been shown to signal through JAKs. Thus, the mechanism of action of JAK inhibition is likely to extend beyond type 2 cytokine-associated itch such as atopic dermatitis or CIP and to many other itch disorders.

JAK Inhibitor

Another aspect of the present disclosure provides a JAK inhibitor. A "JAK inhibitor" or "Janus kinase inhibitor" can refer to a pharmaceutically active ingredient that functions by inhibiting the activity of one or more enzymes of the Janus kinase family (e.g. JAK1, JAK2, JAK3, TYK2), thereby interfering with the JAK-STAT signaling pathway. In some embodiments, a JAK inhibitor inhibits JAK1. In some embodiments, a JAK inhibitor inhibits JAK2. In some embodiments, a JAK inhibitor inhibits JAK3. In some embodiments, a JAK inhibitor inhibits TYK2. In some embodiments, a JAK inhibitor inhibits JAK1 and JAK2. In some embodiments, a JAK inhibitor inhibits JAK2 and JAK3. In some embodiments, a JAK inhibitor inhibits JAK1 and JAK3. In some embodiments, a JAK inhibitor inhibits JAK1 and TYK2. In some embodiments, a JAK inhibitor inhibits JAK2 and TYK2. In some embodiments, a JAK inhibitor inhibits JAK3 and TYK2. In some embodiments, a JAK inhibitor inhibits JAK1, JAK2 and JAK3. In some embodiments, a JAK inhibitor inhibits JAK1, JAK2 and TYK2. In some embodiments, a JAK inhibitor inhibits JAK1, JAK3 and TYK2. In some embodiments, a JAK inhibitor inhibits JAK2, JAK3 and TYK2. In some embodiments, a JAK inhibitor inhibits JAK1, JAK2, JAK3 and TYK2. Non-limiting examples of suitable JAK inhibitors may include itacitinib (INCB039110), baricitinib, cucurbitacin (JSI124), fedratinib, filgotinib (GLPG0634), gandotinib (LY2784544), lestaurtinib, momelotinib (CYT387), pacritinib, peficitinib, ruxolitinib, tofacitinib, upadacitinib, AZD1480, BMS911543, CHZ868, solcitinib (GSK2586184), NS-018, and XL-019. In exemplary embodiments, a JAK inhibitor is chosen from ruxolitinib and tofacitinib.

A "JAK inhibitor" or "Janus kinase inhibitor" can be a pharmaceutically active ingredient that functions by inhibiting the activity of one or more enzyme of the Janus kinase family (e.g. JAK1, JAK2, JAK3, TYK2), thereby interfering with the JAK-STAT signaling pathway.

In some embodiments, a JAK inhibitor can be based on a benizimidazole core,

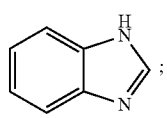

a purine core,

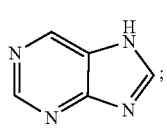

or a pyrrolo pyridine core,

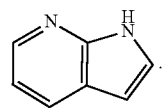

In some embodiments, a JAK inhibitor can be of formula (I),

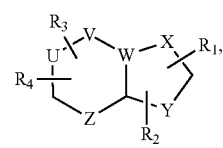

wherein U, V, W, X, Y, and Z, are selected from the group consisting of C and N.

In some embodiments, $R_1$, $R_2$, $R_3$, or $R_4$ can be hydrogen, alkyl (e.g., methyl), or acetamide;

(i)

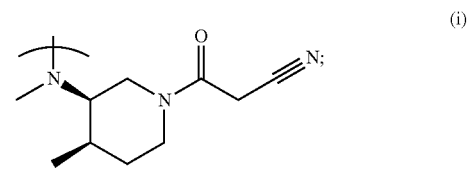

(ii)

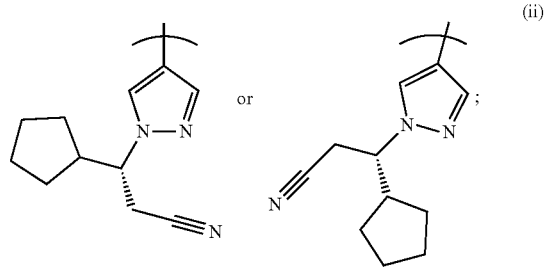

(iii)

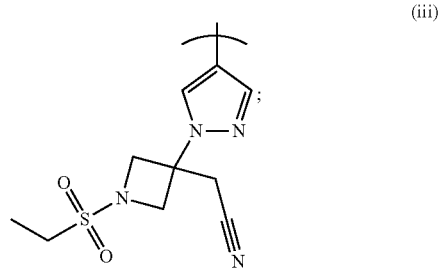

(iv)

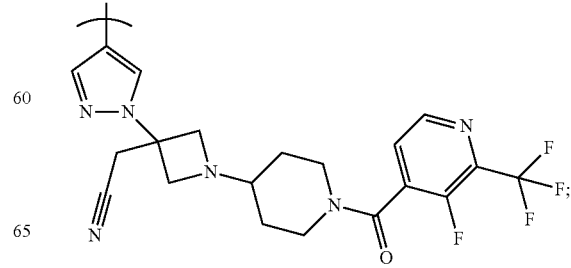

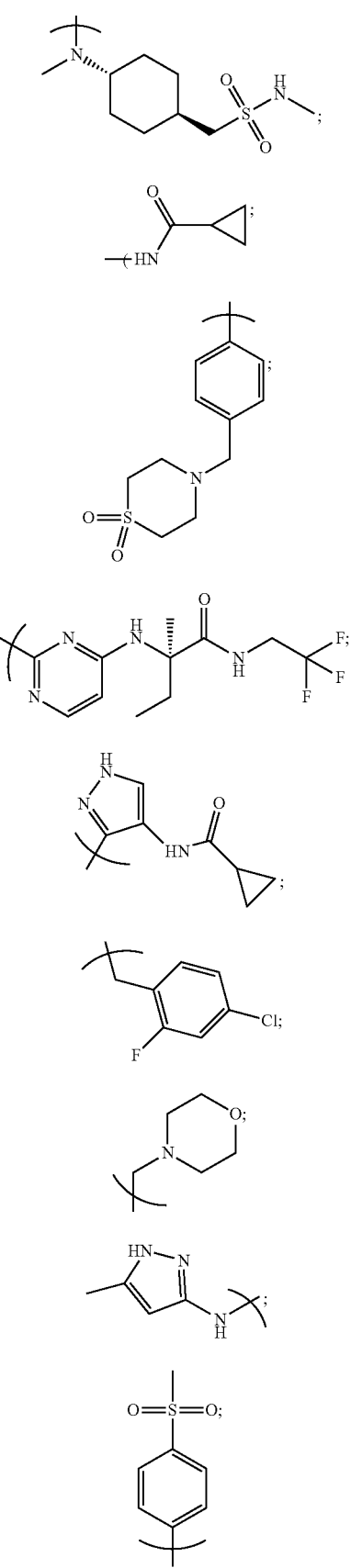
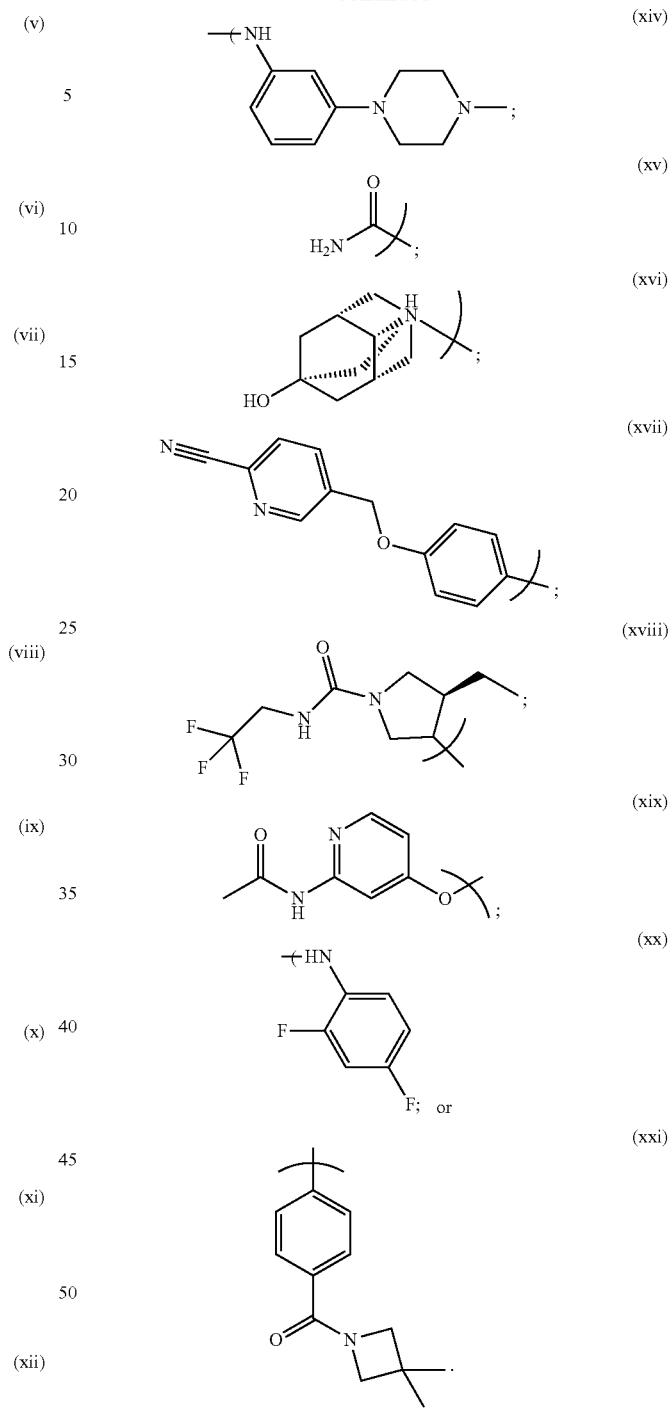

In some embodiments, $R_1$, $R_2$, $R_3$, or $R_4$ can optionally substituted with one or more groups independently selected from the group consisting of hydroxyl; $C_{1-10}$alkyl hydroxyl; amine; $C_{1-10}$carboxylic acid; $C_{1-10}$carboxyl, straight chain or branched $C_{1-10}$alkyl, optionally containing unsaturation; a $C_{2-6}$ cycloalkyl optionally containing unsaturation or one oxygen or nitrogen atom; straight chain or branched $C_{1-10}$alkyl amine; heterocyclyl; heterocyclic amine; and aryl comprising a phenyl; heteroaryl containing from 1 to 4 N, O, or S atoms; unsubstituted phenyl ring; substituted phenyl ring; unsubstituted heterocyclyl; and substituted heterocyclyl;

the unsubstituted phenyl ring or substituted phenyl ring is optionally substituted with one or more groups independently selected from the group consisting of hydroxyl; $C_{1-10}$alkyl hydroxyl; amine; $C_{1-10}$carboxylic acid; $C_{1-10}$carboxyl, straight chain or branched $C_{1-10}$alkyl, optionally containing unsaturation; straight chain or branched $C_{1-10}$alkyl amine, optionally containing unsaturation; a $C_{2-6}$ cycloalkyl optionally containing unsaturation or one oxygen or nitrogen atom; straight chain or branched $C_{1-10}$alkyl amine; heterocyclyl; heterocyclic amine; aryl comprising a phenyl; and heteroaryl containing from 1 to 4 N, O, or S atoms; and the unsubstituted heterocyclyl or substituted heterocyclyl is optionally substituted with one or more groups independently selected from the group consisting of hydroxyl; $C_{1-10}$alkyl hydroxyl; amine; $C_{1-10}$carboxylic acid; $C_{1-10}$carboxyl, straight chain or branched $C_{1-10}$alkyl, optionally containing unsaturation; straight chain or branched $C_{1-10}$alkyl amine, optionally containing unsaturation; a $C_{2-6}$ cycloalkyl optionally containing unsaturation or one oxygen or nitrogen atom; heterocyclyl; straight chain or branched $C_{1-10}$alkyl amine; heterocyclic amine; and aryl comprising a phenyl; and heteroaryl containing from 1 to 4 N, O, or S atoms.

In some embodiments, a JAK inhibitor can be tofacitinib,

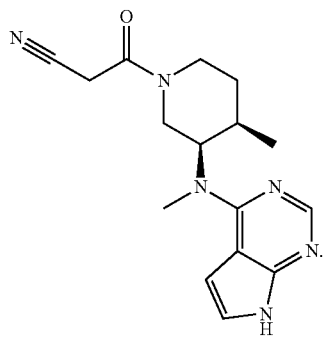 [SMILES: C[C@@H]1CCN(C(=O)CC#N)C[C@@H]1N(C)c1ncnc2[nH]ccc12]

In some embodiments, a JAK inhibitor can be ruxolitinib,

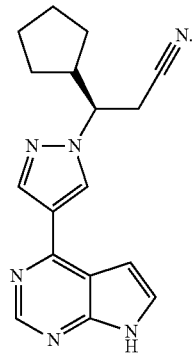 [SMILES: N#CC[C@H](C1CCCC1)n1cc(-c2ncnc3[nH]ccc23)cn1]

In some embodiments, a JAK inhibitor can be baricitinib,

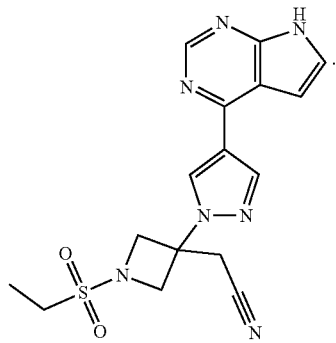 [SMILES: CCS(=O)(=O)N1CC(CC#N)(n2cc(-c3ncnc4[nH]ccc34)cn2)C1]

In some embodiments, a JAK inhibitor can be itacitinib (INCB039110),

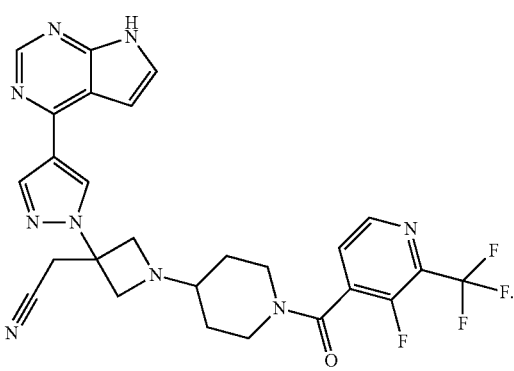 [SMILES: N#CCC1(n2cc(-c3ncnc4[nH]ccc34)cn2)CN(C2CCN(C(=O)c3ccnc(C(F)(F)F)c3F)CC2)C1]

In some embodiments, a JAK inhibitor can be oclacitinib,

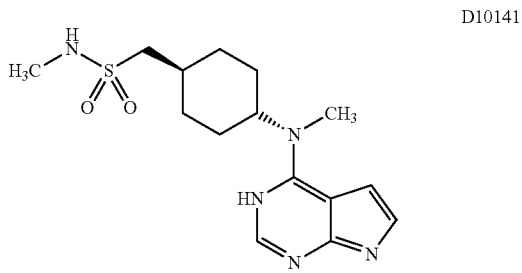

In some embodiments, a JAK inhibitor can be AZD1480,

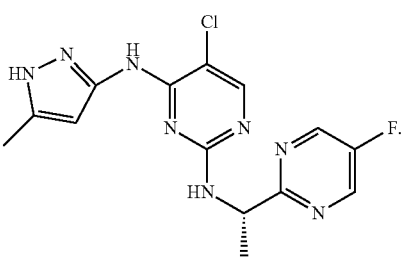 [SMILES: Cc1cc(Nc2nc(N[C@@H](C)c3ncc(F)cn3)ncc2Cl)n[nH]1]

In some embodiments, a JAK inhibitor can be fedratinib,

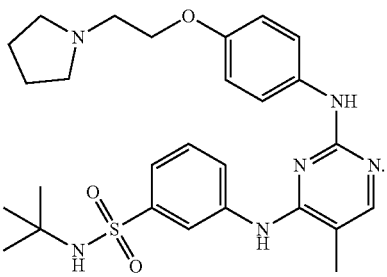 [SMILES: Cc1cnc(Nc2ccc(OCCN3CCCC3)cc2)nc1Nc1cccc(S(=O)(=O)NC(C)(C)C)c1]

In some embodiments, a JAK inhibitor can be AT9283,

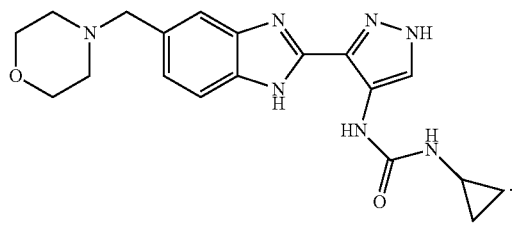 [SMILES: O=C(Nc1c[nH]nc1-c1nc2cc(CN3CCOCC3)ccc2[nH]1)NC1CC1]

In some embodiments, a JAK inhibitor can be AG-490,

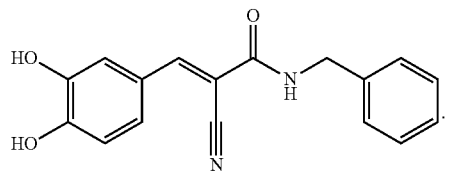 [SMILES: N#C/C(=C\c1ccc(O)c(O)c1)C(=O)NCc1ccccc1]

In some embodiments, a JAK inhibitor can be momelotinib,

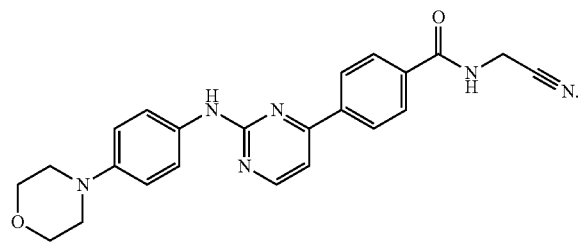 [SMILES: N#CCNC(=O)c1ccc(-c2ccnc(Nc3ccc(N4CCOCC4)cc3)n2)cc1]

In some embodiments, a JAK inhibitor can be WP1066,

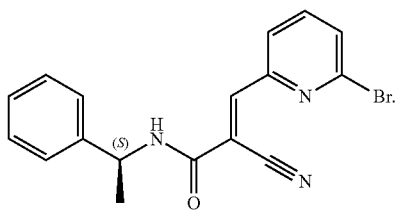

In some embodiments, a JAK inhibitor can be TG101209,

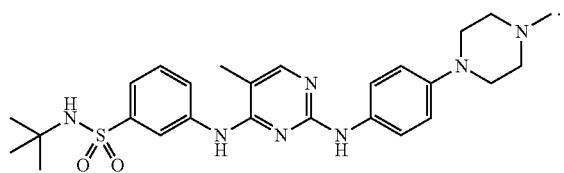 [SMILES: Cc1cnc(Nc2ccc(N3CCN(C)CC3)cc2)nc1Nc1cccc(S(=O)(=O)NC(C)(C)C)c1]

In some embodiments, a JAK inhibitor can be gandotinib,

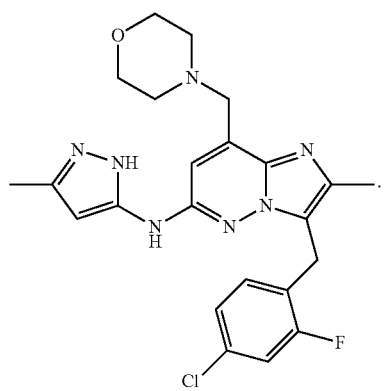

In some embodiments, a JAK inhibitor can be NVP-BSK805 2HCl,

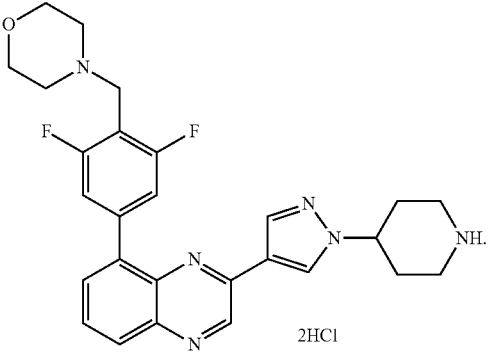 [SMILES: Fc1cc(-c2cccc3ncc(-c4cnn(C5CCNCC5)c4)nc23)cc(F)c1CN1CCOCC1]

In some embodiments, a JAK inhibitor can be AZ 960,

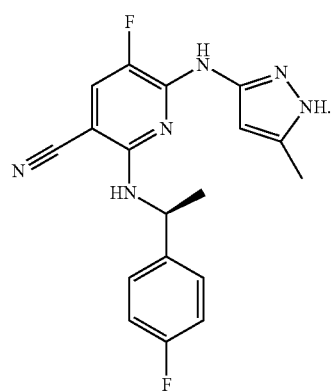 [SMILES: Cc1cc(Nc2nc(N[C@@H](C)c3ccc(F)cc3)c(C#N)cc2F)n[nH]1]

In some embodiments, a JAK inhibitor can be CEP-33779,

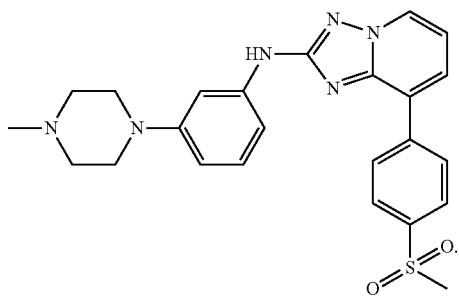 [SMILES: CN1CCN(c2cccc(Nc3nc4c(-c5ccc(S(C)(=O)=O)cc5)cccn4n3)c2)CC1]

In some embodiments, a JAK inhibitor can be pacritinib

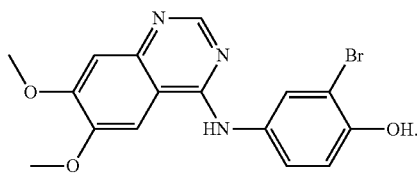 [SMILES: COc1cc2ncnc(Nc3ccc(O)c(Br)c3)c2cc1OC]

In some embodiments, a JAK inhibitor can be WHI-P154

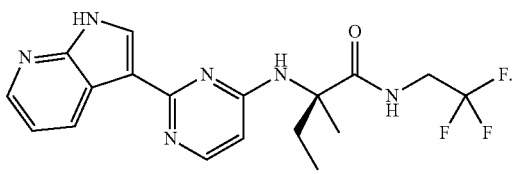 [SMILES: CC[C@@](C)(Nc1ccnc(-c2c[nH]c3ncccc23)n1)C(=O)NCC(F)(F)F]

In some embodiments, a JAK inhibitor can be XL019,

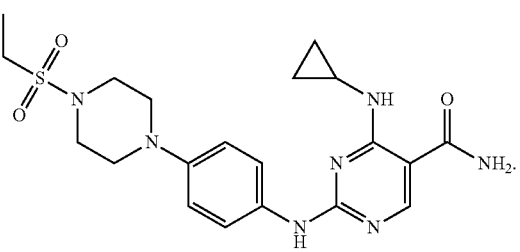 [SMILES: CCS(=O)(=O)N1CCN(c2ccc(Nc3ncc(C(N)=O)c(NC4CC4)n3)cc2)CC1]

In some embodiments, a JAK inhibitor can be S-Ruxolitinib

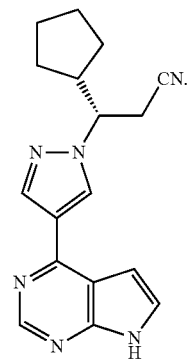

In some embodiments, a JAK inhibitor can be ZM 39923 HCl,

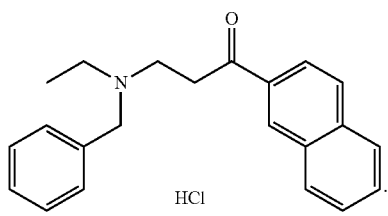

In some embodiments, a JAK inhibitor can be Decernotinib,

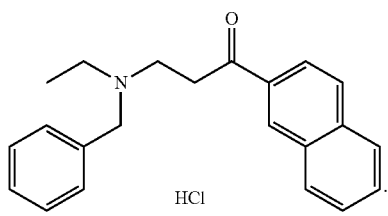

In some embodiments, a JAK inhibitor can be Cerdulatinib,

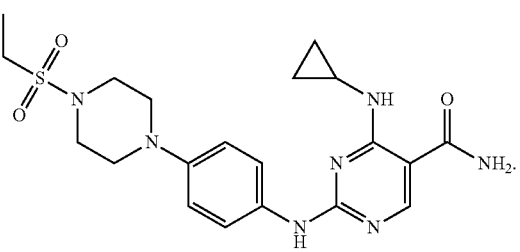 [SMILES: CCS(=O)(=O)N1CCN(c2ccc(Nc3ncc(C(N)=O)c(NC4CC4)n3)cc2)CC1]

In some embodiments, a JAK inhibitor can be filgotinib,

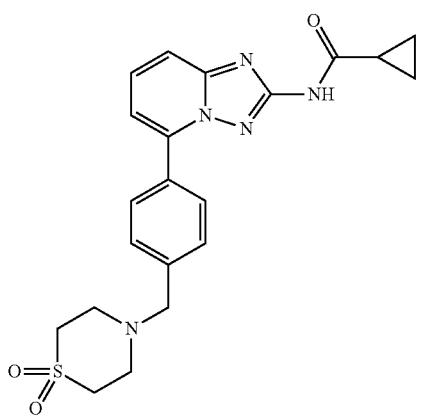

In some embodiments, a JAK inhibitor can be FLLL32,

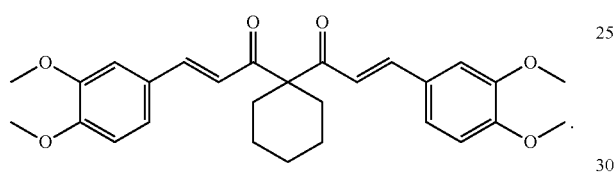

In some embodiments, a JAK inhibitor can be BMS-911543,

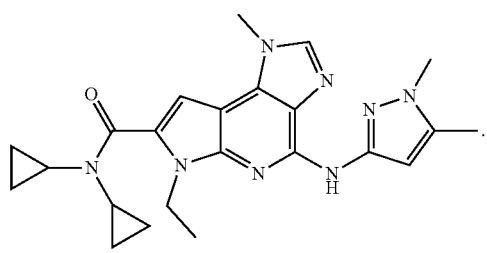 [SMILES: CCn1c(C(=O)N(C2CC2)C2CC2)cc2c3c(ncn3C)c(Nc3cc(C)n(C)n3)nc21]

In some embodiments, a JAK inhibitor can be peficitinib,

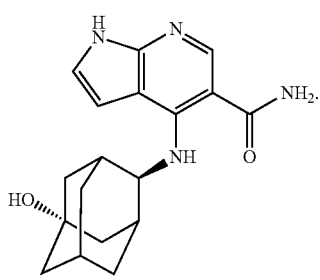 [SMILES: NC(=O)c1cnc2[nH]ccc2c1N[C@H]1C2CC3CC1C[C@](O)(C3)C2]

In some embodiments, a JAK inhibitor can be GLPG0634 analogue,

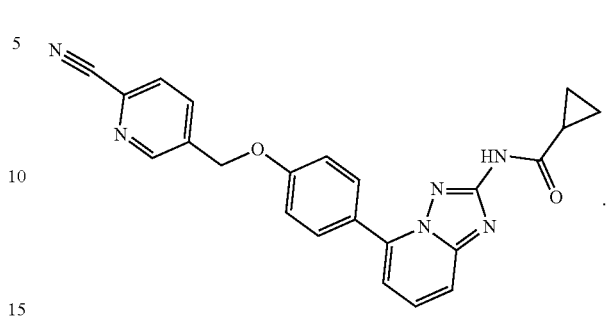

In some embodiments, a JAK inhibitor can be Go6976,

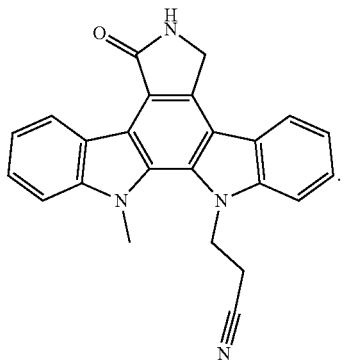 [SMILES: Cn1c2ccccc2c2c3c(c4c5ccccc5n(CCC#N)c4c21)CNC3=O]

In some embodiments, a JAK inhibitor can be Curcumol,

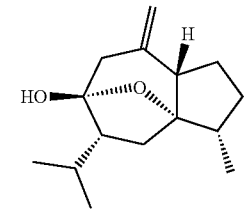

In some embodiments, a JAK inhibitor can be cucurbitacin,

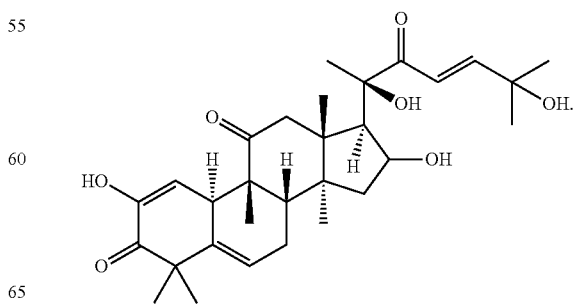

In some embodiments, a JAK inhibitor can be lestaurtinib,

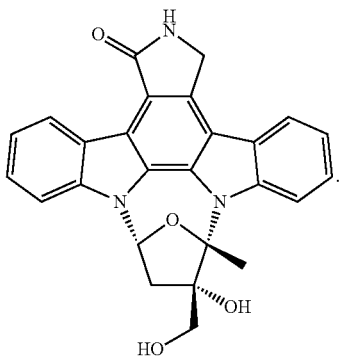 [SMILES: C[C@]12O[C@H](C[C@]1(O)CO)n1c3ccccc3c3c4c(c5c6ccccc6n2c5c31)CNC4=O]

In some embodiments, a JAK inhibitor can be upadacitinib,

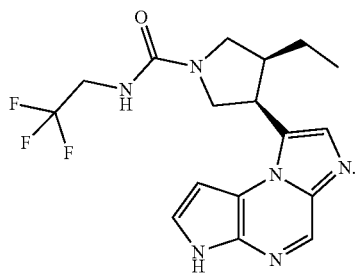 [SMILES: CC[C@@H]1CN(C(=O)NCC(F)(F)F)C[C@@H]1c1cnc2cnc3[nH]ccc3n12]

In some embodiments, a JAK inhibitor can be CHZ868,

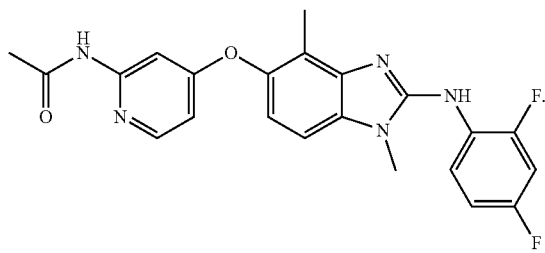 [SMILES: CC(=O)Nc1cc(Oc2ccc3c(nc(Nc4ccc(F)cc4F)n3C)c2C)ccn1]

In some embodiments, a JAK inhibitor can be Solcitinib (GSK 2586184),

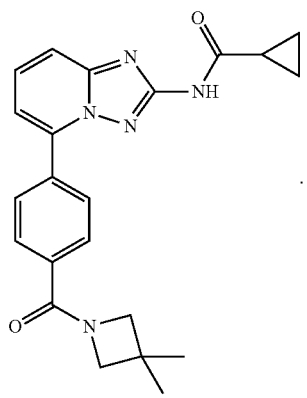 [SMILES: CC1(C)CN(C(=O)c2ccc(-c3cccc4nc(NC(=O)C5CC5)nn34)cc2)C1]

In some embodiments, a JAK inhibitor can be NS-018,

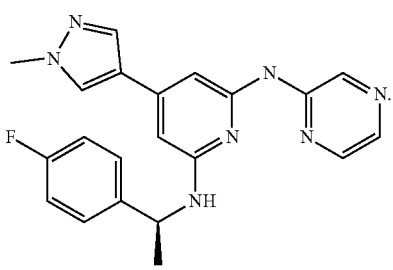 [SMILES: C[C@H](Nc1cc(-c2cnn(C)c2)cc(Nc2cnccn2)n1)c1ccc(F)cc1]

The term "imine" or "imino", as used herein, unless otherwise indicated, includes a functional group or chemical compound containing a carbon-nitrogen double bond. The expression "imino compound", as used herein, unless otherwise indicated, refers to a compound that includes an "imine" or an "imino" group as defined herein.

The term "hydroxyl", as used herein, unless otherwise indicated, includes —OH.

The terms "halogen" and "halo", as used herein, unless otherwise indicated, include a chlorine, chloro, Cl; fluorine, fluoro, F; bromine, bromo, Br; or iodine, iodo, or I.

The term "aryl", as used herein, unless otherwise indicated, include a carbocyclic aromatic group. Examples of aryl groups include, but are not limited to, phenyl, benzyl, naphthyl, or anthracenyl.

The terms "amine" and "amino", as used herein, unless otherwise indicated, include a functional group that contains a nitrogen atom with a lone pair of electrons and wherein one or more hydrogen atoms have been replaced by a substituent such as, but not limited to, an alkyl group or an aryl group.

The term "alkyl", as used herein, unless otherwise indicated, includes saturated monovalent hydrocarbon radicals having straight or branched moieties, such as but not limited to, methyl, ethyl, propyl, butyl, pentyl, hexyl, octyl groups, etc. Representative straight-chain lower alkyl groups include, but are not limited to, -methyl, -ethyl, -n-propyl, -n-butyl, -n-pentyl, -n-hexyl, -n-heptyl and -n-octyl; while branched lower alkyl groups include, but are not limited to, -isopropyl, -sec-butyl, -isobutyl, -tert-butyl, -isopentyl, 2-methylbutyl, 2-methylpentyl, 3-methylpentyl, 2,2-dimethylbutyl, 2,3-dimethylbutyl, 2,2-dimethylpentyl, 2,3-dimethylpentyl, 3,3-dimethylpentyl, 2,3,4-trimethylpentyl, 3-methylhexyl, 2,2-dimethylhexyl, 2,4-dimethylhexyl, 2,5-dimethylhexyl, 3,5-dimethylhexyl, 2,4-dimethylpentyl, 2-methylheptyl, 3-methylheptyl, unsaturated $C_1$-$C_8$ alkyls include, but are not limited to, -vinyl, -allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, 1-hexyl, 2-hexyl, 3-hexyl, -acetylenyl, -propynyl, -1-butynyl, -2-butynyl, -1-pentynyl, -2-pentynyl, or -3-methyl-1 butynyl. An alkyl can be saturated, partially saturated, or unsaturated.

The term "carboxyl", as used herein, unless otherwise indicated, includes a functional group consisting of a carbon atom double bonded to an oxygen atom and single bonded to a hydroxyl group (—COOH).

The term "alkenyl", as used herein, unless otherwise indicated, includes alkyl moieties having at least one carbon-carbon double bond wherein alkyl is as defined above and including E and Z isomers of said alkenyl moiety. An alkenyl can be partially saturated or unsaturated.

The term "alkynyl", as used herein, unless otherwise indicated, includes alkyl moieties having at least one carbon-carbon triple bond wherein alkyl is as defined above. An alkynyl can be partially saturated or unsaturated.

The term "acyl", as used herein, unless otherwise indicated, includes a functional group derived from an aliphatic carboxylic acid, by removal of the hydroxyl (—OH) group.

The term "alkoxyl", as used herein, unless otherwise indicated, includes O-alkyl groups wherein alkyl is as defined above and O represents oxygen. Representative alkoxyl groups include, but are not limited to, —O-methyl, —O-ethyl, —O-n-propyl, —O-n-butyl, —O-n-pentyl, —O-n-hexyl, —O-n-heptyl, —O-n-octyl, —O-isopropyl, —O-sec-butyl, —O-isobutyl, —O-tert-butyl, —O-isopentyl, —O-2-methylbutyl, —O-2-methylpentyl, —O-3-methylpentyl, —O-2,2-dimethylbutyl, —O-2,3-dimethylbutyl, —O-2,2-dimethylpentyl, —O-2,3-dimethylpentyl, —O-3,3-dimethylpentyl, —O-2,3,4-trimethylpentyl, —O-3-methylhexyl, —O-2,2-dimethylhexyl, —O-2,4-dimethylhexyl, —O-2,5-dimethylhexyl, —O-3,5-dimethylhexyl, —O-2,4dimethylpentyl, —O-2-methylheptyl, —O-3-methylheptyl, —O-vinyl, —O-allyl, —O-1-butenyl, —O-2-butenyl, —O-isobutylenyl, —O-1-pentenyl, —O-2-pentenyl, —O-3-methyl-1-butenyl, —O-2-methyl-2-butenyl, —O-2,3-dimethyl-2-butenyl, —O-1-hexyl, —O-2-hexyl, —O-3-hexyl, —O-acetylenyl, —O-propynyl, —O-1-butynyl, —O-2-butynyl, —O-1-pentynyl, —O-2-pentynyl and —O-3-methyl-1-butynyl, —O-cyclopropyl, —O-cyclobutyl, —O-cyclopentyl, —O-cyclohexyl, —O-cycloheptyl, —O-cyclooctyl, —O-cyclononyl and —O-cyclodecyl, —O—CH$_2$-cyclopropyl, —O—CH$_2$-cyclobutyl, —O—CH$_2$-cyclopentyl, —O—CH$_2$-cyclohexyl, —O—CH$_2$-cycloheptyl, —O—CH$_2$-cyclooctyl, —O—CH$_2$-cyclononyl, —O—CH$_2$-cyclodecyl, —O—(CH$_2$)$_2$-cyclopropyl, —O—(CH$_2$)$_2$-cyclobutyl, —O—(CH$_2$)$_2$-cyclopentyl, —O—(CH$_2$)$_2$-cyclohexyl, —O—(CH$_2$)$_2$-cycloheptyl, —O—(CH$_2$)$_2$-cyclooctyl, —O—(CH$_2$)$_2$-cyclononyl, or —O—(CH$_2$)$_2$-cyclodecyl. An alkoxyl can be saturated, partially saturated, or unsaturated.

The term "cycloalkyl", as used herein, unless otherwise indicated, includes a non-aromatic, saturated, partially saturated, or unsaturated, monocyclic or fused, spiro or unfused bicyclic or tricyclic hydrocarbon referred to herein containing a total of from 3 to 10 carbon atoms, preferably 3 to 8 ring carbon atoms. Examples of cycloalkyls include, but are not limited to, C$_3$-C$_8$ cycloalkyl groups include, but are not limited to, -cyclopropyl, -cyclobutyl, -cyclopentyl, -cyclopentadienyl, -cyclohexyl, -cyclohexenyl, -1,3-cyclohexadienyl, -1,4-cyclohexadienyl, -cycloheptyl, -1,3-cycloheptadienyl, -1,3,5-cycloheptatrienyl, -cyclooctyl, and -cyclooctadienyl.

The term "cycloalkyl" also includes -lower alkyl-cycloalkyl, wherein lower alkyl and cycloalkyl are as defined herein. Examples of -lower alkyl-cycloalkyl groups include, but are not limited to, —CH$_2$-cyclopropyl, —CH$_2$-cyclobutyl, —CH$_2$-cyclopentyl, —CH$_2$-cyclopentadienyl, —CH$_2$-cyclohexyl, —CH$_2$-cycloheptyl, or —CH$_2$-cyclooctyl.

The term "heterocyclic", as used herein, unless otherwise indicated, includes an aromatic or non-aromatic cycloalkyl in which one to four of the ring carbon atoms are independently replaced with a heteroatom from the group consisting of 0, S and N. Representative examples of a heterocycle include, but are not limited to, benzofuranyl, benzothiophene, indolyl, benzopyrazolyl, coumarinyl, isoquinolinyl, pyrrolyl, pyrrolidinyl, thiophenyl, furanyl, thiazolyl, imidazolyl, pyrazolyl, triazolyl, quinolinyl, pyrimidinyl, pyridinyl, pyridonyl, pyrazinyl,pyridazinyl, isothiazolyl, isoxazolyl, (1,4)-dioxane, (1,3)-dioxolane, 4,5-dihydro-1H-imidazolyl, or tetrazolyl. Heterocycles can be substituted or unsubstituted. Heterocycles can also be bonded at any ring atom (i.e., at any carbon atom or heteroatom of the heterocyclic ring). A heterocyclic can be saturated, partially saturated, or unsaturated.

The term "cyano", as used herein, unless otherwise indicated, includes a —CN group.

The term "alcohol", as used herein, unless otherwise indicated, includes a compound in which the hydroxyl functional group (—OH) is bound to a carbon atom. In particular, this carbon center should be saturated, having single bonds to three other atoms.

When carbocyclyl and heterocyclyl are substituted, they are typically substituted by 1 or 2 substituents (e.g. 1 substituent). Typically the substituent is methyl. More typically carbocyclyl and heterocyclyl groups are unsubstituted.

When aryl and heteroaryl are substituted, they are typically substituted by 1, 2 or 3 (e.g. 1 or 2) substituents. Substituents for aryl and heteroaryl are selected from C$_{1-6}$alkyl (e.g. methyl), C$_{2-6}$alkenyl (e.g. buten-3-yl), C$_{2-6}$alkynyl (e.g. butyn-3-yl), C$_{1-6}$haloalkyl (e.g. fluoromethyl, trifluoromethyl), —C$_{1-6}$thioalkyl (e.g. —S-methyl), —SOC$_{1-4}$alkyl (e.g. —SOmethyl), —SO$_2$C$_{1-4}$alkyl (e.g. —SO$_2$methyl), C$_{1-6}$alkoxy- (e.g. methoxy, ethoxy), —O—C$_{3-8}$cycloalkyl (e.g. —O-cyclopentyl), C$_{3-8}$cycloalkyl (e.g. cyclopropyl, cyclohexyl), —SO$_2$C$_{3-8}$cycloalkyl (e.g. —SO$_2$cyclohexyl), —SOC$_{3-6}$cycloalkyl (e.g. —SOcyclopropyl), C$_{3-6}$alkenyloxy- (e.g. —O-buten-2-yl), C$_{3-6}$alkynyloxy- (e.g. —O-buten-2-yl), —C(O)C$_{1-6}$alkyl (e.g. —C(O)ethyl), —C(O)OC$_{1-6}$alkyl (e.g. —C(O)O-methyl), C$_{1-6}$alkoxy-C$_{1-6}$alkyl- (e.g. methoxy-ethyl-), nitro, halogen (e.g. fluoro, chloro, bromo), cyano, hydroxyl, —C(O)OH, —NH$_2$, —NHC$_{1-4}$alkyl (e.g. —NHmethyl), —N(C$_{1-4}$alkyl)(C$_{1-4}$alkyl) (e.g. —N(methyl)$_2$), —C(O)N(C$_{1-4}$alkyl)(C$_{1-4}$alkyl) (e.g. —C(O)N(methyl)$_2$), —C(O)NH$_2$, —C(O)NH(C$_{1-4}$alkyl) (e.g. —C(O)NHmethyl), —C(O)NH(C$_{3-10}$cycloalkyl) (e.g. —C(O)NHcyclopropyl). More typically, substituents will be selected from C$_{1-6}$alkyl (e.g. methyl), C$_{1-6}$haloalkyl (e.g. C$_{1-6}$fluoroalkyl, e.g. CF$_3$), C$_{1-6}$alkoxy (e.g. OMe), halogen and hydroxy.

When an R group represents heteroaryl, examples include monocyclic (e.g. 5 and 6 membered) and bicyclic (e.g. 9 and 10 membered, particularly 9 membered) heteroaryl rings, especially rings containing nitrogen atoms (e.g. 1 or 2 nitrogen atoms). A suitable bicyclic heteroaryl ring is a 9-membered heteroaryl ring containing 1 or 2 nitrogen atoms, especially a benzene ring fused to a 5-membered ring containing one or two nitrogen atoms (e.g. 1H-benzoimidazolyl). Most suitably the point of attachment is through a benzene ring, e.g. the group is 1H-benzoimidazol-5-yl. Aforementioned heteroaryl groups may either be unsubstituted (which is more typical) or may suitably be substituted by one or more (e.g. 1 or 2) substituents selected from alkyl (e.g. C$_{1-4}$ alkyl such as Me), alkoxy- (e.g. C$_{1-4}$ alkoxy- such as OMe) and halogen (e.g. F).

When an R group represents —C$_{3-8}$carbocyclyl-heteroaryl, examples of carbocyclyl include cycloalkyl (e.g. cyclohexyl) and cycloalkenyl (e.g. cyclohexenyl), examples of heteroaryl groups include monocyclic (e.g. 5 or 6 membered, particularly 5 membered) rings especially rings containing nitrogen atoms e.g. 1 or 2 nitrogen atoms. Aforementioned heteroaryl groups may either be unsubstituted (which is more typical) or may suitably be substituted by one or more (e.g. 1 or 2) substituents selected from alkyl (e.g. C$_{1-4}$ alkyl such as Me), alkoxy- (e.g. C$_{1-4}$ alkoxy- such as OMe) and halogen (e.g. F). A suitable heteroaryl group is imidazol-1-yl. An exemplary —C$_{3-8}$carbocyclyl-heteroaryl group is 3-imidazol-1-yl-cyclohexyl-.

When an R group represents —C$_{2-6}$alkenyheteroaryl, examples of C$_{2-6}$ alkenyl include C$_{2-4}$ alkenyl, in particular propenyl and examples of heteroaryl groups include monocyclic (e.g. 5 or 6 membered, particularly 5 membered) rings especially rings containing nitrogen atoms e.g. 1 or 2 nitrogen atoms. Aforementioned heteroaryl groups may either be unsubstituted (which is more typical) or may suitably be substituted by one or more (e.g. 1 or 2) substituents selected from alkyl (e.g. C$_{1-4}$alkyl such as Me), alkoxy- (e.g. C$_{1-4}$ alkoxy- such as OMe) and halogen (e.g. F). A suitable heteroaryl group is imidazolyl, particularly imidazol-1-yl. An exemplary -alkenylheteroaryl group is 3-imidazol-1-yl-prop-2-enyl-.

When an R group represents —C$_{1-6}$alkylheteroaryl, examples of C$_{1-6}$ alkyl include C$_{1-5}$alkyl or C$_{1-4}$alkyl, especially C$_{2-5}$alkyl or C$_{2-4}$ alkyl, in particular propyl, and examples of heteroaryl groups include monocyclic (e.g. 5 or 6 membered, particularly 5 membered) rings especially rings containing nitrogen atoms e.g. 1 or 2 nitrogen atoms. Aforementioned heteroaryl groups may either be unsubstituted (which is most typical) or may suitably be substituted by one or more (e.g. 1 or 2) substituents selected from alkyl (e.g. C$_{1-4}$ alkyl such as Me), alkoxy- (e.g. C$_{1-4}$ alkoxy- such as OMe) and halogen (e.g. F). A suitable heteroaryl group is imidazol-1-yl. A particularly suitable -alkylheteroaryl group is 3-imidazol-1-yl-propyl-.

When R represents —C$_{1-6}$alkylheteroaryl, examples wherein alkyl is branched include:

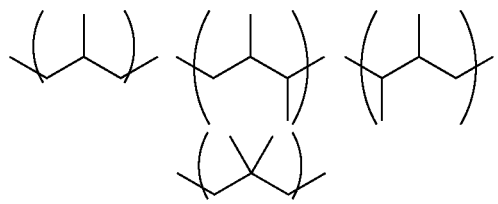

When an R group represents (CH$_2$)$_a$CR$^5$R$^6$(CH$_2$)$_b$heteroaryl wherein a and b independently represent integers 0-5 provided that a+b=0-5 and R$^5$ and R$^6$ are alkylene which together with the carbon to which they are attached form a C$_3$-C$_5$ cycloalkyl group, examples include:

Particular examples of R heteroaryl groups include a 5-membered ring containing 2 or 3 nitrogen atoms, which ring may optionally be substituted (e.g. in particular by one or two groups, such as methyl, for example:

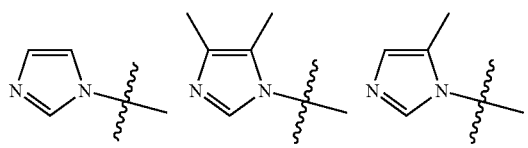

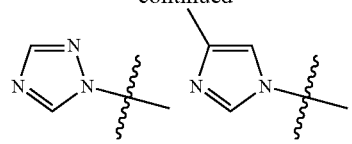

Other examples of R heteroaryl groups include a 9-membered bicyclic ring containing 2 nitrogen atoms, which ring may optionally be substituted, for example:

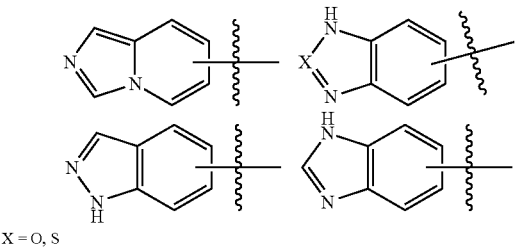

X = O, S

Clearly, the heteroaryl groups shown above may also be present as part of a larger R function such as —C$_{3-8}$carbocyclyl-heteroaryl, —C$_{2-6}$alkenylheteroaryl or —C$_{1-6}$alkylheteroaryl.

When an R group represents —C$_{1-8}$alkyl, examples include methyl, ethyl, propyl (e.g. n-propyl, isopropyl), butyl (e.g. n-butyl-sec-butyl, isobutyl and tert-butyl), pentyl (e.g. n-pentyl, 3,3,-dimethylpropyl), hexyl, heptyl and octyl.

When an R group represents optionally substituted aryl, aryl may typically represent phenyl. Exemplary substituted phenyl groups include 3-methylphenyl-, 2,3-dichlorophenyl-, 2,3-difluorophenyl-, 2,4-dichlorophenyl-, 2,4-difluorophenyl-, 2,4-dimethoxyphenyl-, 2,4-dimethylphenyl-, 2,4-bis(trifluoromethyl)phenyl-, 2,4,6-trifluorophenyl-, 2,4,6-trimethylphenyl-, 2,6-dichlorophenyl-, 2,6-difluorophenyl-, 2,6-dimethoxyphenyl-, 2,6-difluoro-4-(methoxy)phenyl-, 2-isopropyl-6-methylphenyl-, 3-(cyclopentyloxy)-4-methoxyphenyl-, 3,4,5-trimethoxyphenyl-, 3,4-dimethoxyphenyl-, 3,4-dichlorophenyl-, 3,4-difluorophenyl-, 3,4-dimethylphenyl-, 3,4,5-trifluorophenyl-, 3,5-bis (trifluororomethyl)phenyl-, 3,5-dimethoxyphenyl-, 2-methoxyphenyl-, 3-methoxyphenyl-, 4-(trifluoromethyl) phenyl-, 4-bromo-2-(trifluoromethyl)phenyl-, 4-bromophenyl-, 4-chloro-3-(trifluoromethyl)phenyl-, 4-chlorophenyl-, 4-cyanophenyl-, 4-ethoxyphenyl-, 4-ethylphenyl-, 4-fluorophenyl-, 4-isopropylphenyl-, 4-methoxyphenyl-, 4-ethoxyphenyl-, 4-propoxyphenyl-, 4-butoxyphenyl-, 4-pentoxyphenyl-, 4-isopropyloxyphenyl-, 4-tetrafluoroethyloxyphenyl-. Alternatively, R$^2$ may represent unsubstituted phenyl-. Further exemplary substituted phenyl groups include 2,3,4-trifluorophenyl, 2,3-difluoro-4-methylphenyl, 2-bromo-4-fluorophenyl-, 2-bromo-5-fluorophenyl-, 2-chlorophenyl-, 2-fluorophenyl-, 2-fluoro-5-(trifluoromethyl)phenyl-, 2-hydroxy-3-methoxyphenyl-, 2-hydroxy-5-methylphenyl-, 3-chlorophenyl-, 3-fluorophenyl-, 3-fluoro-4-(trifluoromethyl)phenyl-, 3-fluoro-5-(trifluoromethyl)phenyl-, 2-fluoro-4-(trifluoromethyl)phenyl-, 3-fluoro-4-(methoxy)phenyl-, 3-hydroxy-4-methoxyphenyl-, 4-bromo-2-fluorophenyl, 4-chloro-3-(trifluoromethyl) phenyl-, 4-chloro-3-methylphenyl, 4-chlorophenyl-, 4-fluorophenyl- and 4-propoxyphenyl-.

When an R group represents optionally substituted aryl and aryl represents naphthyl, examples include unsubstituted naphthyl (e.g. naphthalen-1-yl, naphthalen-2-yl, naphthalen-3-yl) as well as substituted naphthyl (e.g. 4-methyl-naphthalen-2-yl-, 5-methyl-naphthalen-3-yl-, 7-methyl-naphthalen-3-y- and 4-fluoro-naphthalen-2-yl-).

When an R group represents optionally substituted heteroaryl, examples include monocyclic rings (e.g. 5 or 6 membered rings) and bicyclic rings (e.g. 9 or 10 membered rings) which may optionally be substituted. Example 5 membered rings include pyrrolyl (e.g. pyrrol-2-yl) and imidazolyl (e.g. 1H-imidazol-2-yl or 1H-imidazol-4-yl), pyrazolyl (e.g. 1H-pyrazol-3-yl), furanyl (e.g. furan-2-yl), thiazolyl (e.g. thiazol-2-yl), thiophenyl (e.g. thiophen-2-yl, thiophen-3-yl). Example 6 membered rings include pyridinyl (e.g. pyridin-2-yl and pyridin-4-yl). Specific substituents that may be mentioned are one or more e.g. 1, 2 or 3 groups selected from halogen, hydroxyl, alkyl (e.g. methyl) and alkoxy- (e.g. methoxy-). Example substituted 5 membered rings include 4,5-dimethyl-furan-2-yl-, 5-hydroxymethyl-furan-2-yl-, 5-methyl-furan-2-yl- and 6-methyl-pyridin-2-yl-. An example substituted 6-membered ring is 1-oxy-pyridin-4-yl-. Example 9 membered rings include 1H-indolyl (e.g. 1H-indol-3-yl, 1H-indol-5-yl), benzothiophenyl (e.g. benzo[b]thiophen-3-yl, particularly 2-benzo[b]thiophen-3-yl), benzo[1,2,5]-oxadiazolyl(e.g. benzo[1,2,5]-oxadiazol-5-yl), benzo[1,2,5]-thiadiazolyl(e.g. benzo[1,2,5]-thiadiazol-5-yl, benzo[1,2,5]thiadiazol-6-yl). Example 10 membered rings include quinolinyl (e.g. quinolin-3-yl, quinolin-4-yl, quinolin-8-yl). Specific substituents that may be mentioned are one or more e.g. 1, 2 or 3 groups selected from halogen, hydroxyl, alkyl (e.g. methyl) and alkoxy- (e.g. methoxy-). Example substituted 9-membered rings include 1-methyl-1H-indol-3-yl, 2-methyl-1H-indol-3-yl, 6-methyl-1H-indol-3-yl. Example substituted 10 membered rings include 2-chloro-quinolin-3-yl, 8-hydroxy-quinolin-2-yl, oxo-chromenyl (e.g. 4-oxo-4H-chromen-3-yl) and 6-methyl-4-oxo-4H-chromen-3-yl.

When an R group represents carbocyclyl, examples include cycloalkyl and cycloalkenyl. Examples of cycloalkyl include cyclopropyl, cyclobutyl, cyclopentyl, cyclohexyl and cycloheptyl. Examples of cycloalkenyl include cyclohexenyl (e.g. cyclohex-2-enyl, cyclohex-3-enyl). Examples of substituted carbocyclyl include 2-methyl-cyclohexyl-, 3-methyl-cyclohexyl-, 4-methyl-cyclohexyl-, 2-methyl-cyclohex-2-enyl, 2-methyl-cyclohex-3-enyl, 3-methyl-cyclohex-3-enyl, 3-methyl-cyclohex-3-enyl.

When an R group represents heterocyclyl (which may optionally be substituted), examples include tetrahydrofuranyl, morpholinyl, piperdinyl, 3,4-dihydro-2H-pyranyl, pyrrolidinyl, methyltetrahydrofuranyl- (e.g. 5-methyltetrahydrofuran-2-yl-).

When an R group represents $—C_{1-4}$alkylaryl, examples include -alkyl(substituted phenyl) e.g. in which phenyl is substituted by one or more groups selected from alkyl, fluoroalkyl, halogen and alkoxy (e.g. methyl, trifluoromethyl, tert-butyl, chloro, fluoro and methoxy) and, for example, alkyl is $C_{1-4}$ alkyl. Another specific group is -alkyl(bicyclic aryl) e.g. wherein bicyclic aryl is optionally substituted naphthyl. A further specific group is benzyl.

When an R group represents $—C_{1-4}$alkylheteroaryl in which heteroaryl is optionally substituted, examples include methylheteroaryl and -ethylheteroaryl (e.g. 1-heteroarylethyl- and 2-heteroarylethyl-), -propylheteroaryl and -butylheteroaryl in which heteroaryl is optionally substituted. Specific examples of -alkylheteroaryl groups include pyridinylmethyl-, N-methyl-pyrrol-2-methyl-N-methyl-pyrrol-2-ethyl-, N-methyl-pyrrol-3-methyl-, N-methyl-pyrrol-3-ethyl-, 2-methyl-pyrrol-1-methyl-, 2-methyl-pyrrol-1-ethyl-, 3-methyl-pyrrol-1-methyl-, 3-methyl-pyrrol-1-ethyl-, 4-pyridino-methyl-, 4-pyridino-ethyl-, 2-(thiazol-2-yl)-ethyl-, 2-ethyl-indol-1-methyl-, 2-ethyl-indol-1-ethyl-, 3-ethyl-indol-1-methyl-, 3-ethyl-indol-1-ethyl-, 4-methyl-pyridin-2-methyl-, 4-methyl-pyridin-2-yl-ethyl-, 4-methyl-pyridin-3-methyl-, 4-methyl-pyridin-3-ethyl-.

When an R group represents $—C_{1-4}$alkyl-carbocyclyl (which may optionally be substituted), examples include -methyl-cyclopentyl, -methyl-cyclohexyl, -ethyl-cyclohexyl, -propyl-cyclohexyl, -methyl-cyclohexenyl, -ethyl-cyclohexenyl, -methyl(4-methylcyclohexyl) and -propyl (3-methylcyclyohexyl).

When an R group represents $—C_{1-4}$alkylheterocyclyl (which may optionally be substituted); examples include -methyl-tetrahydrofuranyl (e.g. -methyl-tetrahydrofuran-2-yl, -methyl-tetrahydrofuran-3-yl), -ethyl-tetrahydrofuranyl, -methyl-piperidinyl.

When an R group represents phenyl substituted by phenyl or phenyl substituted by a monocyclic heteroaryl group, in which any of aforesaid phenyl and heteroaryl groups may optionally be substituted, typically the phenyl ring connected directly to the nitrogen atom is unsubstituted and the terminal phenyl ring or the monocyclic heteroaryl ring is optionally substituted by one, two or three substitutents (e.g. one or two, e.g. one). Typically the terminal phenyl or monocyclic heteroaryl group is unsubstituted. Typically the terminal phenyl or monocyclic heteroaryl group substitutes the other phenyl group at the 4-position.

When an R group represents phenyl substituted by phenyl in which any of aforesaid phenyl groups may optionally be substituted, examples include -biphenyl-4-yl.

When an R group represents phenyl substituted by a monocyclic heteroaryl group, in which any of aforesaid phenyl and heteroaryl groups may optionally be substituted, examples include 4-(oxazol-5-yl)phenyl-.

When an R group represents phenyl substituted by benzyloxy in which any of aforesaid phenyl and benzyloxy groups may optionally be substituted, examples include 4-benzyloxy-phenyl-, 4-(3-methylbenzyloxy)phenyl- and 4-(4-methylbenzyloxy)phenyl-.

When an R group represents optionally substituted phenyl fused to optionally substituted carbocyclyl, examples include indanyl (e.g. indan-4-yl-, 2-methyl-indan-4-yl-), indenyl and tetralinyl.

When an R group represents optionally substituted phenyl fused to optionally substituted heterocyclyl, examples include benzo[1,3]dioxo-4-yl- and 2,3-dihydro-benzo[1,4]dioxin-4-yl-.

When an R group represents $—C_{1-4}$alkyl(phenyl substituted by phenyl), examples include biphenyl-4-yl-methyl-.

When an R group represents $—C_{1-4}$alkyl(phenyl substituted by a monocyclic heteroaryl group), examples include 4-(oxazol-5-yl)phenyl-methyl-.

When an R group represents $—C_{1-4}$alkyl(phenyl substituted by benzyloxy) in which any of aforesaid phenyl and benzyloxy groups may optionally be substituted, examples include 4-benzyloxy-phenyl-methyl-, 4-(3-methylbenzyloxy)phenyl-methyl- and 4-(4-methylbenzyloxy)phenyl-methyl-.

When an R group represents $—C_{1-4}$alkyl(optionally substituted phenyl fused to optionally substituted carbocyclyl), examples include indanyl-methyl- (e.g. indan-4-yl-methyl-, 2-methyl-indan-4-yl-methyl-), indenyl-methyl- and tetralinyl-methyl-.

When an R group represents $—C_{1-4}$alkyl(optionally substituted phenyl fused to optionally substituted heterocyclyl);

examples include benzo[1,3]dioxo-4-yl-methyl- and 2,3-dihydro-benzo[1,4]dioxin-4-yl-methyl-.

When an R group represents —$C_{1-4}$alkyl, examples include methyl, ethyl, propyl (e.g. n-propyl, isopropyl) and butyl (e.g. n-butyl-sec-butyl, isobutyl and tert-butyl).

When an R group represents optionally substituted aryl, aryl may typically represent phenyl. Exemplary substituted phenyl groups include 2,4-dichlorophenyl-, 2,4-difluororophenyl-, 2,4-dimethoxyphenyl-, 2,4-dimethylphenyl-, 2,4-bis(trifluoromethyl)phenyl-, 2,4,6-trifluorophenyl-, 2,4,6-trimethylphenyl-, 2,6-dichlorophenyl-, 2,6-difluorophenyl-, 2,6-dimethoxyphenyl-, 2-isopropyl-6-methylphenyl-, 3-(cyclopentyloxy)-4-methoxyphenyl-, 3,4,5-trimethoxyphenyl-, 3,4-dimethoxyphenyl-, 3,4-dichlorophenyl-, 3,4-dimethylphenyl-, 3,4,5-trifluorophenyl-, 3,5-bis(trifluororomethyl) phenyl-, 3,5-dimethoxyphenyl-, 3-methoxyphenyl-, 4-(trifluoromethyl)phenyl-, 4-bromo-2-(trifluoromethyl)phenyl-, 4-bromophenyl-, 4-chloro-3-(trifluoromethyl)phenyl-, 4-chlorophenyl-, 4-cyanophenyl-, 4-ethoxyphenyl-, 4-ethylphenyl-, 4-fluorophenyl-, 4-isopropylphenyl-, 4-methoxyphenyl-. Alternatively, $R^3$ may represents unsubstituted phenyl-. Further exemplary substituted phenyl groups include 2-bromo-4-fluorophenyl-, 2-bromo-5-fluorophenyl-, 2-chlorophenyl-, 2-fluoro-5-(trifluoromethyl)phenyl-, 2-hydroxy-3-methoxyphenyl-, 2-hydroxy-5-methylphenyl-, 3-chloro-phenyl-, 3-fluoro-4-(trifluoromethyl)phenyl-, 3-hydroxy-4-methoxyphenyl-, 4-chloro-3-(trifluoromethyl)phenyl-, 4-chlorophenyl-, 4-fluorophenyl- and 4-propoxyphenyl-.

When $R^1$ and $R^2$ or $R^3$ and $R^4$ are joined to form a carbocyclyl ring, which is optionally substituted by one or more $C_{1-2}$alkyl groups, examples include cycloalkyl (e.g. cyclopropyl, cyclopentyl and cyclohexyl) and cycloalkenyl (e.g. cyclohexenyl).

When $R^1$ and $R^2$ or $R^3$ and $R^4$ are joined to form a carbocyclyl ring which is fused to phenyl; examples include indanyl (e.g. indan-2-yl) and tetralinyl.

When $R^1$ and $R^2$ or $R^3$ and $R^4$ are joined to form a carbocyclyl ring which is fused to monocyclic heteroaryl; examples include 5-membered carbocyclyl fused to 6-membered heteroaryl, 6-membered carbocyclyl fused to 6-membered heteroaryl, 5-membered carbocyclyl fused to 5-membered heteroaryl and 6-membered carbocyclyl fused to 5-membered heteroaryl. The monocyclic heteroaryl to which carbocyclyl is fused contains at least one heteroatom (e.g. one, two or three heteroatoms, e.g. one or two, e.g. one heteroatom).

When an R group represents —$C_{1-8}$alkyl examples include methyl, ethyl, propyl (e.g. n-propyl, isopropyl), butyl (e.g. n-butyl-sec-butyl, isobutyl and tert-butyl), pentyl (e.g. n-pentyl, 3,3,-dimethylpropyl), hexyl, heptyl and octyl.

When an R group represents —C(O)$C_{1-6}$alkyl; examples include —C(O)$C_{1-4}$alkyl such as —C(O)methyl, —C(O)ethyl, —C(O)propyl and —C(O)butyl.

The term "solvate" is intended to mean a solvate form of a specified compound that retains the effectiveness of such compound. Examples of solvates include compounds of the invention in combination with, for example: water, isopropanol, ethanol, methanol, dimethylsulfoxide (DMSO), ethyl acetate, acetic acid, or ethanolamine.

The term "mmol", as used herein, is intended to mean millimole. The term "equiv", as used herein, is intended to mean equivalent. The term "mL", as used herein, is intended to mean milliliter. The term "g", as used herein, is intended to mean gram. The term "kg", as used herein, is intended to mean kilogram. The term "µg", as used herein, is intended to mean micrograms. The term "h", as used herein, is intended to mean hour. The term "min", as used herein, is intended to mean minute. The term "M", as used herein, is intended to mean molar. The term "µL", as used herein, is intended to mean microliter. The term "µM", as used herein, is intended to mean micromolar. The term "nM", as used herein, is intended to mean nanomolar. The term "N", as used herein, is intended to mean normal. The term "amu", as used herein, is intended to mean atomic mass unit. The term "° C.", as used herein, is intended to mean degree Celsius. The term "wt/wt", as used herein, is intended to mean weight/weight. The term "v/v", as used herein, is intended to mean volume/volume. The term "MS", as used herein, is intended to mean mass spectroscopy. The term "HPLC", as used herein, is intended to mean high performance liquid chromatograph. The term "RT", as used herein, is intended to mean room temperature. The term "e.g.", as used herein, is intended to mean example. The term "N/A", as used herein, is intended to mean not tested.

As used herein, the expression "pharmaceutically acceptable salt" refers to pharmaceutically acceptable organic or inorganic salts of a compound of the invention. Preferred salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, or pamoate (i.e., 1,1'-methylene-bis-(2-hydroxy-3-naphthoate)) salts. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counterions. Hence, a pharmaceutically acceptable salt can have one or more charged atoms and/or one or more counterion. As used herein, the expression "pharmaceutically acceptable solvate" refers to an association of one or more solvent molecules and a compound of the invention. Examples of solvents that form pharmaceutically acceptable solvates include, but are not limited to, water, isopropanol, ethanol, methanol, DMSO, ethyl acetate, acetic acid, and ethanolamine. As used herein, the expression "pharmaceutically acceptable hydrate" refers to a compound of the invention, or a salt thereof, that further includes a stoichiometric or non-stoichiometric amount of water bound by non-covalent intermolecular forces.

Pruritus and Conditions Associated with Pruritus

JAK inhibitors, as described herein, can treat pruritus and conditions associated with pruritus as a symptom. Pruritus can be referred to as the sensation that produces the desire to scratch. As described herein, it is shown that patients with recalcitrant chronic itch markedly improve when treated with JAK inhibitors.

As used herein, the terms "pruritus" and "itch" can be interchangeable.

TABLE 1, below, provides a summary of common diseases or conditions associated with pruritus as a major symptom. When the origin of pruritus cannot be identified (i.e., is not due to a known disease, see e.g., TABLE 1), the condition is referred to as idiopathic pruritus.

TABLE 1

Common diseases with pruritus as a major symptom

| GENERAL CATEGORY | SPECIFIC DISEASE | |
|---|---|---|
| Infestations, bites and stings | Scabies Pediculosis | Arthropod bites |
| Inflammation | Atopic dermatitis | Papular uritcaria |
| | Stasis dermatitis | Drug eruptions |
| | Allergic > irritant contact dermatitis | Bullous diseases Mastocytosis |
| | Seborrheic dermatitis | Eosinophilic |
| | Psoriasis | folliculitis |
| | Lichen planus Urticaria | Pruritic popular eruption of HIV |
| Autoimmune connective tissue disease | Scabies Lichen sclerosus Dermatomyositis | Scabies Lupus erythematosus |
| Infection | Bacterial Viral | Fungal Parasitic |
| Neoplastic | Cutaneous T-cell lymphoma Polycythemia vera | |

Chronic Pruritus and Chronic Idiopathic Pruritus

"Chronic pruritus" can be pruritus lasting longer than six weeks. Chronic idiopathic pruritus" or "CIP" refers to itch of unknown origin lasting greater than six weeks. Because the itch is of unknown origin, a subject with chronic idiopathic pruritus does not have a disease listed in TABLE 1. Subjects diagnosed with chronic idiopathic pruritus do not have the overt skin inflammation seen in other inflammatory pruritic diseases, such as atopic dermatitis. The initial evaluation of a patient who has chronic idiopathic pruritus typically includes a complete blood count with a differential count, a chest radiograph, and tests of hepatic, renal, and thyroid function. In many cases, subjects diagnosed with chronic idiopathic pruritus have pruritus despite two or more treatments over a period of at least six weeks. Examples of treatments may include, but are not limited to, the use of mild cleaners, emollients, topical anesthetics, coolants, antihistamines, anticonvulsants, antidepressants, µ-opioid antagonists, neuroactive medications (e.g. gabapentin, pregabalin, etc.), cortitcosteroid, and phototherapy.

Conditions associated with pruritus, treatable by JAK inhibitors, can be a disease or conditions wherein a symptom is pruritus. For example, a disease or condition associated with chronic idiopathic pruritus can be any of those diseases or conditions known by a person of ordinary skill in the art as being associated with the pruritus. As used herein, the terms "symptom" and "clinical sign" can be interchangeable. Symptoms can include those observable or measurable conditions or behaviors that are measured in known or established diagnostic assessments. For example, diagnostic assessments for a determination of pruritus can be made by a Numerical Rating Scale (NRS) score, Visual Analog Scale (VAS) score, or an Itch-Free Days (IFD) score, or by a scoring system such as the Eppendorf Itch Questionnaire or the Patient Benefit Index, Version for Patients with Pruritus (PBI-P), or the 5-D Itch Scale. Non-limiting examples of some symptoms of chronic idiopathic pruritus, that may be used in such assessments or scoring systems, include: quality of life or itching (e.g., distribution, duration, degree, improvement/worsening, impact on sleep, leisure, social, housework, errands, work/school, etc.). Itching may be reported as ranging from extremely severe (e.g., 9.0-10.0 using the VAS), to severe (e.g., 7.0-8.9 using the VAS), to moderate (e.g., 3.0-6.9 using the VAS), to mild (e.g.; 0.1-2.9 using the VAS).

One aspect of the present disclosure provides a subject in need of treatment for chronic idiopathic pruritus (CIP). In some embodiments, a subject in need of treatment for CIP is a subject diagnosed with CIP. Subjects diagnosed with CIP have pruritus of unknown origin that has lasted for at least six weeks. For example, the pruritus has lasted for at least six, at least seven, at least eight, at least nine, at least ten, at least eleven, or at least twelve weeks. The subject may have extremely severe itching, severe itching, moderate itching or mild itching. In other embodiments, a subject in need of treatment for CIP is a subject predisposed to CIP. For example, a subject may be predisposed to CIP if the subject was previously treated for CIP and the pruritus was resolved. The subject may have had extremely severe itching, severe itching, moderate itching or mild itching. Contemplated herein is the treatment of subjects of any age.

In some of the above embodiments, a subject in need of treatment for CIP may have immunologic deficits associated with Th2 polarization including, but not limited to, elevated serum IgE levels, peripheral eosinophilia, tissue eosinophil infiltration, CD8 lympohpenia, or any combination thereof. The subject may be ≥50 years of age, ≥55 years of age, ≥60 years of age, or ≥65 years of age. Alternatively, the subject may be ≤50 years of age.

Conditions associated with pruritus and treatable with JAK inhibitors can include, but are not limited to allergic reaction, arthropod bites, athlete's foot, atopic dermatitis (AD), atopic itch, atopic dermatitis-associated itch, autoimmune connective tissue disease, bacterial infection, biliary itch, broad activation of immune responses, body louse, bullous diseases, brachioradial pruritus, brain tumors, chronic idiopathic pruritus, contact dermatitis, cholestasis, cutaneous larva migrans, cutaneous T-cell lymphoma, damage of the nervous system, dandruff, delusional parasitosis, dermatomyositis, dermatosis of pregnancy, diabetes mellitus, drug eruptions, dysregulation of neuronal processes and sensory perception, eczema, eosinophilic folliculitis, foreign objects or devices on skin, fungal infection, gestational pemphigoid, head lice, herpes, hidradenitis suppurativa, hives, Hodgkin's disease, hyperparathyroidism, idiopathic chronic itch, inflammation, insect infestation, insect bites, insect stings, intrahepatic cholestasis of pregnancy, iron deficiency anemia, increased accumulation of exogenous opioids or synthetic opioids, internal cancer, jaundice, lichen planus, lichen sclerosus, lupus erythematosus, lymphoma, lymphoma—associated itch, leukemia-associated itch, malignancy, mastocytosis, menopause, multiple sclerosis, neoplasm, nerve irritation, neurogenic itch, neuropathic itch, notalgia paresthetica, notalgia obsessive-compulsive disorders, paresthetica, parasitic infection, papular uritcaria, pediculosis, peripheral neuropathy, photodermatitis, polycythemia vera, psychiatric disease, psychogenic itch, pruritic popular eruption of HIV, pruritic urticarial papules and plaques of pregnancy (PUPPP), psoriasis, psoriasis-associated itch, psoriatic itch, pubic lice, punctate palmoplantar keratoderma, renal itch, rheumatoid arthritis, scabies, scar growth, shaving, seborrheic dermatitis, stasis dermatitis, sunburn, swimmer's itch, systemic immune senescence, tactile hallucinations, Th17-associated inflammation, thyroid illness, uraemia, pruritus or uremic itch, urticaria, urticarial itch, varicella, viral infection, wound or scab healing, or xerosis.

Molecular Engineering

The following definitions and methods are provided to better define the present invention and to guide those of ordinary skill in the art in the practice of the present invention. Unless otherwise noted, terms are to be understood according to conventional usage by those of ordinary skill in the relevant art.

The terms "heterologous DNA sequence", "exogenous DNA segment" or "heterologous nucleic acid," as used herein, each refer to a sequence that originates from a source foreign to the particular host cell or, if from the same source, is modified from its original form. Thus, a heterologous gene in a host cell includes a gene that is endogenous to the particular host cell but has been modified through, for example, the use of DNA shuffling. The terms also include non-naturally occurring multiple copies of a naturally occurring DNA sequence. Thus, the terms refer to a DNA segment that is foreign or heterologous to the cell, or homologous to the cell but in a position within the host cell nucleic acid in which the element is not ordinarily found. Exogenous DNA segments are expressed to yield exogenous polypeptides. A "homologous" DNA sequence is a DNA sequence that is naturally associated with a host cell into which it is introduced.

Expression vector, expression construct, plasmid, or recombinant DNA construct is generally understood to refer to a nucleic acid that has been generated via human intervention, including by recombinant means or direct chemical synthesis, with a series of specified nucleic acid elements that permit transcription or translation of a particular nucleic acid in, for example, a host cell. The expression vector can be part of a plasmid, virus, or nucleic acid fragment. Typically, the expression vector can include a nucleic acid to be transcribed operably linked to a promoter.

A "promoter" is generally understood as a nucleic acid control sequence that directs transcription of a nucleic acid. An inducible promoter is generally understood as a promoter that mediates transcription of an operably linked gene in response to a particular stimulus. A promoter can include necessary nucleic acid sequences near the start site of transcription, such as, in the case of a polymerase II type promoter, a TATA element. A promoter can optionally include distal enhancer or repressor elements, which can be located as much as several thousand base pairs from the start site of transcription.

A "transcribable nucleic acid molecule" as used herein refers to any nucleic acid molecule capable of being transcribed into a RNA molecule. Methods are known for introducing constructs into a cell in such a manner that the transcribable nucleic acid molecule is transcribed into a functional mRNA molecule that is translated and therefore expressed as a protein product. Constructs may also be constructed to be capable of expressing antisense RNA molecules, in order to inhibit translation of a specific RNA molecule of interest. For the practice of the present disclosure, conventional compositions and methods for preparing and using constructs and host cells are well known to one skilled in the art (see e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754).

The "transcription start site" or "initiation site" is the position surrounding the first nucleotide that is part of the transcribed sequence, which is also defined as position +1. With respect to this site all other sequences of the gene and its controlling regions can be numbered. Downstream sequences (i.e., further protein encoding sequences in the 3' direction) can be denominated positive, while upstream sequences (mostly of the controlling regions in the 5' direction) are denominated negative.

"Operably-linked" or "functionally linked" refers preferably to the association of nucleic acid sequences on a single nucleic acid fragment so that the function of one is affected by the other. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation. The two nucleic acid molecules may be part of a single contiguous nucleic acid molecule and may be adjacent. For example, a promoter is operably linked to a gene of interest if the promoter regulates or mediates transcription of the gene of interest in a cell.

A "construct" is generally understood as any recombinant nucleic acid molecule such as a plasmid, cosmid, virus, autonomously replicating nucleic acid molecule, phage, or linear or circular single-stranded or double-stranded DNA or RNA nucleic acid molecule, derived from any source, capable of genomic integration or autonomous replication, comprising a nucleic acid molecule where one or more nucleic acid molecule has been operably linked.

A constructs of the present disclosure can contain a promoter operably linked to a transcribable nucleic acid molecule operably linked to a 3' transcription termination nucleic acid molecule. In addition, constructs can include but are not limited to additional regulatory nucleic acid molecules from, e.g., the 3'-untranslated region (3' UTR). Constructs can include but are not limited to the 5' untranslated regions (5' UTR) of an mRNA nucleic acid molecule which can play an important role in translation initiation and can also be a genetic component in an expression construct. These additional upstream and downstream regulatory nucleic acid molecules may be derived from a source that is native or heterologous with respect to the other elements present on the promoter construct.

The term "transformation" refers to the transfer of a nucleic acid fragment into the genome of a host cell, resulting in genetically stable inheritance. Host cells containing the transformed nucleic acid fragments are referred to as "transgenic" cells, and organisms comprising transgenic cells are referred to as "transgenic organisms".

"Transformed," "transgenic," and "recombinant" refer to a host cell or organism such as a bacterium, cyanobacterium, animal or a plant into which a heterologous nucleic acid molecule has been introduced. The nucleic acid molecule can be stably integrated into the genome as generally known in the art and disclosed (Sambrook 1989; Innis 1995; Gelfand 1995; Innis & Gelfand 1999). Known methods of PCR include, but are not limited to, methods using paired primers, nested primers, single specific primers, degenerate primers, gene-specific primers, vector-specific primers, partially mismatched primers, and the like. The term "untransformed" refers to normal cells that have not been through the transformation process.

"Wild-type" refers to a virus or organism found in nature without any known mutation.

Design, generation, and testing of the variant nucleotides, and their encoded polypeptides, having the above required percent identities and retaining a required activity of the expressed protein is within the skill of the art. For example, directed evolution and rapid isolation of mutants can be according to methods described in references including, but not limited to, Link et al. (2007) Nature Reviews 5(9), 680-688; Sanger et al. (1991) Gene 97(1), 119-123; Ghadessy et al. (2001) Proc Natl Acad Sci USA 98(8) 4552-4557. Thus, one skilled in the art could generate a large number of nucleotide and/or polypeptide variants having, for example, at least 95-99% identity to the reference sequence described herein and screen such for desired phenotypes according to methods routine in the art.

Nucleotide and/or amino acid sequence identity percent (%) is understood as the percentage of nucleotide or amino acid residues that are identical with nucleotide or amino acid residues in a candidate sequence in comparison to a reference sequence when the two sequences are aligned. To determine percent identity, sequences are aligned and if necessary, gaps are introduced to achieve the maximum percent sequence identity. Sequence alignment procedures to determine percent identity are well known to those of skill in the art. Often publicly available computer software such as BLAST, BLAST2, ALIGN2 or Megalign (DNASTAR) software is used to align sequences. Those skilled in the art can determine appropriate parameters for measuring alignment, including any algorithms needed to achieve maximal alignment over the full-length of the sequences being compared. When sequences are aligned, the percent sequence identity of a given sequence A to, with, or against a given sequence B (which can alternatively be phrased as a given sequence A that has or comprises a certain percent sequence identity to, with, or against a given sequence B) can be calculated as: percent sequence identity=X/Y100, where X is the number of residues scored as identical matches by the sequence alignment program's or algorithm's alignment of A and B and Y is the total number of residues in B. If the length of sequence A is not equal to the length of sequence B, the percent sequence identity of A to B will not equal the percent sequence identity of B to A.

Generally, conservative substitutions can be made at any position so long as the required activity is retained. So-called conservative exchanges can be carried out in which the amino acid which is replaced has a similar property as the original amino acid, for example the exchange of Glu by Asp, Gln by Asn, Val by Ile, Leu by Ile, and Ser by Thr. For example, amino acids with similar properties can be Aliphatic amino acids (e.g., Glycine, Alanine, Valine, Leucine, Isoleucine); Hydroxyl or sulfur/selenium-containing amino acids (e.g., Serine, Cysteine, Selenocysteine, Threonine, Methionine); Cyclic amino acids (e.g., Proline); Aromatic amino acids (e.g., Phenylalanine, Tyrosine, Tryptophan); Basic amino acids (e.g., Histidine, Lysine, Arginine); or Acidic and their Amide (e.g., Aspartate, Glutamate, Asparagine, Glutamine). Deletion is the replacement of an amino acid by a direct bond. Positions for deletions include the termini of a polypeptide and linkages between individual protein domains. Insertions are introductions of amino acids into the polypeptide chain, a direct bond formally being replaced by one or more amino acids. Amino acid sequence can be modulated with the help of art-known computer simulation programs that can produce a polypeptide with, for example, improved activity or altered regulation. On the basis of this artificially generated polypeptide sequences, a corresponding nucleic acid molecule coding for such a modulated polypeptide can be synthesized in-vitro using the specific codon-usage of the desired host cell.

"Highly stringent hybridization conditions" are defined as hybridization at 65° C. in a 6×SSC buffer (i.e., 0.9 M sodium chloride and 0.09 M sodium citrate). Given these conditions, a determination can be made as to whether a given set of sequences will hybridize by calculating the melting temperature ($T_m$) of a DNA duplex between the two sequences. If a particular duplex has a melting temperature lower than 65° C. in the salt conditions of a 6×SSC, then the two sequences will not hybridize. On the other hand, if the melting temperature is above 65° C. in the same salt conditions, then the sequences will hybridize. In general, the melting temperature for any hybridized DNA:DNA sequence can be determined using the following formula: $T_m = 81.5° C. + 16.6(\log_{10}[Na^+]) + 0.41(\text{fraction G/C content}) - 0.63(\% \text{formamide}) - (600/l)$. Furthermore, the $T_m$ of a DNA:DNA hybrid is decreased by 1-1.5° C. for every 1% decrease in nucleotide identity (see e.g., Sambrook and Russel, 2006).

Host cells can be transformed using a variety of standard techniques known to the art (see, e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754). Such techniques include, but are not limited to, viral infection, calcium phosphate transfection, liposome-mediated transfection, microprojectile-mediated delivery, receptor-mediated uptake, cell fusion, electroporation, and the like. The transfected cells can be selected and propagated to provide recombinant host cells that comprise the expression vector stably integrated in the host cell genome.

Exemplary nucleic acids which may be introduced to a host cell include, for example, DNA sequences or genes from another species, or even genes or sequences which originate with or are present in the same species, but are incorporated into recipient cells by genetic engineering methods. The term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA which is already present in the cell, DNA from another individual of the same type of organism, DNA from a different organism, or a DNA generated externally, such as a DNA sequence containing an antisense message of a gene, or a DNA sequence encoding a synthetic or modified version of a gene.

Host strains developed according to the approaches described herein can be evaluated by a number of means known in the art (see e.g., Studier (2005) Protein Expr Purif. 41(1), 207-234; Gellissen, ed. (2005) Production of Recombinant Proteins: Novel Microbial and Eukaryotic Expression Systems, Wiley-VCH, ISBN-10: 3527310363; Baneyx (2004) Protein Expression Technologies, Taylor & Francis, ISBN-10: 0954523253).

Methods of down-regulation or silencing genes are known in the art. For example, expressed protein activity can be down-regulated or eliminated using antisense oligonucleotides, protein aptamers, nucleotide aptamers, and RNA interference (RNAi) (e.g., small interfering RNAs (siRNA), short hairpin RNA (shRNA), and micro RNAs (miRNA)

(see e.g., Fanning and Symonds (2006) Handb Exp Pharmacol. 173, 289-303G, describing hammerhead ribozymes and small hairpin RNA; Helene, C., et al. (1992) Ann. N.Y. Acad. Sci. 660, 27-36; Maher (1992) Bioassays 14(12): 807-15, describing targeting deoxyribonucleotide sequences; Lee et al. (2006) Curr Opin Chem Biol. 10, 1-8, describing aptamers; Reynolds et al. (2004) Nature Biotechnology 22(3), 326-330, describing RNAi; Pushparaj and Melendez (2006) Clinical and Experimental Pharmacology and Physiology 33(5-6), 504-510, describing RNAi; Dillon et al. (2005) Annual Review of Physiology 67, 147-173, describing RNAi; Dykxhoorn and Lieberman (2005) Annual Review of Medicine 56, 401-423, describing RNAi). RNAi molecules are commercially available from a variety of sources (e.g., Ambion, TX; Sigma Aldrich, MO; Invitrogen). Several siRNA molecule design programs using a variety of algorithms are known to the art (see e.g., Cenix algorithm, Ambion; BLOCK-iT™ RNAi Designer, Invitrogen; siRNA Whitehead Institute Design Tools, Bioinofrmatics & Research Computing). Traits influential in defining optimal siRNA sequences include G/C content at the termini of the siRNAs, Tm of specific internal domains of the siRNA, siRNA length, position of the target sequence within the CDS (coding region), and nucleotide content of the 3' overhangs.

Formulation

The agents and compositions described herein can be formulated by any conventional manner using one or more pharmaceutically acceptable carriers or excipients as described in, for example, Remington's Pharmaceutical Sciences (A. R. Gennaro, Ed.), 21st edition, ISBN: 0781746736 (2005), incorporated herein by reference in its entirety. Such formulations will contain a therapeutically effective amount of a biologically active agent described herein, which can be in purified form, together with a suitable amount of carrier so as to provide the form for proper administration to the subject.

The term "therapeutically effective amount" can refers to an amount of a compound that, when administered to a subject for treating a disease, is sufficient, in combination with another agent or alone, in one or more doses, to effect such treatment for the disease. The "therapeutically effective amount" can vary depending on the compound, the severity of disease, and the age, weight, etc., of the subject to be treated. For the purposes of the present disclosure, a "therapeutically effective amount of a JAK inhibitor" refers to an amount between about 0.01 mg/kg to about 100 mg/kg of body weight per day, preferably about 0.1 mg/kg to about 10 mg/kg of body weight per day, or an equivalent dosage administered more or less frequently.

In some embodiments, a therapeutically effective amount of a JAK inhibitor can be about 0.01 mg/kg to about 100 mg/kg of body weight per day. For example, the device diameter can be about 1 mg/kg about 2 mg/kg about 3 mg/kg about 4 mg/kg about 5 mg/kg about 6 mg/kg about 7 mg/kg about 8 mg/kg; about 9 mg/kg; about 10 mg/kg, about 11 mg/kg; about 12 mg/kg, about 13 mg/kg, about 14 mg/kg; about 15 mg/kg; about 16 mg/kg; about 17 mg/kg; about 18 mg/kg; about 19 mg/kg; about 20 mg/kg; about 21 mg/kg; about 22 mg/kg; about 23 mg/kg; about 24 mg/kg; about 25 mg/kg; about 26 mg/kg; about 27 mg/kg; about 28 mg/kg; about 29 mg/kg; about 30 mg/kg; about 31 mg/kg; about 32 mg/kg; about 33 mg/kg; about 34 mg/kg; about 35 mg/kg; about 36 mg/kg; about 37 mg/kg; about 38 mg/kg; about 39 mg/kg; about 40 mg/kg; about 41 mg/kg; about 42 mg/kg; about 43 mg/kg; about 44 mg/kg; about 45 mg/kg; about 46 mg/kg; about 47 mg/kg; about 48 mg/kg; about 49 mg/kg; about 50 mg/kg; about 51 mg/kg; about 52 mg/kg; about 53 mg/kg; about 54 mg/kg; about 55 mg/kg; about 56 mg/kg; about 57 mg/kg; about 58 mg/kg; about 59 mg/kg; about 60 mg/kg; about 61 mg/kg; about 62 mg/kg; about 63 mg/kg; about 64 mg/kg; about 65 mg/kg; about 66 mg/kg; about 67 mg/kg; about 68 mg/kg; about 69 mg/kg; about 70 mg/kg; about 71 mg/kg; about 72 mg/kg; about 73 mg/kg; about 74 mg/kg; about 75 mg/kg; about 76 mg/kg; about 77 mg/kg; about 78 mg/kg; about 79 mg/kg; about 80 mg/kg; about 81 mg/kg; about 82 mg/kg; about 83 mg/kg; about 84 mg/kg; about 85 mg/kg; about 86 mg/kg; about 87 mg/kg; about 88 mg/kg; about 89 mg/kg; about 90 mg/kg; about 91 mg/kg; about 92 mg/kg; about 93 mg/kg; about 94 mg/kg; about 95 mg/kg; about 96 mg/kg; about 97 mg/kg; about 98 mg/kg; about 99 mg/kg; about 100 mg/kg; about 101 mg/kg; about 102 mg/kg; about 103 mg/kg; about 104 mg/kg; about 105 mg/kg; about 106 mg/kg; about 107 mg/kg; about 108 mg/kg; about 109 mg/kg; about 110 mg/kg; about 111 mg/kg; about 112 mg/kg; about 113 mg/kg; about 114 mg/kg; about 115 mg/kg; about 116 mg/kg; about 117 mg/kg; about 118 mg/kg; about 119 mg/kg; about 120 mg/kg; about 121 mg/kg; about 122 mg/kg; about 123 mg/kg; about 124 mg/kg; about 125 mg/kg; about 126 mg/kg; about 127 mg/kg; about 128 mg/kg; about 129 mg/kg; about 130 mg/kg; about 131 mg/kg; about 132 mg/kg; about 133 mg/kg; about 134 mg/kg; about 135 mg/kg; about 136 mg/kg; about 137 mg/kg; about 138 mg/kg; about 139 mg/kg; about 140 mg/kg; about 141 mg/kg; about 142 mg/kg; about 143 mg/kg; about 144 mg/kg; about 145 mg/kg; about 146 mg/kg; about 147 mg/kg; about 148 mg/kg; about 149 mg/kg; about 150 mg/kg; about 151 mg/kg; about 152 mg/kg; about 153 mg/kg; about 154 mg/kg; about 155 mg/kg; about 156 mg/kg; about 157 mg/kg; about 158 mg/kg; about 159 mg/kg; about 160 mg/kg; about 161 mg/kg; about 162 mg/kg; about 163 mg/kg; about 164 mg/kg; about 165 mg/kg; about 166 mg/kg; about 167 mg/kg; about 168 mg/kg; about 169 mg/kg; about 170 mg/kg; about 171 mg/kg; about 172 mg/kg; about 173 mg/kg; about 174 mg/kg; about 175 mg/kg; about 176 mg/kg; about 177 mg/kg; about 178 mg/kg; about 179 mg/kg; about 180 mg/kg; about 181 mg/kg; about 182 mg/kg; about 183 mg/kg; about 184 mg/kg; about 185 mg/kg; about 186 mg/kg; about 187 mg/kg; about 188 mg/kg; about 189 mg/kg; about 190 mg/kg; about 191 mg/kg; about 192 mg/kg; about 193 mg/kg; about 194 mg/kg; about 195 mg/kg; about 196 mg/kg; about 197 mg/kg; about 198 mg/kg; about 199 mg/kg; or about 200 mg/kg. Recitation of each of these discrete values is understood to include ranges between each value.

In some embodiments, therapeutically effective amount of a JAK inhibitor may be about 0.01 to about 100 mg/kg of body weight per day, preferably about 0.1 to about 10 mg/kg of body weight per day. In some embodiments, a therapeutically effective amount of a JAK inhibitor may be about 0.1 to about 1 mg/kg of body weight per day. In other embodiments, a therapeutically effective amount of a JAK inhibitor may be about 0.25 mg/kg to about 2.5 mg/kg of body weight per day. In yet other embodiments, a therapeutically effective amount of a JAK inhibitor may be about 0.5 mg/kg to about 5 mg/kg of body weight per day. In still other embodiments, a therapeutically effective amount of a JAK inhibitor may be about 0.75 mg/kg to about 7.5 mg/kg of body weight per day. In different embodiments, a therapeutically effective amount of a JAK inhibitor may be about 1 mg/kg to about 10 mg/kg of body weight per day. Recitation of each of these ranges is understood to include discrete values between each value in the range.

Although the term "therapeutically effective amount" is described as an amount of a JAK inhibitor per day, a skilled artisan will appreciate that a daily amount may be divided into one or more dosages to be administered once, twice, three times or more daily. Alternatively, it may be desirable to administer the JAK inhibitor on a less frequent basis (e.g. once, twice, or three times per week; or once, twice, or three times per month). A skilled artisan will appreciate that the frequency of administration may influence the amount to be administered (e.g. generally speaking, monthly administration>weekly administration>daily administration>multiple times per day), and can formulate the pharmaceutical composition to provide a therapeutically effective amount of the JAK inhibitor based on the disclosures herein.

Another aspect of the present disclosure provides administering one or more "additional active ingredients" in combination with a JAK inhibitor. The additional active ingredient may be administered by the same or different route of administration. When administered by the same route of administration, the additional active ingredient may be formulated with a JAK inhibitor (i.e., same pharmaceutical composition), or separately from the JAK inhibitor. Non-limiting examples of additional active ingredients that may be administered in combination with a JAK inhibitor of the present disclosure includes, but is not limited to, antihistamines (e.g. cetirizine, diphenhydramine, doxepin, fexofenadine, hydroxyzine, loratadine, desloratidine), corticosteroids (e.g. triamcinolone, hydrocortisone, prednisone), local anesthetics (e.g. benzocaine, capsaicin, diperodon, lidocaine, menthol, polidocanol, pramoxine, prilocaine), topical immunomodulators (e.g. calcineurin inhibitors, such as pimecrolimus, tacrolimus), µ-opioid receptor antagonists and K-opioid receptor agonists (e.g. butorphanol, nalfurafine, methylnaltrexone, nalmefene, naltrexone), antibiotics (rifampicin), cholestyramine, salicylic acid, antidepressants (e.g. fluvoxamine, mirtazapine, paroxetine, sertraline), and neuroleptics (e.g. gabapentin, pregablin).

The term "formulation" refers to preparing a drug in a form suitable for administration to a subject, such as a human. Thus, a "formulation" can include pharmaceutically acceptable excipients, including diluents or carriers.

The term "pharmaceutically acceptable" as used herein can describe substances or components that do not cause unacceptable losses of pharmacological activity or unacceptable adverse side effects. Examples of pharmaceutically acceptable ingredients can be those having monographs in United States Pharmacopeia (USP 29) and National Formulary (NF 24), United States Pharmacopeial Convention, Inc, Rockville, Md., 2005 ("USP/NF"), or a more recent edition, and the components listed in the continuously updated Inactive Ingredient Search online database of the FDA. Other useful components that are not described in the USP/NF, etc. may also be used.

The term "pharmaceutically acceptable excipient," as used herein, can include any and all solvents, dispersion media, coatings, antibacterial and antifungal agents, isotonic, or absorption delaying agents. The use of such media and agents for pharmaceutical active substances is well known in the art (see generally Remington's Pharmaceutical Sciences (A. R. Gennaro, Ed.), 21st edition, ISBN: 0781746736 (2005)). Except insofar as any conventional media or agent is incompatible with an active ingredient, its use in the therapeutic compositions is contemplated. Supplementary active ingredients can also be incorporated into the compositions.

A "stable" formulation or composition can refer to a composition having sufficient stability to allow storage at a convenient temperature, such as between about 0° C. and about 60° C., for a commercially reasonable period of time, such as at least about one day, at least about one week, at least about one month, at least about three months, at least about six months, at least about one year, or at least about two years.

The formulation should suit the mode of administration. The agents of use with the current disclosure can be formulated by known methods for administration to a subject using several routes which include, but are not limited to, parenteral, pulmonary, oral, topical, intradermal, intramuscular, intraperitoneal, intravenous, subcutaneous, intranasal, epidural, ophthalmic, buccal, and rectal. The individual agents may also be administered in combination with one or more additional agents or together with other biologically active or biologically inert agents. Such biologically active or inert agents may be in fluid or mechanical communication with the agent(s) or attached to the agent(s) by ionic, covalent, Van der Waals, hydrophobic, hydrophilic or other physical forces.

Controlled-release (or sustained-release) preparations may be formulated to extend the activity of the agent(s) and reduce dosage frequency. Controlled-release preparations can also be used to effect the time of onset of action or other characteristics, such as blood levels of the agent, and consequently affect the occurrence of side effects. Controlled-release preparations may be designed to initially release an amount of an agent(s) that produces the desired therapeutic effect, and gradually and continually release other amounts of the agent to maintain the level of therapeutic effect over an extended period of time. In order to maintain a near-constant level of an agent in the body, the agent can be released from the dosage form at a rate that will replace the amount of agent being metabolized or excreted from the body. The controlled-release of an agent may be stimulated by various inducers, e.g., change in pH, change in temperature, enzymes, water, or other physiological conditions or molecules.

Agents or compositions described herein can also be used in combination with other therapeutic modalities, as described further below. Thus, in addition to the therapies described herein, one may also provide to the subject other therapies known to be efficacious for treatment of the disease, disorder, or condition.

Therapeutic Methods

Also provided is a process of treating chronic idiopathic pruritus in a subject in need thereof. The process comprises administration of a therapeutically effective amount of a JAK inhibitor, so as to prevent, reduce, or relieve the symptoms of pruritus.

As described herein, it is shown that patients with recalcitrant chronic itch markedly improve when treated with JAK inhibitors.

Another aspect of the present disclosure provides treatment of chronic idiopathic pruritus includes. In some embodiments, a method of the present disclosure causes the clinical symptoms of CIP not to develop in a subject that may be predisposed to the disease (i.e., prevents pruritus). In other embodiments, a method of the present disclosure arrests or reduces the progression of CIP or a symptom of CIP. In other embodiments, a method of the present disclosure causes regression of CIP or symptom of CIP.

In certain embodiments, the number of Itch-Free Days in a subject is increased at the end of the treatment period as compared to beginning of the treatment period. For example, the number of Itch-Free Days may increase by at least 1, at least 2, at least 3, at least 4, at least 5, at least 6, at least 7 days, at least 8 days, or at least 9 days. Alternatively, the number of Itch-Free Days may increase by at least 10, at least 11, at least 12, at least 13, at least 14, at least 15, at least 16 days, at least 17 days, at least 18 days, or at least 19 days.

In certain embodiments, the severity of itching in a subject is decreased at the end of the treatment period as compared to the beginning of the treatment period. For example, a VAS score of itching may decrease by about 0.5, about 1.0, or about 1.5. Alternatively, a VAS score of itching may decrease by about 1.5, about 2.0, or about 2.5, or about 3.0. In another alternative, a VAS score of itching may decrease by about 3.0, about 3.5, about 4.0, about 4.5. In yet another alternative, itching severity may improve from extremely severe to severe, preferably from extremely severe to moderate, or more preferably from extremely severe to mild. In still another alternative, itching severity may improve from severe to moderate, or preferably from severe to mild. In another example, itching severity may improve from moderate to mild.

In certain embodiments, the quality of life of a subject is decreased at the end of the treatment period as compared to the beginning of the treatment period.

A skilled artisan will appreciate that the route of administration may influence the amount that is needed to be administered in order to achieve a therapeutic effect. Generally speaking, oral>IV>transdermal/transmucosal>intranasal>intrathecal/epidural.

Those skilled in the art will appreciate that dosages may also be determined with guidance from Goodman & Goldman's The Pharmacological Basis of Therapeutics, Tenth Edition (2001), Appendix II, pp. 475-493, and the Physicians' Desk Reference.

Methods described herein are generally performed on a subject in need thereof. A subject in need of the therapeutic methods described herein can be a subject having, diagnosed with, suspected of having, or at risk for developing pruritus. A determination of the need for treatment will typically be assessed by a history and physical exam consistent with the disease or condition at issue. Diagnosis of the various conditions treatable by the methods described herein is within the skill of the art. The subject can be an animal subject, including a mammal, such as horses, cows, dogs, cats, sheep, pigs, mice, rats, monkeys, hamsters, guinea pigs, and chickens, and humans. For example, the subject can be a human subject. As another example, a subject can be a mammal. A mammal can include, but is not limited to a human, a companion animal, a livestock animal, a zoo animal, or a research animal. Non-limiting examples of companion animals include a dog or a cat. Non-limiting example of a livestock animal include a cow, a pig, a horse, a sheep or a goat. Non-limiting examples of a research animal include a non-human primate or a rodent.

The term "treating," as used herein, can refer to controlling or preventing the progression of chronic idiopathic pruritus. The term "controlling", "treating" or "treatment" of chronic idiopathic pruritus can include: (1) preventing chronic idiopathic pruritus (i.e., causing the clinical symptoms or signs of chronic idiopathic pruritus not to develop in a subject that may be predisposed to the disease but does not yet experience or display symptoms/signs of the disease); (2) inhibiting the chronic idiopathic pruritus (i.e., arresting or reducing the progression of the disease or its clinical symptoms or signs); or (3) relieving the chronic idiopathic pruritus (i.e., causing regression of the disease or its clinical symptoms or signs).

Generally, a safe and effective amount of a JAK inhibitor is, for example, that amount that would cause the desired therapeutic effect in a subject while minimizing undesired side effects. In various embodiments, an effective amount of a JAK inhibitor described herein can substantially inhibit pruritus, slow the progress of pruritus, or limit the development of pruritus.

According to the methods described herein, administration can be parenteral, pulmonary, oral, topical, intradermal, intramuscular, intraperitoneal, intravenous, intrathecally, subcutaneous, intranasal, epidural, ophthalmic, buccal, or rectal administration.

Parenteral administration, as used herein, can be administration by injection, infusion or implantation. Non-limiting examples of include epidural, intra-arterial, intracardiac, intramuscular, intraperitoneal, intraspinal, intrathoracic, intrathecal, intravenous, or subcutaneous techniques.

When used in the treatments described herein, a therapeutically effective amount of a JAK inhibitor can be employed in pure form or, where such forms exist, in pharmaceutically acceptable salt form and with or without a pharmaceutically acceptable excipient. For example, the compounds of the present disclosure can be administered, at a reasonable benefit/risk ratio applicable to any medical treatment, in a sufficient amount to reduce, prevent, or treat pruritus.

The amount of a composition described herein that can be combined with a pharmaceutically acceptable carrier to produce a single dosage form will vary depending upon the host treated and the particular mode of administration. It will be appreciated by those skilled in the art that the unit content of agent contained in an individual dose of each dosage form need not in itself constitute a therapeutically effective amount, as the necessary therapeutically effective amount could be reached by administration of a number of individual doses.

Toxicity and therapeutic efficacy of compositions described herein can be determined by standard pharmaceutical procedures in cell cultures or experimental animals for determining the $LD_{50}$ (the dose lethal to 50% of the population) and the $ED_{50}$, (the dose therapeutically effective in 50% of the population). The dose ratio between toxic and therapeutic effects is the therapeutic index that can be expressed as the ratio $LD_{50}/ED_{50}$, where larger therapeutic indices are generally understood in the art to be optimal.

The specific therapeutically effective dose level for any particular subject will depend upon a variety of factors including the disorder being treated and the severity of the disorder; activity of the specific compound employed; the specific composition employed; the age, body weight, general health, sex and diet of the subject; the time of administration; the route of administration; the rate of excretion of the composition employed; the duration of the treatment; drugs used in combination or coincidental with the specific compound employed; and like factors well known in the medical arts (see e.g., Koda-Kimble et al. (2004) Applied Therapeutics: The Clinical Use of Drugs, Lippincott Williams & Wilkins, ISBN 0781748453; Winter (2003) Basic Clinical Pharmacokinetics, $4^{th}$ ed., Lippincott Williams & Wilkins, ISBN 0781741475; Sharqel (2004) Applied Biopharmaceutics & Pharmacokinetics, McGraw-Hill/Appleton & Lange, ISBN 0071375503). For example, it is well within the skill of the art to start doses of the composition at levels lower than those required to achieve the desired therapeutic effect and to gradually increase the dosage until the desired effect is achieved. If desired, the effective daily dose may be divided into multiple doses for purposes of administration. Consequently, single dose compositions may contain such amounts or submultiples thereof to make up the daily dose. It will be understood, however, that the total daily usage of the compounds and compositions of the present disclosure will be decided by an attending physician within the scope of sound medical judgment.

Again, each of the states, diseases, disorders, and conditions, described herein, as well as others, can benefit from compositions and methods described herein. Generally, treating a state, disease, disorder, or condition includes preventing or delaying the appearance of clinical symptoms in a mammal that may be afflicted with or predisposed to the state, disease, disorder, or condition but does not yet experience or display clinical or subclinical symptoms thereof. Treating can also include inhibiting the state, disease, disorder, or condition, e.g., arresting or reducing the development of the disease or at least one clinical or subclinical symptom thereof. Furthermore, treating can include relieving the disease, e.g., causing regression of the state, disease, disorder, or condition or at least one of its clinical or subclinical symptoms. A benefit to a subject to be treated can be either statistically significant or at least perceptible to the subject or to a physician.

Administration of a JAK inhibitor can occur as a single event or over a time course of treatment. For example, a JAK inhibitor can be administered daily, weekly, bi-weekly, or monthly. For treatment of acute conditions, the time course of treatment will usually be at least several days. Certain conditions could extend treatment from several days to several weeks. For example, treatment could extend over one week, two weeks, or three weeks. For more chronic conditions, treatment could extend from several weeks to several months or even a year or more.

Treatment in accord with the methods described herein can be performed prior to, concurrent with, or after conventional treatment modalities for pruritus. Conventional treatments can include topical antipruritics in the form of creams and sprays are often available over-the-counter or oral anti-itch drugs. For example, conventional treatments can include antihistamines, such as diphenhydramine (Benadryl); corticosteroids (such as hydrocortisone topical cream, a topical steroid); counterirritants, such as mint oil, menthol, or camphor; crotamiton (trade name Eurax); local anesthetics, such as benzocaine topical cream (Lanacane); phototherapy (e.g., UVB), maintaining adequate skin moisture; or topical emollients. Furthermore, TRPV1 inhibitors, dupilumab, or secukinumab can be used to treat itch.

A JAK inhibitor can be administered simultaneously or sequentially with another agent, such as a, antibiotic, an antiinflammatory, or another agent (e.g., any of the above in the preceding paragraph). For example, a JAK inhibitor can be administered simultaneously with another agent, such as an antibiotic or an antiinflammatory. Simultaneous administration can occur through administration of separate compositions, each containing one or more of a JAK inhibitor, an antibiotic, an antiinflammatory, or another agent. Simultaneous administration can occur through administration of one composition containing two or more of a JAK inhibitor, an antibiotic, an antiinflammatory, or another agent. A JAK inhibitor can be administered sequentially with an antibiotic, an antiinflammatory, or another agent. For example, a JAK inhibitor can be administered before or after administration of an antibiotic, an antiinflammatory, or another agent.

Administration

Another aspect of the present disclosure provides systemically administering a therapeutically effective amount of a JAK inhibitor for a period of time.

Agents and compositions described herein can be administered according to methods described herein in a variety of means known to the art. The agents and composition can be used therapeutically either as exogenous materials or as endogenous materials. Exogenous agents are those produced or manufactured outside of the body and administered to the body. Endogenous agents are those produced or manufactured inside the body by some type of device (biologic or other) for delivery within or to other organs in the body.

Route of Administration

JAK inhibitor(s) may be formulated into pharmaceutical compositions and systemically administered by a number of different means to deliver a therapeutically effective amount. Such compositions may be administered, for example, by nasal administration, oral administration, parenteral administration, rectal administration, topical administration, transdermal administration, or transmucosal administration, in dosage unit formulations containing conventional nontoxic pharmaceutically acceptable carriers, adjuvants, and vehicles as desired. Formulation of drugs is discussed in, for example, Hoover, John E., Remington's Pharmaceutical Sciences, Mack Publishing Co., Easton, Pa. (1975), and Liberman, H. A. and Lachman. L., Eds., Pharmaceutical Dosage Forms, Marcel Decker, New York, N.Y. (1980).

Preparations for oral administration generally contain inert excipients in addition to the active pharmaceutical ingredient. Oral preparations may be enclosed in gelatin capsules or compressed into tablets. Common excipients used in such preparations include pharmaceutically compatible fillers/diluents such as microcrystalline cellulose, hydroxypropyl methylcellulose, starch, lactose, sucrose, glucose, mannitol, sorbitol, dibasic calcium phosphate, or calcium carbonate; binding agents such as alginic acid, carboxymethylcellulose, microcrystalline cellulose, gelatin, gum tragacanth, or polyvinylpyrrolidone; disintegrating agents such as alginic acid, cellulose, starch, or polyvinylpyrrolidone; lubricants such as calcium stearate, magnesium stearate, talc, silica, or sodium stearyl fumarate; glidants such as colloidal silicon dioxide; sweetening agents such as sucrose or saccharin; flavoring agents such as peppermint, methyl salicylate, or citrus flavoring; coloring agents; and preservatives such as antioxidants (e.g., vitamin A, vitamin C, vitamin E, or retinyl palmitate), citric acid, or sodium citrate. Oral preparations may also be administered as aqueous suspensions, elixirs, or syrups. For these, the active ingredient may be combined with various sweetening or flavoring agents, coloring agents, and, if so desired, emulsifying and/or suspending agents, as well as diluents such as water, ethanol, glycerin, and combinations thereof.

For parenteral administration, the preparation may be an aqueous or an oil-based solution. Aqueous solutions may include a sterile diluent such as water, saline solution, a pharmaceutically acceptable polyol such as glycerol, propylene glycol, or other synthetic solvents; an antibacterial and/or antifungal agent such as benzyl alcohol, methyl paraben, chlorobutanol, phenol, thimerosal, and the like; an antioxidant such as ascorbic acid or sodium bisulfite; a chelating agent such as etheylenediaminetetraacetic acid; a buffer such as acetate, citrate, or phosphate; and/or an agent for the adjustment of tonicity such as sodium chloride, dextrose, or a polyalcohol such as mannitol or sorbitol. The pH of the aqueous solution may be adjusted with acids or bases such as hydrochloric acid or sodium hydroxide. Oil-based solutions or suspensions may further comprise sesame, peanut, olive oil, or mineral oil. The composition may also be provided in a powder form for reconstitution with a suitable vehicle including, but not limited to, sterile, pyrogen-free water.

For topical, transdermal or transmucosal administration, penetrants appropriate to the barrier to be permeated are generally included in the preparation. Transmucosal administration may be accomplished through the use of nasal sprays, aerosol sprays, tablets, or suppositories, and transdermal administration may be via ointments, salves, gels, patches, or creams as generally known in the art. Non-limiting examples of suitable carriers for transdermal embodiments include mineral oil, liquid petrolatum, white petrolatum, propylene glycol, polyoxyethylene, polyoxypropylene compound, emulsifying wax, sorbitan monostearate, Polysorbate 60, cetyl esters wax, cetearyl alcohol, 2-octyldodecanol, benzyl alcohol, and water. For these embodiments, the molecular weight of the composition may range from about 1 to about 50 Daltons For nasal administration, compositions may be formulated as a solution, suspension, or emulsion that may be administered as a dry powder or in the form of an aerosol using a propellant, such as dichlorodifluoromethane or trichlorofluoromethane. A nasal spray can include a saline spray.

In some embodiments, the route of administration is chosen from subcutaneous, epidural, intrathecal, intravenous, nasal, oral, or topical. In other preferred embodiments, the route of administration is chosen from intrathecal and nasal.

As discussed above, administration can be parenteral, pulmonary, oral, topical, intradermal, intramuscular, intraperitoneal, intravenous, subcutaneous, intranasal, epidural, ophthalmic, buccal, or rectal administration.

Delivery Methods

Agents and compositions described herein can be administered in a variety of methods well known in the arts. Administration can include, for example, methods involving oral ingestion, direct injection (e.g., systemic or stereotactic), implantation of cells engineered to secrete the factor of interest, drug-releasing biomaterials, polymer matrices, gels, permeable membranes, osmotic systems, multilayer coatings, microparticles, implantable matrix devices, mini-osmotic pumps, implantable pumps, injectable gels and hydrogels, liposomes, micelles (e.g., up to 30 µm), nanospheres (e.g., less than 1 µm), microspheres (e.g., 1-100 µm), reservoir devices, a combination of any of the above, or other suitable delivery vehicles to provide the desired release profile in varying proportions. Other methods of controlled-release delivery of agents or compositions will be known to the skilled artisan and are within the scope of the present disclosure.

Delivery systems may include, for example, an infusion pump which may be used to administer the agent or composition in a manner similar to that used for delivering insulin or chemotherapy to specific organs or tumors. Typically, using such a system, an agent or composition can be administered in combination with a biodegradable, biocompatible polymeric implant that releases the agent over a controlled period of time at a selected site. Examples of polymeric materials include polyanhydrides, polyorthoesters, polyglycolic acid, polylactic acid, polyethylene vinyl acetate, and copolymers and combinations thereof. In addition, a controlled release system can be placed in proximity of a therapeutic target, thus requiring only a fraction of a systemic dosage.

Agents can be encapsulated and administered in a variety of carrier delivery systems. Examples of carrier delivery systems include microspheres, hydrogels, polymeric implants, smart polymeric carriers, and liposomes (see generally, Uchegbu and Schatzlein, eds. (2006) Polymers in Drug Delivery, CRC, ISBN-10: 0849325331). Carrier-based systems for molecular or biomolecular agent delivery can: provide for intracellular delivery; tailor biomolecule/agent release rates; increase the proportion of biomolecule that reaches its site of action; improve the transport of the drug to its site of action; allow colocalized deposition with other agents or excipients; improve the stability of the agent in vivo; prolong the residence time of the agent at its site of action by reducing clearance; decrease the nonspecific delivery of the agent to nontarget tissues; decrease irritation caused by the agent; decrease toxicity due to high initial doses of the agent; alter the immunogenicity of the agent; decrease dosage frequency, improve taste of the product; or improve shelf life of the product.

Treatment Period

According to the method of the invention, a therapeutically effective amount of a JAK inhibitor is administered to a subject in need thereof for a period of time ("the treatment period"), sufficient to treat CIP. The period of time the JAK inhibitor is administered may be referred to as a "treatment period."

In some embodiments, the amount of a JAK inhibitor and frequency of administration does not vary during a treatment period. For example, a JAK inhibitor may be administered daily for about 1, 2, 3, 4, 5, 6, or 7 days. Alternatively, a JAK inhibitor may be administered daily for about 2, 3, 4, 5, 6, 7, 8, 9, 10, 11, or 12 weeks. In another alternative, a JAK inhibitor may be administered daily for 3 months, 6 months, 12 months or more. In still other alternative, a JAK inhibitor may be administered weekly for about 2, 3, 4, 5, 6, 7, 8, 9, 10, 11, or 12 weeks. In yet another alternative, a JAK inhibitor may be administered weekly for 3 months, 6 months, 12 months or more. In another alternative, a JAK inhibitor may be administered monthly for 3 months, 6 months, 12 months or more. Alternatively, a JAK inhibitor may be administered on an "as needed" basis.

In other embodiments, the amount a JAK inhibitor and frequency of administration can vary during a treatment period. For example, a treatment period may comprise a first phase and a second phase, wherein (a) an amount of a JAK inhibitor administered in the first phase is greater than an amount of the JAK inhibitor administered in the second phase; (b) a JAK inhibitor is administered more frequently in the first is greater in the second phase; or (c) an amount of a JAK inhibitor administered in the first phase is greater than an amount of the JAK inhibitor administered in the second phase, and administration is more frequent in the first phase than in the second phase. It is also contemplated that the route of administration differs between the first and second phase. The period of time for the first phase may be about 2, 3, 4, 5, 6, 7, 8, 9, 10, 11, or 12 weeks, and the period of time for the second phase may be about 1, 2, 3, 4, 5, 6, 7, 8, 9, 10, or 11 weeks. A treatment phase may also comprise more than two phases (e.g. 3, 4, 5, or more phases).

Screening

Also provided are methods for screening for JAK inhibitors.

The subject methods find use in the screening of a variety of different candidate molecules (e.g., potentially therapeutic candidate molecules). Candidate substances for screening according to the methods described herein include, but are not limited to, fractions of tissues or cells, nucleic acids, polypeptides, siRNAs, antisense molecules, aptamers, ribozymes, triple helix compounds, antibodies, and small (e.g., less than about 2000 mw, or less than about 1000 mw, or less than about 800 mw) organic molecules or inorganic molecules including but not limited to salts or metals.

Candidate molecules encompass numerous chemical classes, for example, organic molecules, such as small organic compounds having a molecular weight of more than 50 and less than about 2,500 Daltons. Candidate molecules can comprise functional groups necessary for structural interaction with proteins, particularly hydrogen bonding, and typically include at least an amine, carbonyl, hydroxyl or carboxyl group, and usually at least two of the functional chemical groups. The candidate molecules can comprise cyclical carbon or heterocyclic structures and/or aromatic or polyaromatic structures substituted with one or more of the above functional groups.

A candidate molecule can be a compound in a library database of compounds. One of skill in the art will be generally familiar with, for example, numerous databases for commercially available compounds for screening (see e.g., ZINC database, UCSF, with 2.7 million compounds over 12 distinct subsets of molecules; Irwin and Shoichet (2005) J Chem Inf Model 45, 177-182). One of skill in the art will also be familiar with a variety of search engines to identify commercial sources or desirable compounds and classes of compounds for further testing (see e.g., ZINC database; eMolecules.com; and electronic libraries of commercial compounds provided by vendors, for example: ChemBridge, Princeton BioMolecular, Ambinter SARL, Enamine, ASDI, Life Chemicals etc.).

Candidate molecules for screening according to the methods described herein include both lead-like compounds and drug-like compounds. A lead-like compound is generally understood to have a relatively smaller scaffold-like structure (e.g., molecular weight of about 150 to about 350 kD) with relatively fewer features (e.g., less than about 3 hydrogen donors and/or less than about 6 hydrogen acceptors; hydrophobicity character x log P of about −2 to about 4) (see e.g., Angewante (1999) Chemie Int. ed. Engl. 24, 3943-3948). In contrast, a drug-like compound is generally understood to have a relatively larger scaffold (e.g., molecular weight of about 150 to about 500 kD) with relatively more numerous features (e.g., less than about 10 hydrogen acceptors and/or less than about 8 rotatable bonds; hydrophobicity character x log P of less than about 5) (see e.g., Lipinski (2000) J. Pharm. Tox. Methods 44, 235-249). Initial screening can be performed with lead-like compounds.

When designing a lead from spatial orientation data, it can be useful to understand that certain molecular structures are characterized as being "drug-like". Such characterization can be based on a set of empirically recognized qualities derived by comparing similarities across the breadth of known drugs within the pharmacopoeia. While it is not required for drugs to meet all, or even any, of these characterizations, it is far more likely for a drug candidate to meet with clinical successful if it is drug-like.

Several of these "drug-like" characteristics have been summarized into the four rules of Lipinski (generally known as the "rules of fives" because of the prevalence of the number 5 among them). While these rules generally relate to oral absorption and are used to predict bioavailability of compound during lead optimization, they can serve as effective guidelines for constructing a lead molecule during rational drug design efforts such as may be accomplished by using the methods of the present disclosure.

The four "rules of five" state that a candidate drug-like compound should have at least three of the following characteristics: (i) a weight less than 500 Daltons; (ii) a log of P less than 5; (iii) no more than 5 hydrogen bond donors (expressed as the sum of OH and NH groups); and (iv) no more than 10 hydrogen bond acceptors (the sum of N and O atoms). Also, drug-like molecules typically have a span (breadth) of between about 8 Å to about 15 Å.

Kits

Also provided are kits. Such kits can include an agent or composition described herein and, in certain embodiments, instructions for administration. Such kits can facilitate performance of the methods described herein. When supplied as a kit, the different components of the composition can be packaged in separate containers and admixed immediately before use. Components include, but are not limited to JAK inhibitors and components for delivery of the JAK inhibitor. Such packaging of the components separately can, if desired, be presented in a pack or dispenser device which may contain one or more unit dosage forms containing the composition. The pack may, for example, comprise metal or plastic foil such as a blister pack. Such packaging of the components separately can also, in certain instances, permit long-term storage without losing activity of the components.

Kits may also include reagents in separate containers such as, for example, sterile water or saline to be added to a lyophilized active component packaged separately. For example, sealed glass ampules may contain a lyophilized component and in a separate ampule, sterile water, sterile saline or sterile each of which has been packaged under a neutral non-reacting gas, such as nitrogen. Ampules may consist of any suitable material, such as glass, organic polymers, such as polycarbonate, polystyrene, ceramic, metal or any other material typically employed to hold reagents. Other examples of suitable containers include bottles that may be fabricated from similar substances as ampules, and envelopes that may consist of foil-lined interiors, such as aluminum or an alloy. Other containers include test tubes, vials, flasks, bottles, syringes, and the like. Containers may have a sterile access port, such as a bottle having a stopper that can be pierced by a hypodermic injection needle. Other containers may have two compartments that are separated by a readily removable membrane that upon removal permits the components to mix. Removable membranes may be glass, plastic, rubber, and the like.

In certain embodiments, kits can be supplied with instructional materials. Instructions may be printed on paper or other substrate, and/or may be supplied as an electronic-readable medium, such as a floppy disc, mini-CD-ROM, CD-ROM, DVD-ROM, Zip disc, videotape, audio tape, and the like. Detailed instructions may not be physically associated with the kit; instead, a user may be directed to an Internet web site specified by the manufacturer or distributor of the kit.

Compositions and methods described herein utilizing molecular biology protocols can be according to a variety of standard techniques known to the art (see, e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754; Studier (2005) Protein Expr Purif. 41(1), 207-234; Gellissen, ed. (2005) Production of Recombinant Proteins: Novel Microbial and Eukaryotic Expression Systems, Wiley-VCH, ISBN-10: 3527310363; Baneyx (2004) Protein Expression Technologies, Taylor & Francis, ISBN-10: 0954523253).

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

Citation of a reference herein shall not be construed as an admission that such is prior art to the present disclosure.

Having described the present disclosure in detail, it will be apparent that modifications, variations, and equivalent embodiments are possible without departing the scope of the present disclosure defined in the appended claims. Furthermore, it should be appreciated that all examples in the present disclosure are provided as non-limiting examples.

EXAMPLES

The following non-limiting examples are provided to further illustrate the present disclosure. It should be appreciated by those of skill in the art that the techniques disclosed in the examples that follow represent approaches the inventors have found function well in the practice of the present disclosure, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the present disclosure.

Example 1: Immune Dysregulation Underlies a Subset of Patients with Chronic Idiopathic Pruritus Chronic pruritus is a highly debilitating condition that disproportionately affects the elderly, many of whom experience chronic idiopathic pruritus (CIP), or itch of unknown origin lasting greater than six weeks. Multiple factors are believed to underlie CIP, including aging-associated skin barrier dysfunction, sensory neuropathy, and immunosenescence, the waning of immune function that results in an "allergic," T helper type 2 (Th2) cell response. However, the immunologic profile of CIP patients remains poorly understood.

Figure 2A:
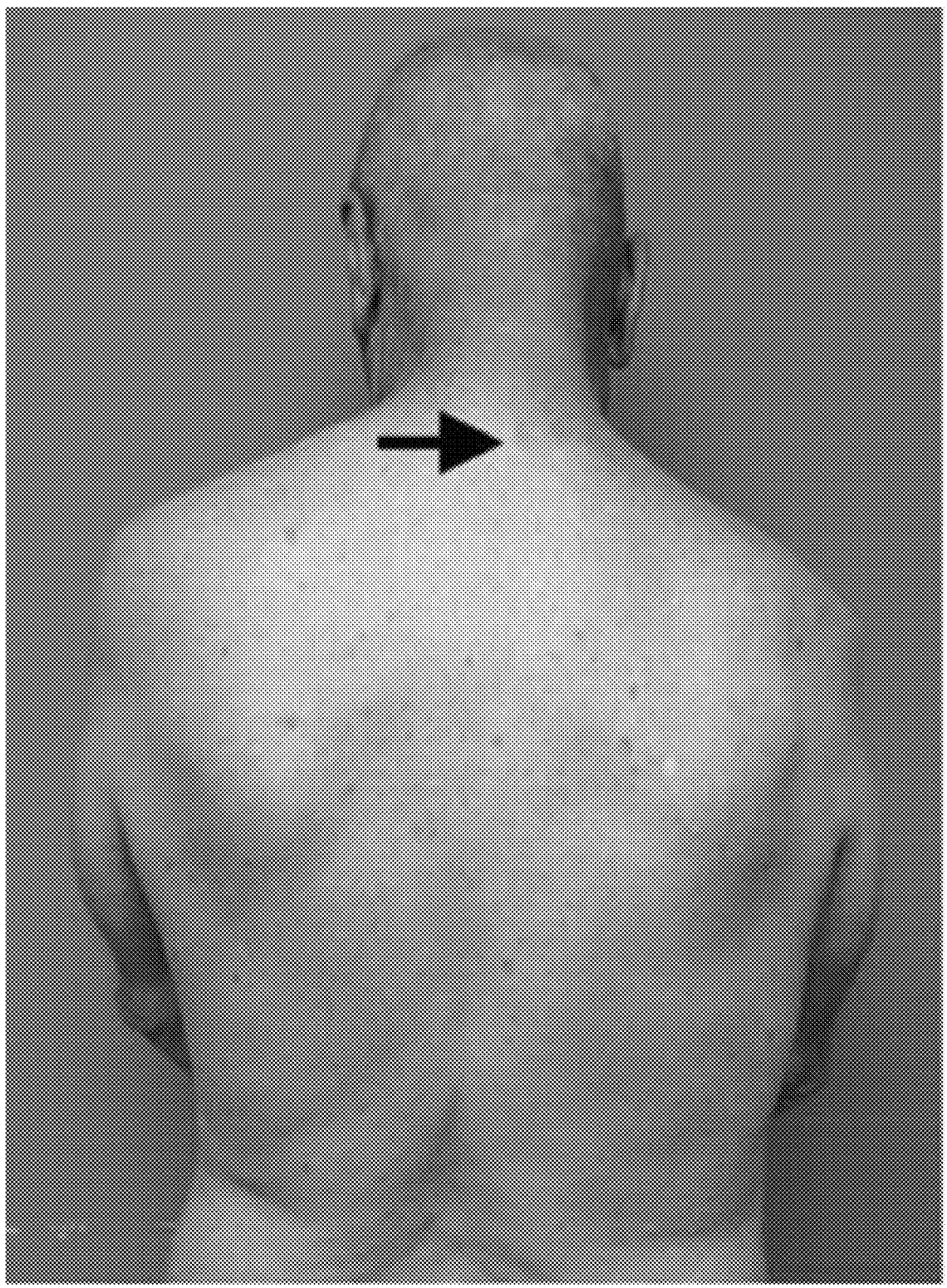
FIG. 2A-C depicts a representative photograph and histopathologic findings on skin biopsy from a subject with CIP.
Figure 2B:
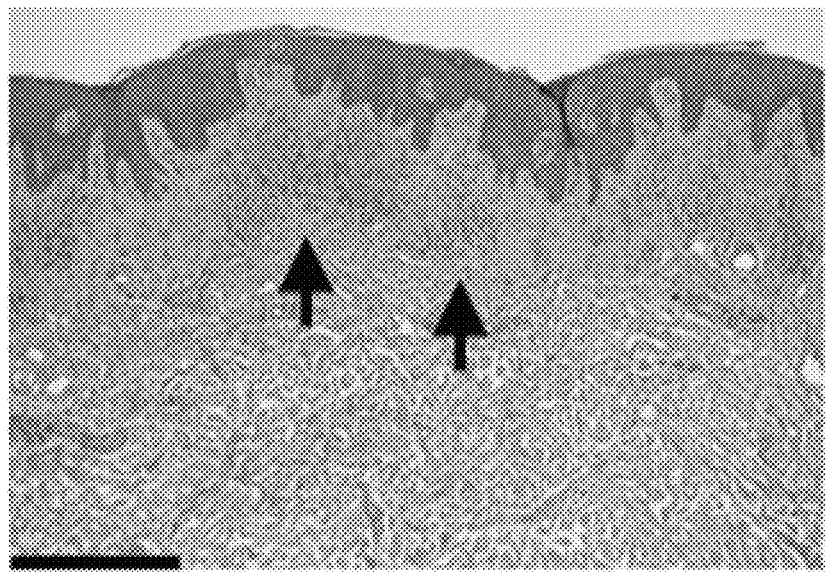
Figure 2C:
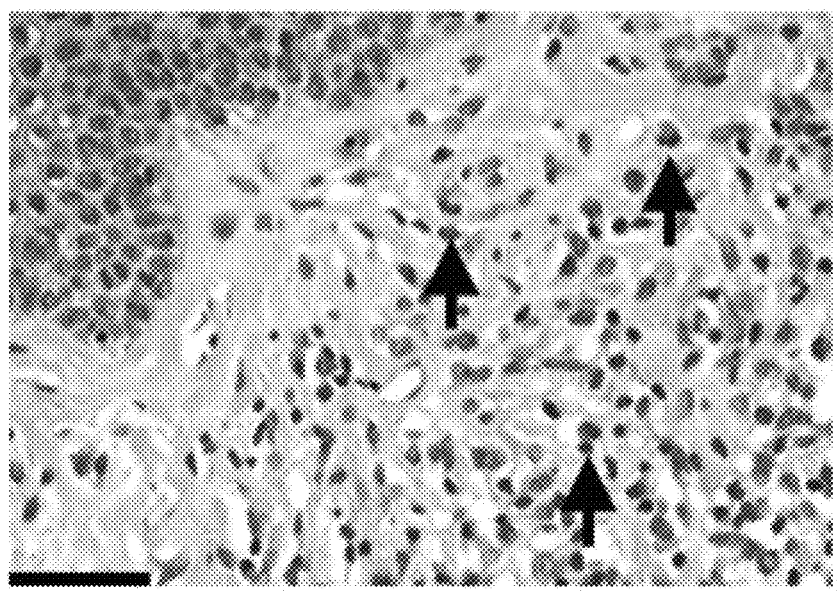
Figure 3A:
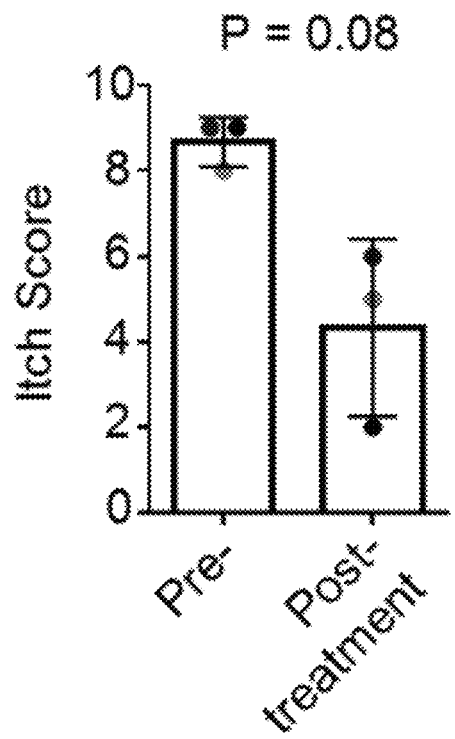
FIG. 3A-B depicts graphs illustrating that administration of a JAK inhibitor to subjects with CIP (n=5) improved their pruritus.
Figure 3B:
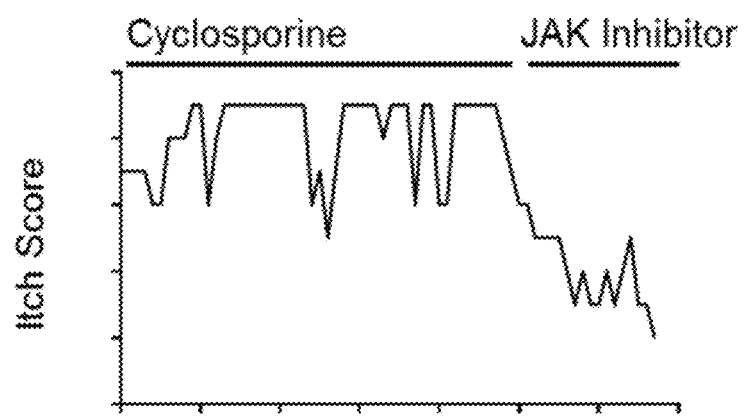
Figure 4:
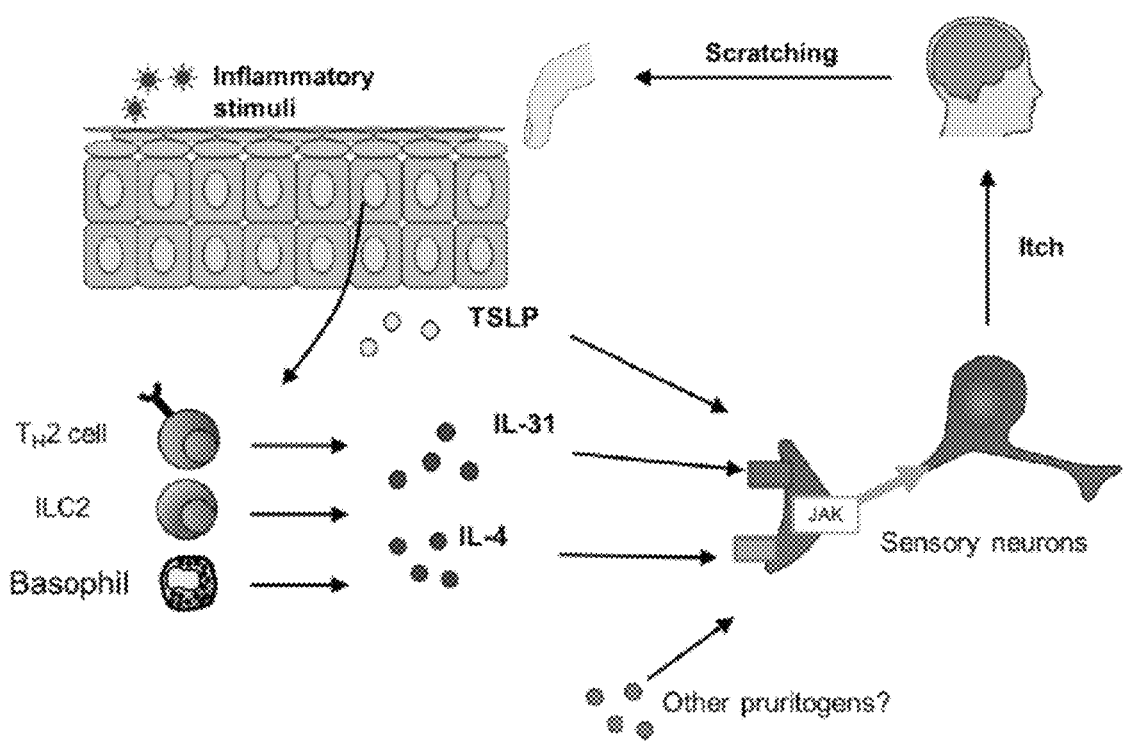
FIG. 4 illustrates a model of JAK-mediated CIP. Multiple cytokines (TSLP, IL-4, IL-31) and other factors (e.g., serotonin, etc.) may act on sensory neurons to mediate itch. However, blockade of a single cytokine may not be sufficient to abate itch. JAK inhibition at the neuronal level may represent a therapeutic strategy to block multiple itch-activating pathways.

This example describes four elderly CIP patients with evidence of marked immune dysregulation after exclusion of other cutaneous and systemic causes of pruritus. Despite the lack of primary dermatologic processes, three out of four patients showed lymphocytic infiltrates on skin biopsy, two of whom demonstrated increased eosinophils (see FIG. 2B and FIG. 2C, and TABLE 2). Immunoglobulin panels and blood flow cytometry revealed previously unrecognized humoral and cellular immune defects, including T and B cell lymphopenia, eosinophilia, and hypogammaglobulinemia (see TABLE 2).

Given the patients' broad immunologic defects, underlying primary immunodeficiencies, like common variable immunodeficiency (CVID), were initially considered. However, the patients' reduced IgG values were not associated with decreases in IgA or IgM, as in CVID. The patients also lacked any history of CVID-associated complications, such as recurrent infections, autoimmunity, and malignancy. These findings suggest that CIP patients may acquire secondary immune defects resembling CVID as a consequence of the aging process.

Immunosenescence results in a loss of T helper type 1 (Th1) cell-driven protective immunity that contributes to skewing towards an allergic, Th2 response. Indeed, the CIP patients exhibited Th2 polarization as evidenced by their elevated serum IgE levels, peripheral eosinophilia, and/or tissue eosinophil infiltration (see TABLE 2). Additionally, their CD8 lymphopenia confirms the loss of Th1 responses, further supporting age-dependent Th2 polarization as a potential contributor to the development of chronic itch. Strikingly, comparison to age-matched control populations indicates that these CIP patients suffer from immunologic imbalances in excess of similarly-aged peers. Three of the four patients' CD8+ T cell counts were significantly reduced in comparison to control subjects of corresponding age; for example, the CD8+ T cell count of 67/mm3 in Case 3 was nearly two standard deviations below the mean reported by Provinciali et al. Likewise, IgG levels for two of the four patients (Cases 1 and 3) fell below the bottom 2.5% described for age-matched controls. These findings suggest that CIP patients may have a greater degree of immune dysfunction that results in an increased susceptibility to chronic pruritus, even above the increased risk already recognized in the elderly.

In conclusion, these CIP patients exhibit immunologic deficits in association with Th2 polarization. These findings suggest aging-associated immunosenescence may promote immune dysregulation that may, in part, explain the increased prevalence of chronic idiopathic pruritus in the elderly. Thus, the restoration of immune homeostasis by recombinant cytokine or immunoglobulin repletion may represent novel therapeutic approaches for CIP.

TABLE 2 Legend: (a) Average and peak Numerical Rating Scale (NRS) itch scores at the time of presentation to our clinic are noted, respectively. (b) A thorough workup was performed to establish the diagnosis of CIP by exclusion of other cutaneous and systemic causes of pruritus, including psychiatric and neurologic conditions, renal failure, biliary dysfunction, thyroid abnormalities, HIV/AIDS, hepatitis B, and hepatitis C. None of the patients had a history of recurrent infections, autoimmune conditions, or malignancy. (c) Notably, a course of oral prednisone prescribed for Case 2's polymyalgia rheumatica improved his muscle weakness but did not resolve his pruritus. (d) Outside of two episodes of septic arthritis arising from knee replacement surgery, the patient had no history of persistent or recurrent infections, autoimmunity, or malignancy. (e) The patient in Case 3 had an initial IgE level of 329 IU/mL, but it normalized to 195 IU/mL two months later.

TABLE 2

Summary of Clinical and Immunologic Characteristics.

| | Reference | Case 1 | Case 2 | Case 3 | Case 4 |
|---|---|---|---|---|---|
| Age | — | 75 | 84 | 77 | 90 |
| Gender | — | M | M | M | M |
| NRS Score[a] | — | 6, 10 | 10, 10 | 8, 10 | 8, 8 |
| Duration of Symptoms (years) | — | 3 | 0.5 | 5 | 4 |
| Past Medical History[b] | — | — | Polymyalgia Rheumatics | Osteoarthritis | — |
| Prior Treatments | — | — | Topical emollients, steroids[c], oral gabaperatin | Topical emollients steroids, oral antihistamines, doxepin, zolpidem | — |
| History of Recurrent Infection, Autoimmunity, or Malignancy? | — | No | No | No[d] | No |
| CBC | | | | | |
| % Lymphocytes | 20-54.3% | 18% ↓ | 8.3% ↓ | 6.8% ↓ | 18.2% ↓ |
| Abs Eosinophil Count (K/mm³) | 0-0.5 | 1.8 | Normal | 1.3 | 1.8 |
| Diagnostic Testing | | | | | |
| SPEP | — | Normal | — | Normal | — |
| CXR | — | — | — | Normal | Nonspecific calcifications |
| CT Scan | — | Normal | — | — | — |
| Bone Marrow Biopsy | — | Normal | — | — | Normal |
| Skin Biopsy | — | Sparse superficial perivascular lymphocytic infilterate | Dermal edema with minimal inflammation | Superficial perivascular lymphocytic inflammation with abundant eosinophils | Spongiosis with lichenoid infiltrates and eosinophils |
| Immunoglobulin Panel | | | | | |
| IgM (mg/dL) | 30-210 | 61.5 | 122 | 52.1 | <19.0 ↓ |
| IgG (mg/dL) | 700-1450 | 512 ↓ | 619 ↓ | 552 ↓ | 750 |

TABLE 2-continued

Summary of Clinical and Immunologic Characteristics.

|  | Reference | Case 1 | Case 2 | Case 3 | Case 4 |
|---|---|---|---|---|---|
| IgA (mg/dL) | 70-370 | 212 | 167 | 85.7 | 525 ↑ |
| IgE (IU/mL) | 0-250 | 448 ↑ | 1940 ↑ | 329[e] ↑ | 24.7 |
| Flow Cytometry Panel | | | | | |
| Abs CD8+ Count (#/mm$^3$) | 211-977 | 359 | 60 ↓ | 67 ↓ | 96 ↓ |
| Abs CD4+ Count (#/mm$^3$) | 393-1607 | 718 | 360 ↓ | 233 ↓ | 654 |
| Abs CD19+ Count (#/mm$^3$) | 70-545 | 87 ↓ | 240 | 4 ↓ | 48 ↓ |
| Abs CD3+ Count (#/mm$^3$) | 706-2482 | 1076 | 420 ↓ | 300 ↓ | 760 |

[a]Average and peak Numerical Rating Scale (NRS) itch scores at the time of presentation to our clinic are noted, respectively.
[b]A thorough workup was performed to establish the diagnosis of CIP by exclusion of other cutaneous and systemic causes of pruritus, including psychiatric and neurologic conditions, renal failure, biliary dysfunction, thyroid abnormalities, HIV/AIDS, hepatitis B, and hepatitis C. None of the patients had a history of recurrent infections, autoimmune conditions, or malignancy.
[c]Notably, a course of oral prednisone prescribed for Case 2's polymyalgia rheumatica improved his muscle weakness but did not resolve his pruritus.
[d]Outside of two episodes of septic arthritis arising from knee replacement surgery, the patient had no history of persistent of recurrent infections, autoimmunity, or malignancy.
[e]The patient in Case 3 had a initial IgE level of 329 IU/mL, but it normalized to 195 IU/mL two months later.

Figures 5A, 5B, 5C, 5D, 5E, 5F, 5G, 5H, 5I:
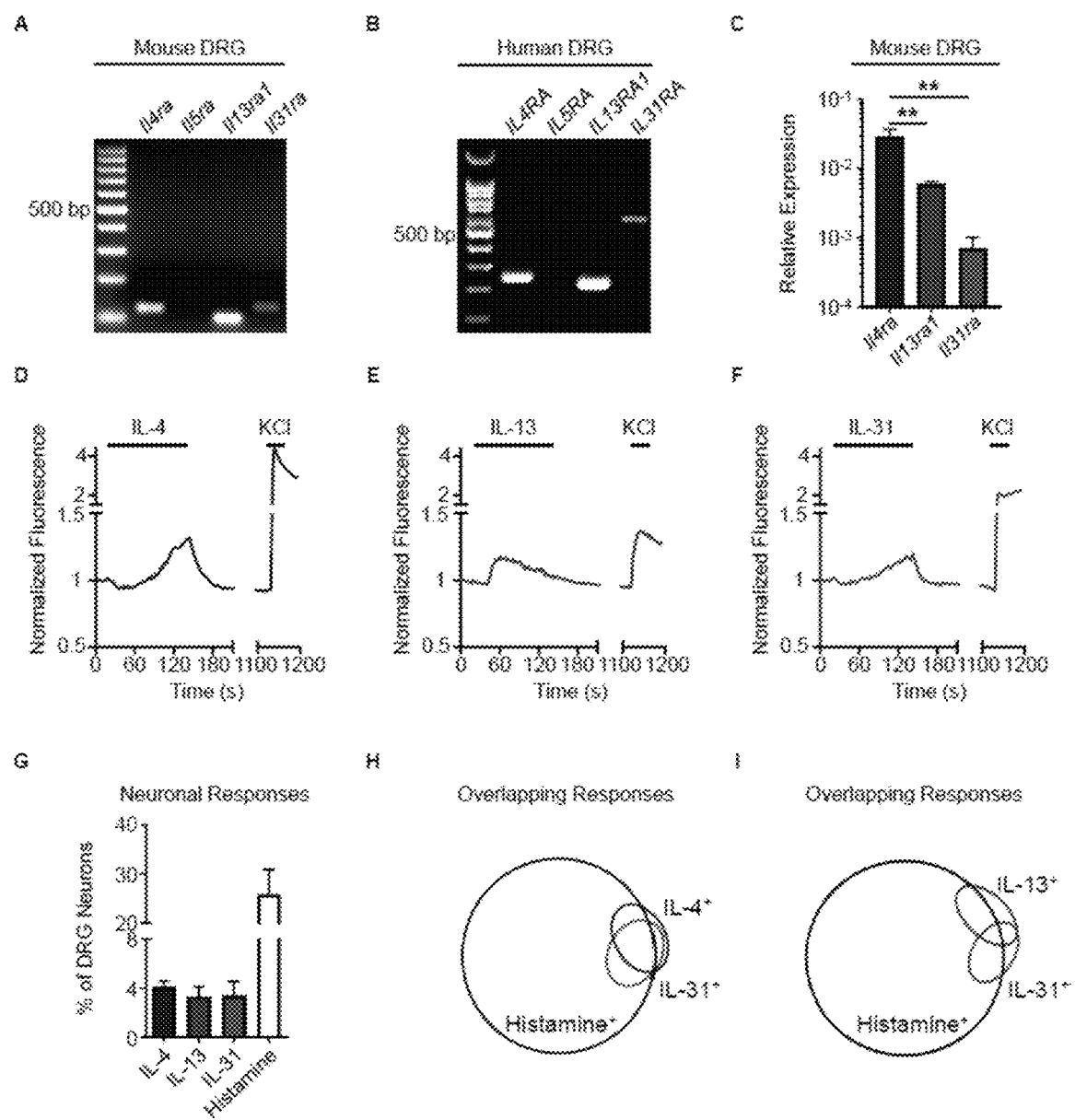
FIG. 5A-FIG. 5I shows type 2 cytokines directly activate itch-sensory pathways.

Example 2: Sensory Neurons Respond to Type 2 Cytokines Along Itch-Sensory Pathways The proinflammatory type 2 cytokines IL-4, IL-5, and IL-13 are known to promote atopic dermatitis (AD) pathogenesis (Gittler et al., 2012; Weidinger and Novak, 2016). Importantly, Phase II and III clinical trials employing dupilumab, an IL-4/13 receptor (IL-4Rα) antagonist, to suppress allergic inflammation in AD patients demonstrated remarkable improvement in both disease and itch severity (Beck et al., 2014; Simpson et al., 2016; Thaçi et al., 2016). Although IL-4/13-dependent inflammatory processes are well-established mediators of skin inflammation in AD, it is not known whether these cytokines directly promote chronic itch. To examine whether type 2 cytokines can directly activate sensory neurons, we performed RT-PCR of dorsal root ganglia (DRG) from wild type (WT) mice and found expression of IL-4Rα (Il4ra) and IL-13 receptor alpha 1 (IL-13Rα1; Il13ra1), but not IL-5 receptor alpha (IL-5Rα; Il5ra) (see e.g., FIG. 5A). As expected, we were also able to detect expression of the receptor for the known cytokine pruritogen IL-31 (Il31ra) (see e.g., FIG. 5A) (Cevikbas et al., 2014; Dillon et al., 2004; Sonkoly et al., 2006). Similarly, DRG from human cadaveric donors also expressed IL-4Rα (IL4RA), IL-13Rα1 (IL13RA1), and IL-31RA (IL31RA), but not IL-5Rα (IL5RA) (see e.g., FIG. 5B). Strikingly, we found that sensory ganglia express much higher levels of Il4ra compared to Il13ra1 and Il31ra (see e.g., FIG. 5C). Taken together, these findings provoke the hypothesis that sensory neurons can be directly stimulated by the type 2 cytokines IL-4 and IL-13.

Figure 12:
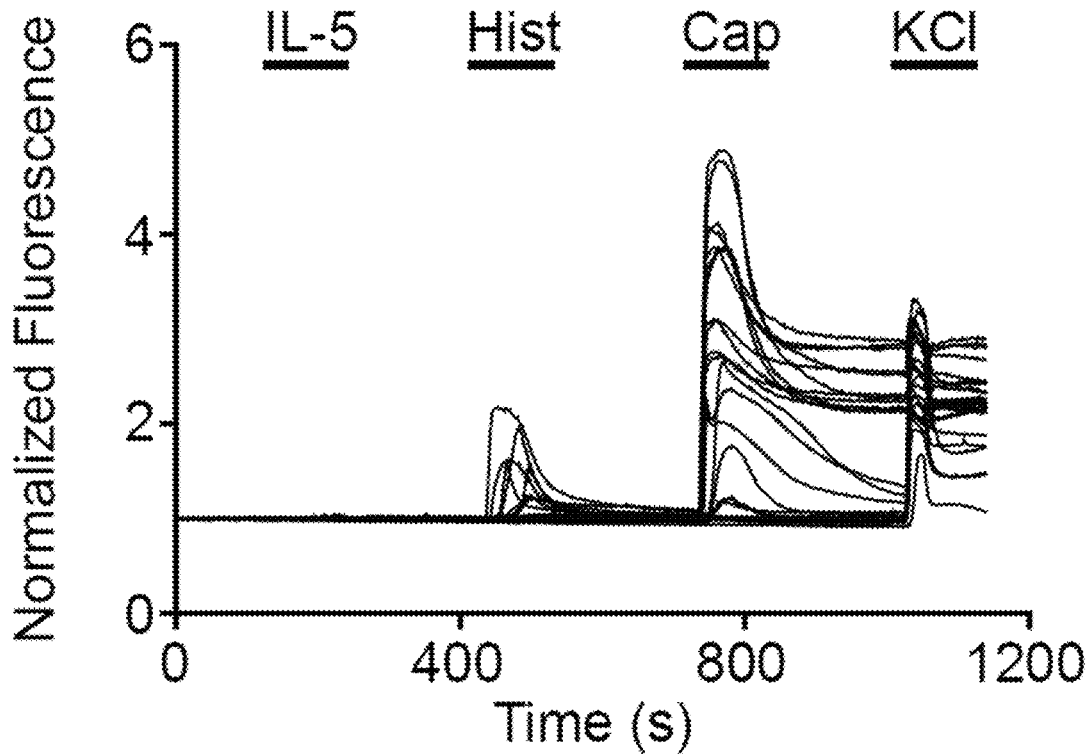
FIG. 12 shows IL-5 does not activate DRG neurons. Relates to FIG. 5. Representative calcium imaging traces of mouse DRG neurons challenged with recombinant murine IL-5, histamine (Hist), capsaicin (Cap), and potassium chloride (KCl), n>300 neurons.

To test whether sensory neurons can be activated by type 2 cytokines, we employed ratiometric calcium imaging of murine DRG neurons. Ex vivo stimulation of cultured neurons with recombinant murine IL-4 (see e.g., FIG. 5D) or IL-13 (see e.g., FIG. 5E) demonstrated a rapid rise of intracellular calcium in a subset of neurons. These responses were similar to those observed with IL-31 stimulation (see e.g., FIG. 5F). We next sought to comprehensively examine the composition of IL-4- and IL-13-responsive neurons in the DRG. Stimulation of cultured neurons with IL-4 or IL-13 led to calcium responses in 4.1±0.5% and 3.3±0.8% of total DRG neurons, respectively (see e.g., FIG. 5G). Consistent with previous reports (Cevikbas et al., 2014; Liu et al., 2009), approximately 5% and 25% of neurons were responsive to IL-31 and histamine, respectively (see e.g., FIG. 5G). As expected given the lack of expression of Il5ra in the DRG (see e.g., FIG. 5A-B), no responses were seen when DRG neurons were stimulated with IL-5 (see e.g., FIG. 12). Collectively, these studies demonstrate that sensory neurons respond selectively to the type 2 cytokines IL-4 and IL-13.

We next performed calcium imaging of DRG neurons in response to successive challenges with defined pruritogens to examine whether IL-4 or IL-13 activate previously defined itch-sensory pathways. When DRG neurons were serially stimulated with IL-4, as well as with IL-31 and histamine, 88.9% of IL-4-responsive neurons also responded to IL-31 or histamine (see e.g., FIG. 5H). Similarly, 75.0% of IL-13-responsive neurons also responded to IL-31 or histamine (see e.g., FIG. 5I). Together, these studies indicate that both IL-4 and IL-13 can activate families of neurons that include previously defined itch-sensory pathways. However, we note that both IL-4 and IL-13 can also activate sensory neurons that do not respond to either IL-31 or histamine.

Figure 13:
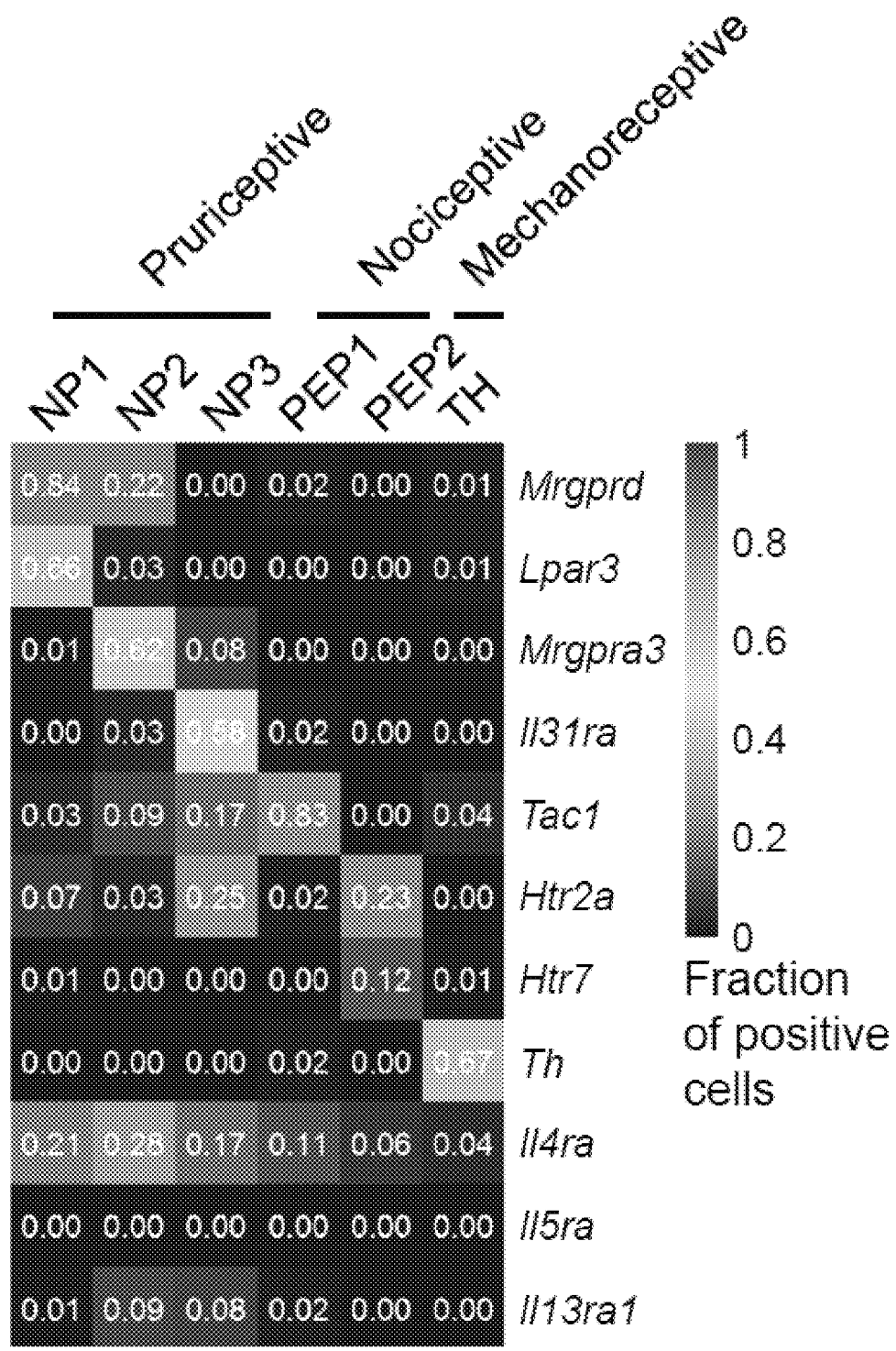
FIG. 13 shows predicted pruriceptive pathways are enriched in neurons expressing type 2 cytokine receptors compared to other predicted sensory modalities. Relates to FIG. 5. Expression profile within mouse DRG neurons at the single cell level of cluster-defining and selected itch-related genes for predicted sensory modalities. Numbers in heat map indicate fraction of positive cells by thresholding method. Full dataset and methods available in Usoskin et al., 2015.
Figure 14:
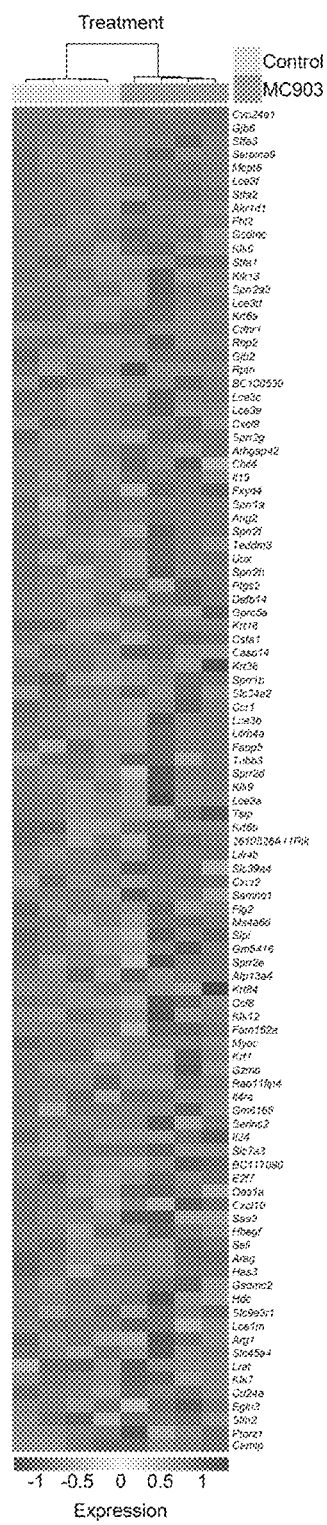
FIG. 14 shows MC903 treatment results in inflammatory changes in the skin also observed in human atopic dermatitis (AD). Relates to FIG. 6. Comparison of gene row Z-scores of regularized logarithm expression value of the top 100 differentially expressed genes in the skin of MC903-treated mice compared to controls determined by p-value. Genes are listed based on increasing adjusted p-value.

To validate our findings at the single-cell level, we reanalyzed a previously published single-cell RNA-sequencing data set that correlated the transcriptional profile of single neurons to predicted sensory modalities in mice (Usoskin et al., 2015). Reexamination of this data set revealed that the families of small diameter neurons predicted to mediate itch (NP1, NP2, and NP3) are enriched in neurons that express Il4ra and Il13ra1 compared to other families of small diameter neurons predicted to mediate nociception (PEP1 and PEP2) and mechanoreception (TH) (see e.g., FIG. 13). Although previously defined pruriceptors such as Mas-related G protein-coupled receptor A3 (MrgprA3) and IL-31RA are highly specific to defined itch clusters such as NP2 and NP3, respectively (Usoskin et al., 2015), the expression of Il4ra spans multiple pruriceptive clusters (see e.g., FIG. 13). These analyses and our functional calcium imaging findings indicate that type 2 cytokines can activate multiple itch-sensory pathways simultaneously. Collectively, these studies provoke the hypothesis that type 2 cytokines promote chronic itch via direct stimulation of neurons in addition to their well-defined effects on immune cells.

Figures 6A, 6B, 6C, 6D, 6E, 6F:
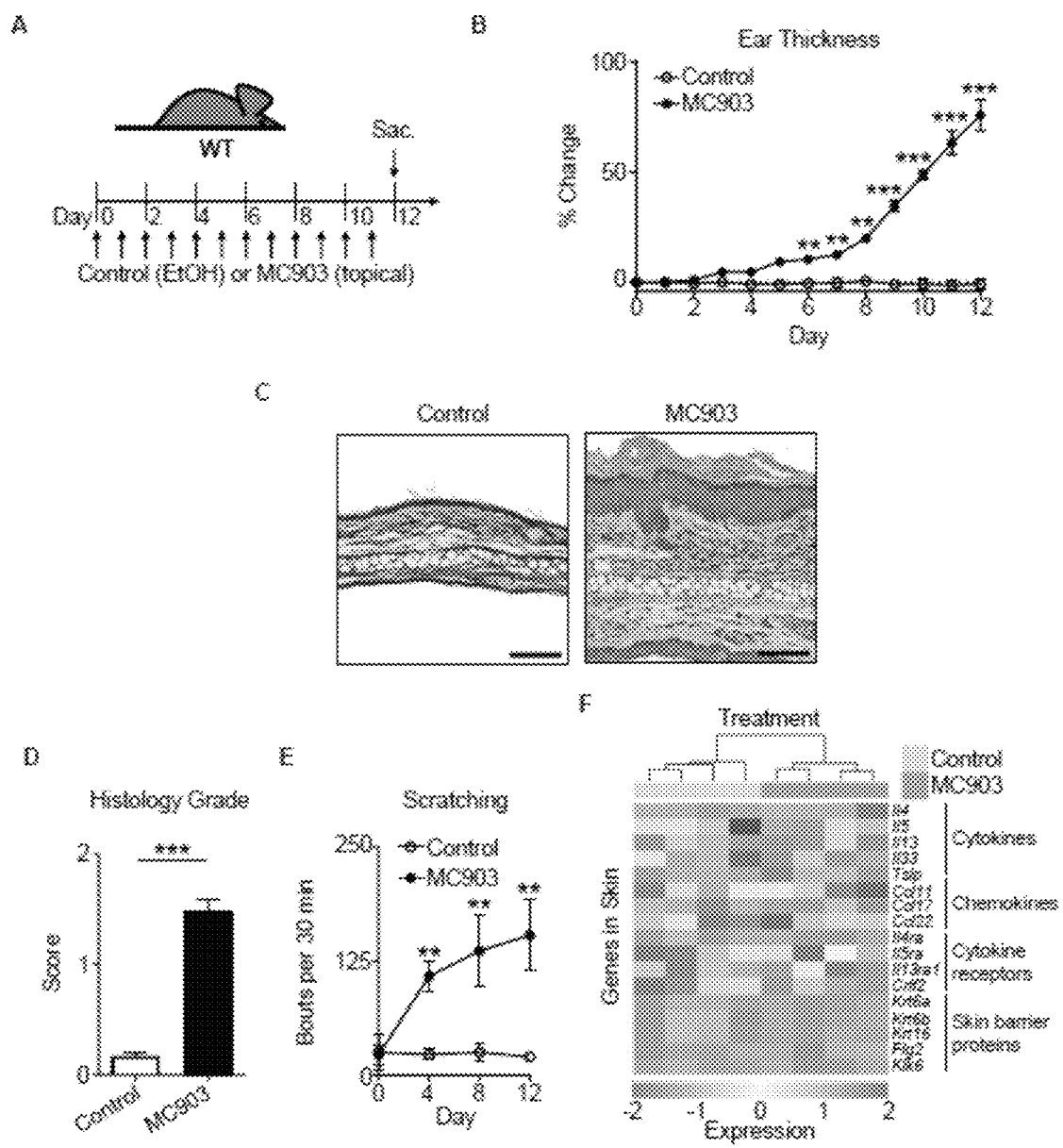
FIG. 6A-FIG. 6G shows chronic itch is associated with enhanced expression of type 2 cytokine receptors in sensory ganglia.

Example 3: Type 2 Cytokine Receptor Expression is Enhanced in Sensory Ganglia in the Setting of Chronic Itch To explore the contribution of type 2 cytokines to itch in vivo, we employed a previously established murine model of atopic dermatitis (AD)-like skin inflammation in which mice are treated with the topical irritant calcipotriol (MC903) (see e.g., FIG. 6A) (Kim et al., 2013a, 2014, Li et al., 2006, 2009; Morita et al., 2015; Noti et al., 2013, 2014; Siracusa et al., 2011). Compared to control mice treated with vehicle only (ethanol, EtOH), MC903-treated mice develop robust skin inflammation as measured by ear skin thickening (see e.g., FIG. 6B) and histologic features of inflammation including stratum corneum thickening (hyperkeratosis), epidermal hyperplasia (acanthosis), and a mixed dermal inflammatory infiltrate (see e.g., FIG. 6C). Accordingly, using a previously established histopathology grading system (Kim et al., 2014), we found that MC903-treated mice exhibit a higher histologic score of inflammation (see e.g., FIG. 6D). Importantly, in addition to features of skin inflammation, MC903-treated mice demonstrate a marked chronic itch phenotype as measured by quantifying scratching bouts over time (see e.g., FIG. 6E).

Figure 6G:
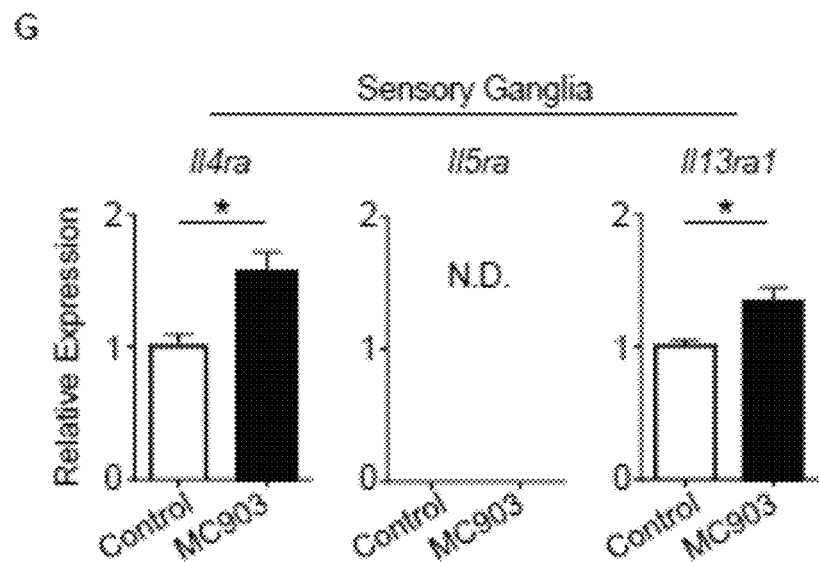

To comprehensively examine the inflammatory changes induced in the setting of AD-associated chronic itch, we performed RNA-sequencing of skin samples from both control and MC903-treated mice. As expected, skin from MC903-treated mice demonstrated a distinct transcriptional program compared to control skin including upregulation of key AD-associated cytokine signaling molecule transcripts such as IL-4 (Il4), IL-13 (Il13), IL-4R$\alpha$ (Il4ra), and IL-13R$\alpha$1 (Il13ra1) (see e.g., FIG. 6F, see e.g., FIG. 15). Further, expression of Il4ra and Il13ra1, but not Il5ra, were also significantly upregulated in sensory ganglia from mice with AD-associated itch (see e.g., FIG. 6G). Thus, these data suggest that the sensory nervous system can selectively enhance type 2 cytokine signaling via upregulation of receptors for both IL-4 and IL-13 in the setting of chronic itch and provoke the hypothesis that dysregulated type 2 cytokine signaling in sensory neurons promotes pathologic chronic itch.

Example 4: Type 2 Immune Cells Directly Interact with Sensory Nerve Fibers

Figures 7A, 7B, 7C:
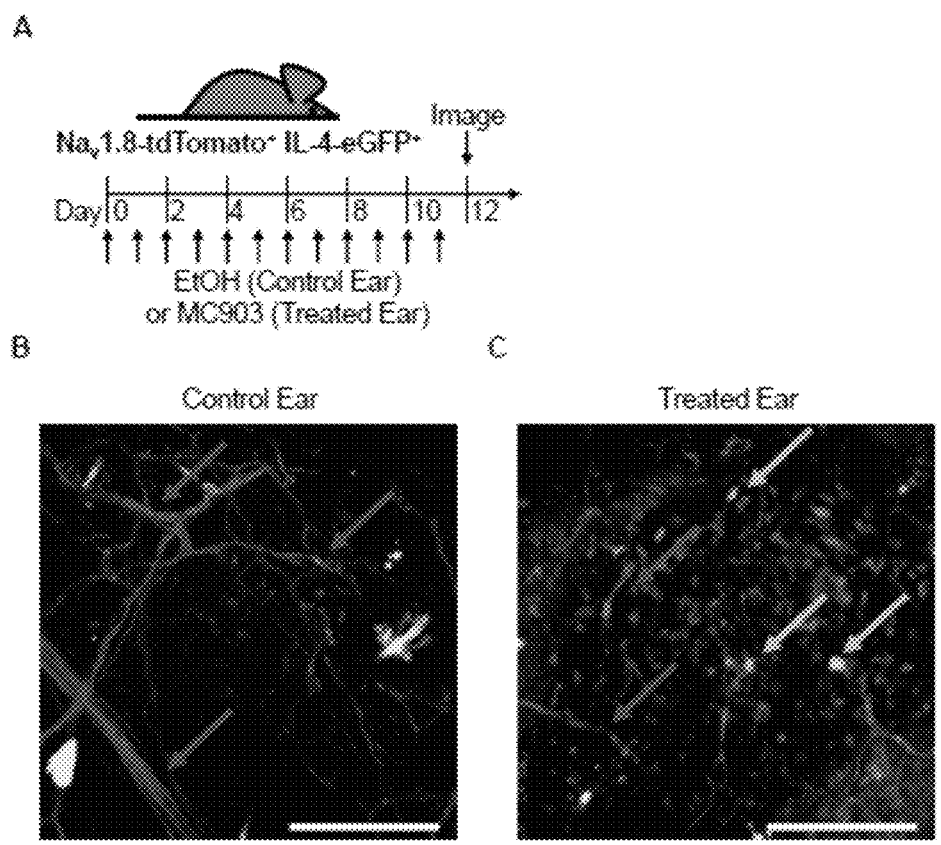
FIG. 7A-FIG. 7E shows type 2 immune cells interact with sensory nerve fibers in the skin.
Figures 7D, 7E:
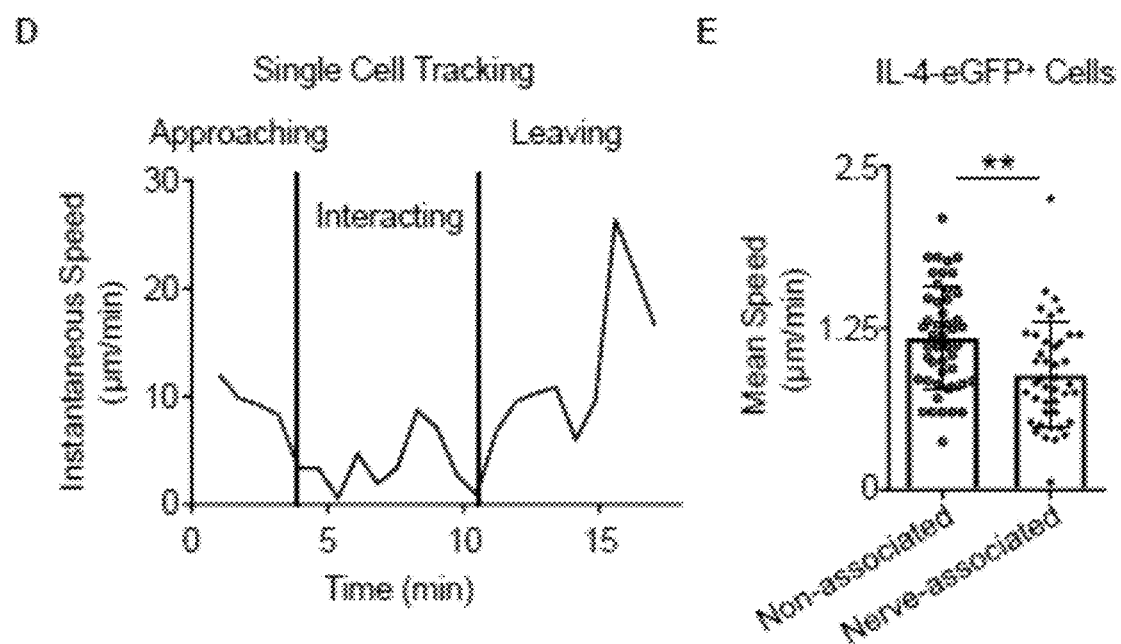
Figure 16:
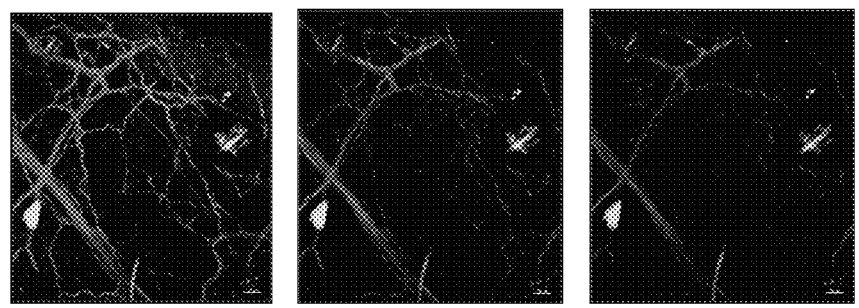
FIG. 16 are stills of a movie showing control treatment results in few type 2 immune cells in the skin. Relates to FIG. 7. Representative time-lapse movie of intravital two-photon imaging of a $Na_v1.8$-tdTomato$^+$ IL-4-eGFP$^+$ control ear. Movie shows few IL-4-eGFP$^+$ cells in the ear skin.
Figure 17:
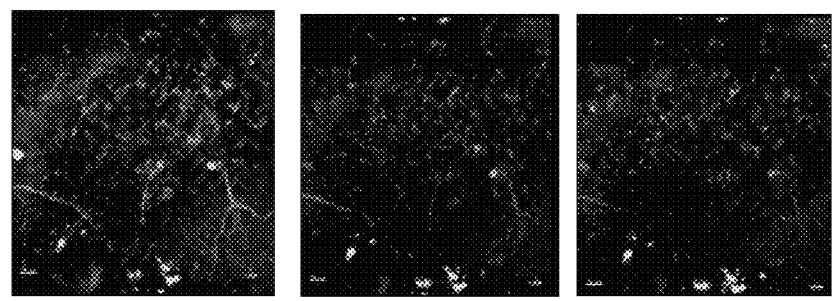
FIG. 17 are stills of a movie showing MC903 treatment results in many type 2 immune cells near sensory nerve fibers in the skin. Relates to FIG. 6. Representative time-lapse movie of intravital two-photon imaging of a $Na_v1.8$-tdTomato$^+$ IL-4-eGFP$^+$ MC903-treated ear. Movie shows many IL-4-eGFP$^+$ cells near sensory nerve fibers in the ear skin.
Figure 18:
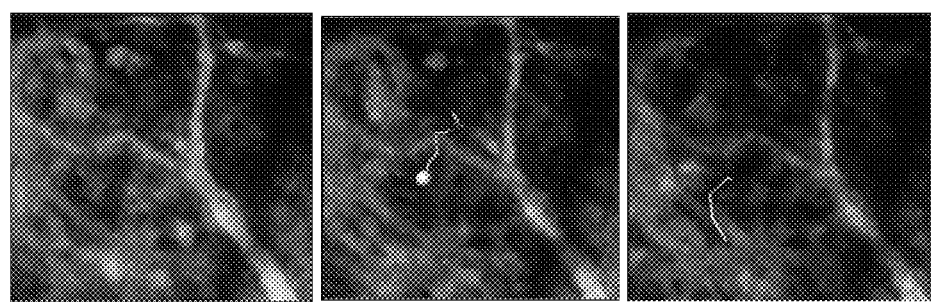
FIG. 18 are stills of a movie showing type 2 immune cells interact with sensory nerve fibers in the skin. Relates to FIG. 7. Representative time-lapse movie of intravital two-photon imaging of a $Na_v1.8$-tdTomato$^+$ IL-4-eGFP$^+$ MC903-treated ear demonstrating an example track of an IL-4-eGFP$^+$ cell approaching a sensory nerve fiber, interacting with it, then leaving the area of the fiber.

To examine whether type 2 cytokine-expressing cells come into close proximity with sensory nerve fibers innervating the skin, we generated novel dual reporter mice in which sensory nerve fibers express tdTomato under a sensory neuron-specific (Na$_v$1.8) Cre recombinase (Agarwal et al., 2004) and type 2 immune cells express enhanced GFP (eGFP) under an IL-4 reporter (Mohrs et al., 2001). Therefore, these dual reporter mice allowed us to visualize whether type 2 immune cells (IL-4-eGFP$^+$) interact with sensory nerve fibers (Na$_v$1.8-tdTomato$^+$). We then treated these dual reporter mice with vehicle control (EtOH) on one ear and MC903 on the second ear and performed live intravital two-photon imaging of the skin of both ears (see e.g., FIG. 7A) (Zinselmeyer et al., 2009). Although we observed very few IL-4-eGFP$^+$ cells in the control skin (see e.g., FIG. 7B, FIG. 16), we found many motile type 2 immune cells in close proximity to sensory nerve fibers in MC903-treated skin (see e.g., FIG. 7C, FIG. 17). At the single cell level, we observed that a subset of type 2 immune cells markedly reduced their instantaneous speed upon interacting with a sensory nerve fiber but resumed rapid transit after leaving the fiber (see e.g., FIG. 7D, FIG. 18). Overall, we found that IL-4-eGFP$^+$ type 2 immune cells associated with Na$_v$1.8-tdTomato$^+$ sensory nerve fibers had a lower mean speed over the course of imaging compared to those that were not in association with sensory fibers (see e.g., FIG. 7E). Taken together, these findings suggest the existence of robust bidirectional interactions between the immune and sensory nervous systems that result in both altered immune cell trafficking and activation of sensory fibers. The observation that type 2 immune cells physically interact with sensory fibers in vivo lends further support to the hypothesis that type 2 cytokine signaling may mediate chronic itch via direct neuronal stimulation.

Figures 8A, 8B, 8C, 8D, 8E, 8F:
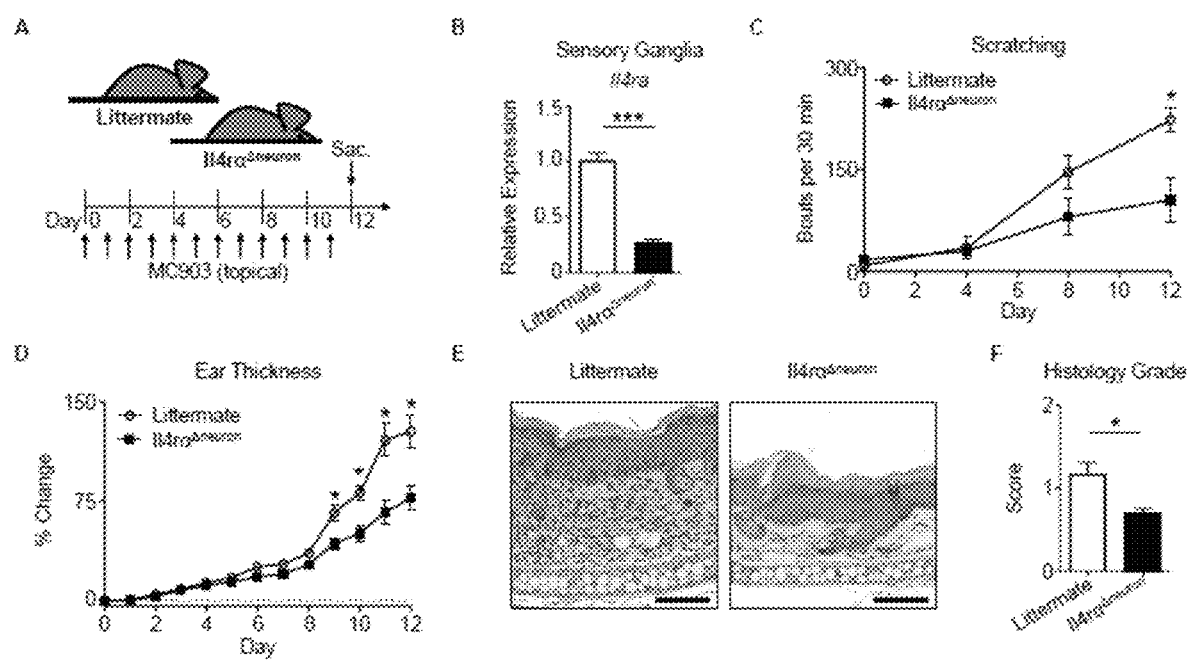
FIG. 8A-FIG. 8F shows neuronal IL-4Rα expression is necessary for chronic itch.

Example 5: Neuronal Type 2 Cytokine Signaling is Necessary for the Development of Chronic Itch To investigate the in vivo functions of sensory neuron-intrinsic type 2 cytokine signaling, we generated mice that lack IL-4R$\alpha$ specifically on sensory neurons using the Na$_v$1.8-Cre mice (Na$_v$1.8-Cre$^+$ Il4ra$^{fl/fl}$, IL-4R$\alpha^{\Delta neuron}$) (see e.g., FIG. 8A). IL-4R$\alpha^{\Delta neuron}$ mice were born at normal Mendelian frequencies, and deletion of Il4ra was confirmed in sensory ganglia (see e.g., FIG. 8B). We then treated IL-4R$\alpha^{\Delta neuron}$ mice with MC903 to explore the direct neuronal contributions of IL-4/13 signaling to chronic itch (see e.g., FIG. 8A). Strikingly, upon induction of skin inflammation, IL-4R$\alpha^{\Delta neuron}$ mice demonstrated a significant reduction in scratching bouts over time in comparison to littermate controls (see e.g., FIG. 8C). Additionally, skin inflammation was markedly reduced as determined by ear thickness measurements (see e.g., FIG. 8D) and histopathologic assessment (see e.g., FIG. 8E-F). Taken together, these studies demonstrate that previously unrecognized sensory neuron-restricted IL-4R$\alpha$ signaling is critical for both the elicitation of chronic itch as well as the development of skin inflammation.

Example 6: Disruption of Neuronal JAK1 Signaling Reduces Chronic Itch

Figures 9A, 9B, 9C, 9D, 9E, 9F, 9G, 9H:
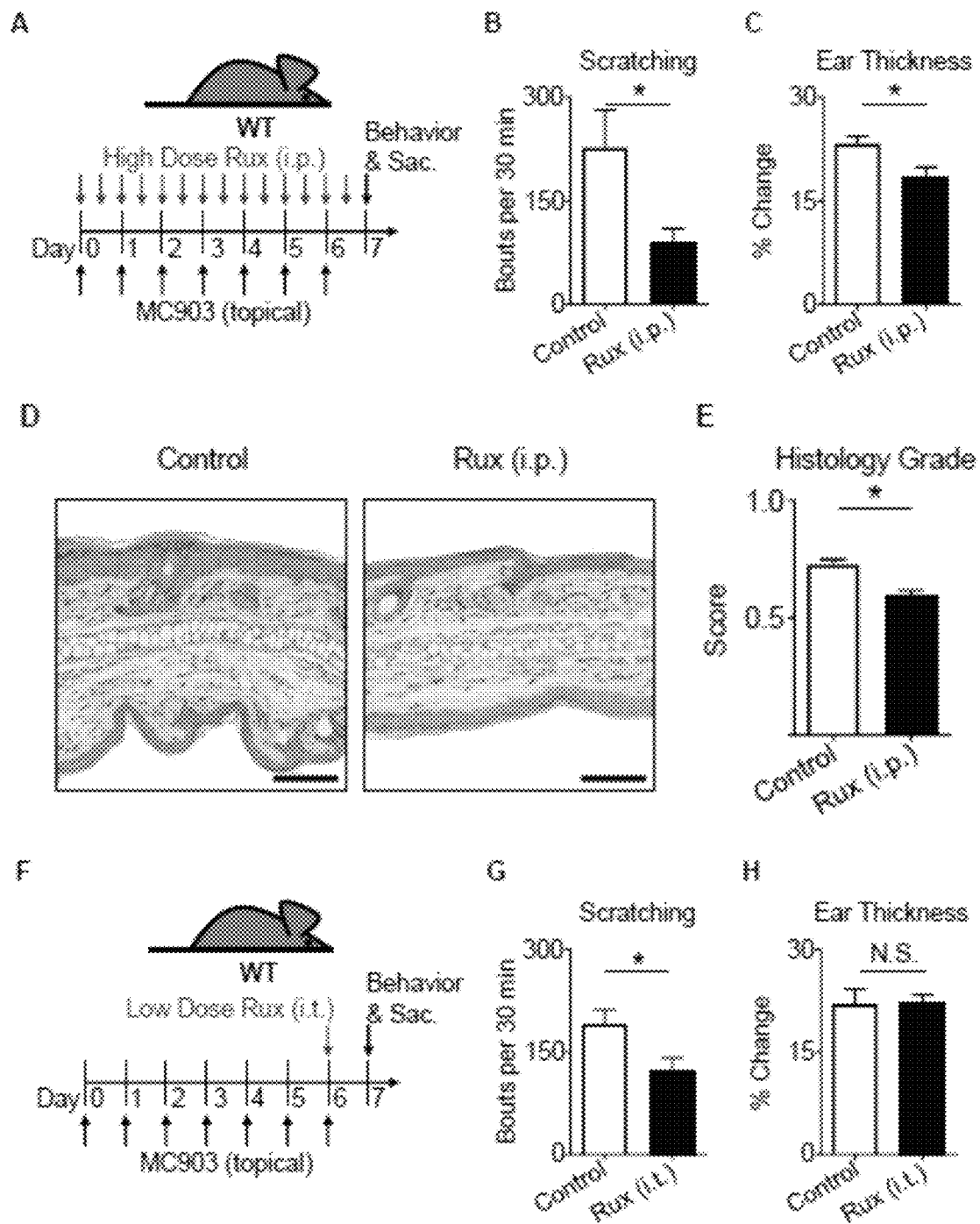
FIG. 9A-FIG. 9O shows disruption of neuronal JAK1 reduces chronic itch.
(FIG. 9B) Scratching behavior, (FIG. 9C) ear thickness measurement, (FIG. 9D) representative histopathology, and (FIG. 9E) histology score of i.p. control and rux-treated mice on Day 7, n≥10 mice per group.
(FIG. 9F) Experimental schematic indicating single intrathecal (i.t.) injection of control vehicle or low dose rux (10 µg) 24 hours before behavioral assays of MC903-treated WT mice.
(FIG. 9G) Scratching behavior, (FIG. 9H) ear thickness measurement, (FIG. 9I) representative histopathology, and (FIG. 9J) histology score of i.t. control and rux-treated mice on Day 7, n 10 mice per group.

Given that type 2 cytokines are known to signal through JAK-dependent pathways in immune cells (Kelly-Welch et al., 2003; Schwartz et al., 2016), we sought to confirm that sensory neurons express JAK signaling components at the single cell level. To examine this, we again reanalyzed a previously published data set of single-cell RNA-sequencing of DRG neurons (Usoskin et al., 2015) and identified that JAK1 is highly expressed in pruriceptive neurons (see e.g., FIG. 15). Thus, we hypothesized that JAK inhibition may represent a novel therapeutic strategy for chronic itch. To test whether pharmacologic inhibition of JAK signaling in vivo would reduce itch, we employed MC903 treatment to induce AD-associated itch in WT mice while concurrently treating with the JAK inhibitor ruxolitinib (see e.g., FIG. 9A). Indeed, systemic intraperitoneal (i.p.) delivery of ruxolitinib significantly reduced scratching bouts in MC903-treated mice (see e.g., FIG. 9B). Surprisingly, we observed that ear skin thickening (see e.g., FIG. 9C) and histologic parameters of disease (see e.g., FIG. 9D-E) demonstrated a statistically significant, but only slight, reduction in the setting of systemic ruxolitinib treatment despite its well-established anti-inflammatory properties. Thus, we speculated that the anti-itch effects of ruxolitinib may be mediated predominantly through direct neuronal JAK inhibition rather than through suppression of skin inflammation.

Figures 9I, 9J, 9K, 9L, 9M, 9N, 9O:
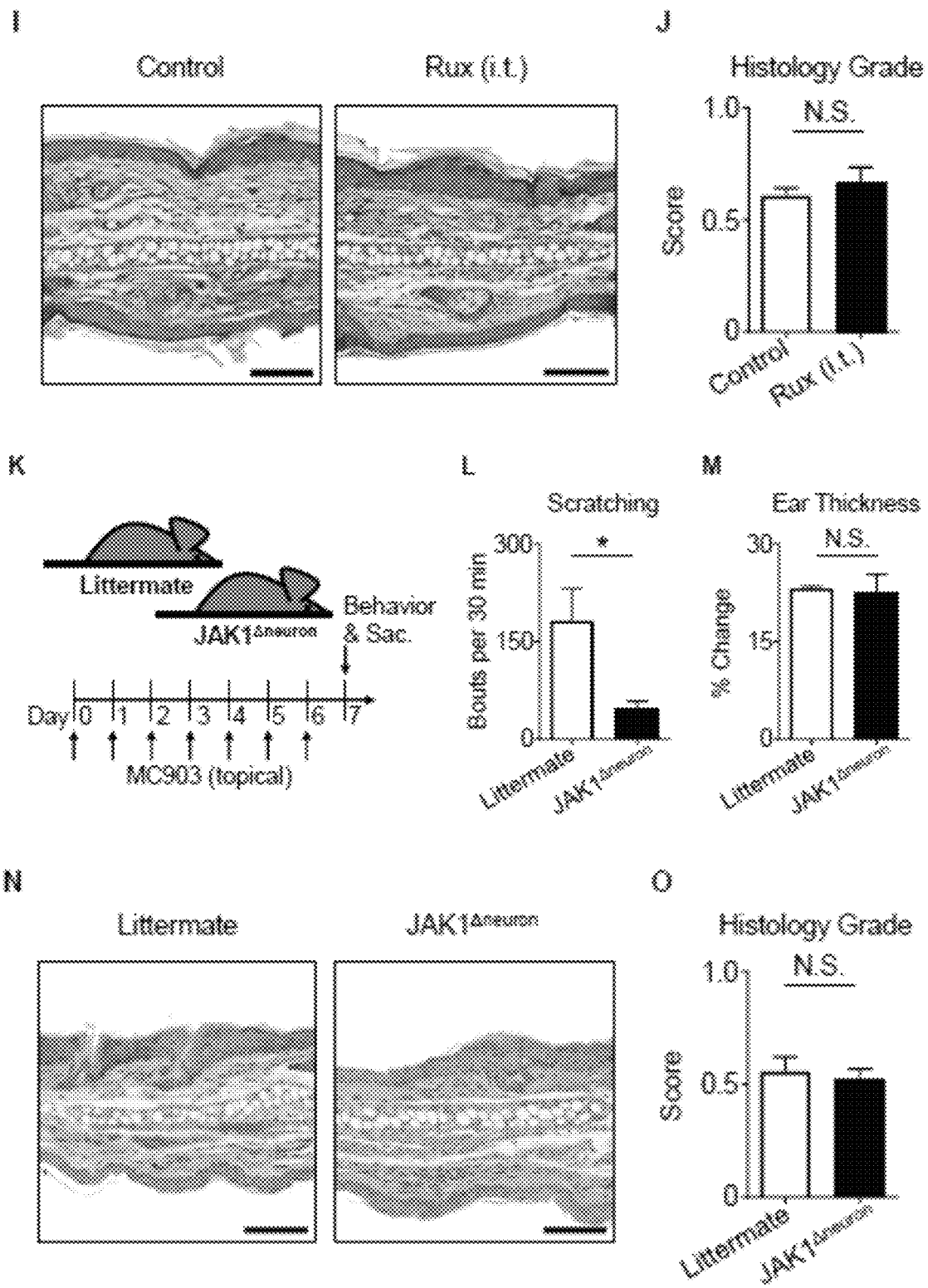
(FIG. 9K) Experimental schematic indicating MC903 treatment of JAK1$^{\Delta neuron}$ and littermate control mice.
(FIG. 9L) Scratching behavior, (FIG. 9M) ear thickness measurement, (FIG. 9N) representative histopathology, and (FIG. 9O) histology score of JAK1$^{\Delta neuron}$ mice compared to littermate controls on Day 7, n≥8 per group. Scale bars indicate 100 µm. Data are represented as mean±SEM. See also FIG. 15.

To test whether JAK blockade in the neuronal compartment alone would be sufficient to reduce chronic itch, we induced AD-like itch with MC903 in WT mice and delivered a single low dose of ruxolitinib intrathecally (i.t.) (see e.g., FIG. 9F). Strikingly, mice that received i.t. ruxolitinib demonstrated marked reduction in scratching bouts 24 hours following a single injection (see e.g., FIG. 9G), despite no effect on peripheral skin inflammation (see e.g., FIG. 9H-J). Thus, pharmacologic JAK blockade limited to the nervous system was sufficient to abate itch. Taken together, these studies demonstrate that JAK inhibition represents a viable therapeutic strategy for chronic itch. Further, these observations provoke the hypothesis that JAK signaling in sensory neurons is a key mechanism by which chronic itch is mediated independently of skin inflammation.

Figure 15:
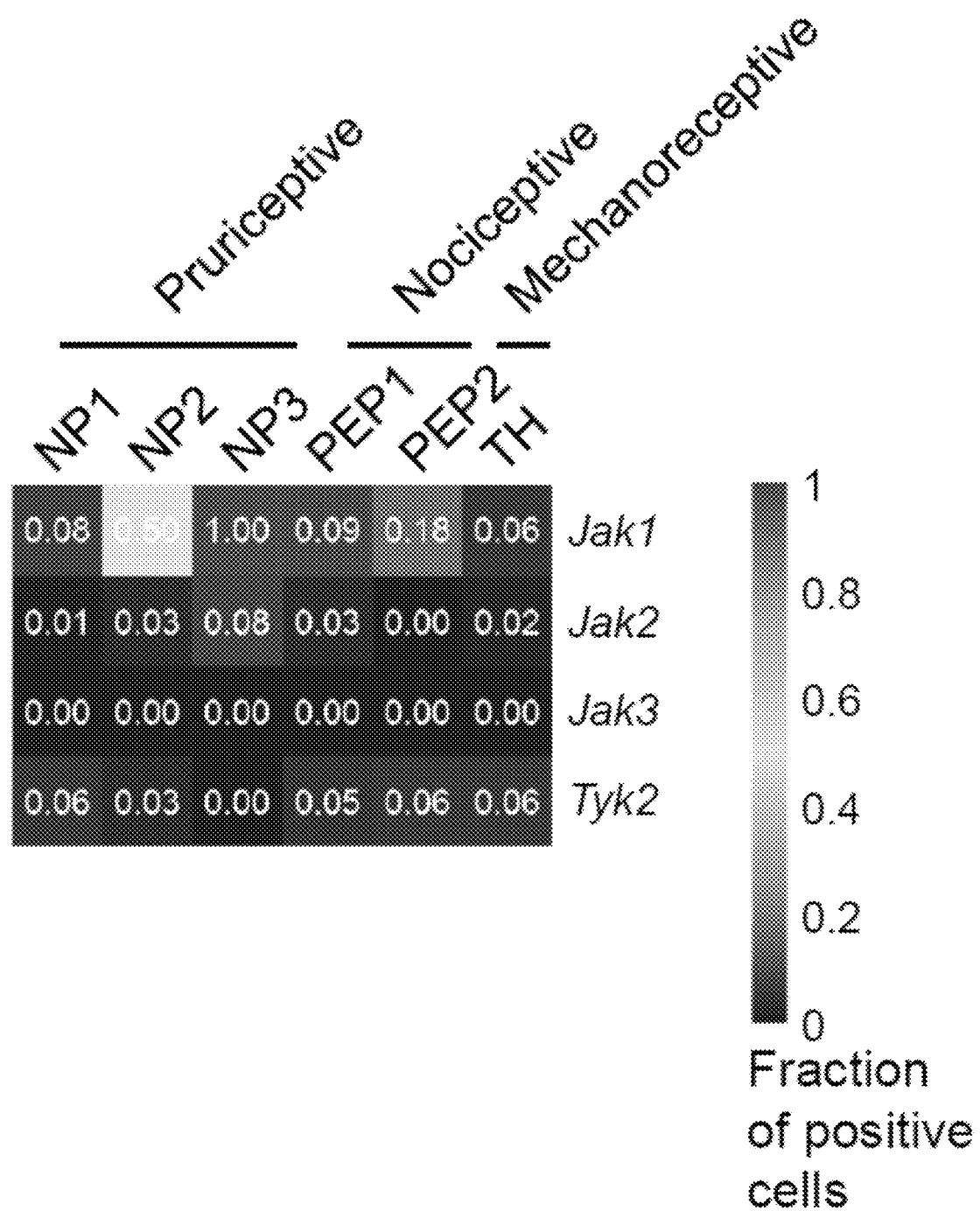
FIG. 15 shows predicted itch-sensory neurons express JAK signaling components. Relates to FIG. 9. Expression profile within mouse DRG neurons at the single cell level of the JAK family of proteins for predicted sensory modalities. Numbers in heat map indicate fraction of positive cells by thresholding method. Full dataset and methods available in Usoskin et al., 2015.

To investigate whether sensory neuron-specific JAK signaling is necessary for elicitation of chronic itch, we generated mice in which JAK1 is conditionally deleted in sensory neurons ($Na_v1.8$-$Cre^+$ $JAK1^{fl/fl}$, $JAK1^{\Delta neuron}$) given the robust expression of JAK1 in pruriceptive neurons (see e.g., FIG. 15). Upon induction of AD-like itch (see e.g., FIG. 9K), $JAK1^{\Delta neuron}$ mice exhibited a marked reduction in chronic itch (see e.g., FIG. 9L) even in the presence of robust skin inflammation (see e.g., FIG. 9M-O). Taken together, these studies demonstrate that neuronal JAK1 is critically important for the elicitation of chronic itch. As such, JAK1 is shown to be a therapeutically relevant target chronic itch disorders that presents in the presence of an inflammatory etiology.

Example 7: Chronic Idiopathic Pruritus (CIP) Patients Exhibit Severe Itch and Neuronal Dysregulation in the Absence of Overt Skin Inflammation Given the strong link between skin inflammation and itch in the setting of AD, we sought to study another itch disorder, chronic idiopathic pruritus (CIP), which presents in the absence of overt skin inflammation to broaden our understanding of chronic itch. CIP is strongly associated with aging and believed to be a manifestation of systemic immune senescence (Norman, 2003; Patel and Yosipovitch, 2010; Reich et al., 2011). As a result, it has been proposed that CIP patients exhibit a type 2 immune profile due to loss of type 1 immunity (Berger and Steinhoff, 2011). In support of this, we recently showed that CIP patients exhibit features of systemic type 2 inflammation associated with low-grade peripheral eosinophilia and elevation of IgE (Xu et al., 2016). Though successful elimination of skin inflammation in AD is known to eliminate symptoms of itch, patients with CIP are often refractory to anti-inflammatory agents.

Figures 10A, 10B, 10C, 10D, 10E, 10F:
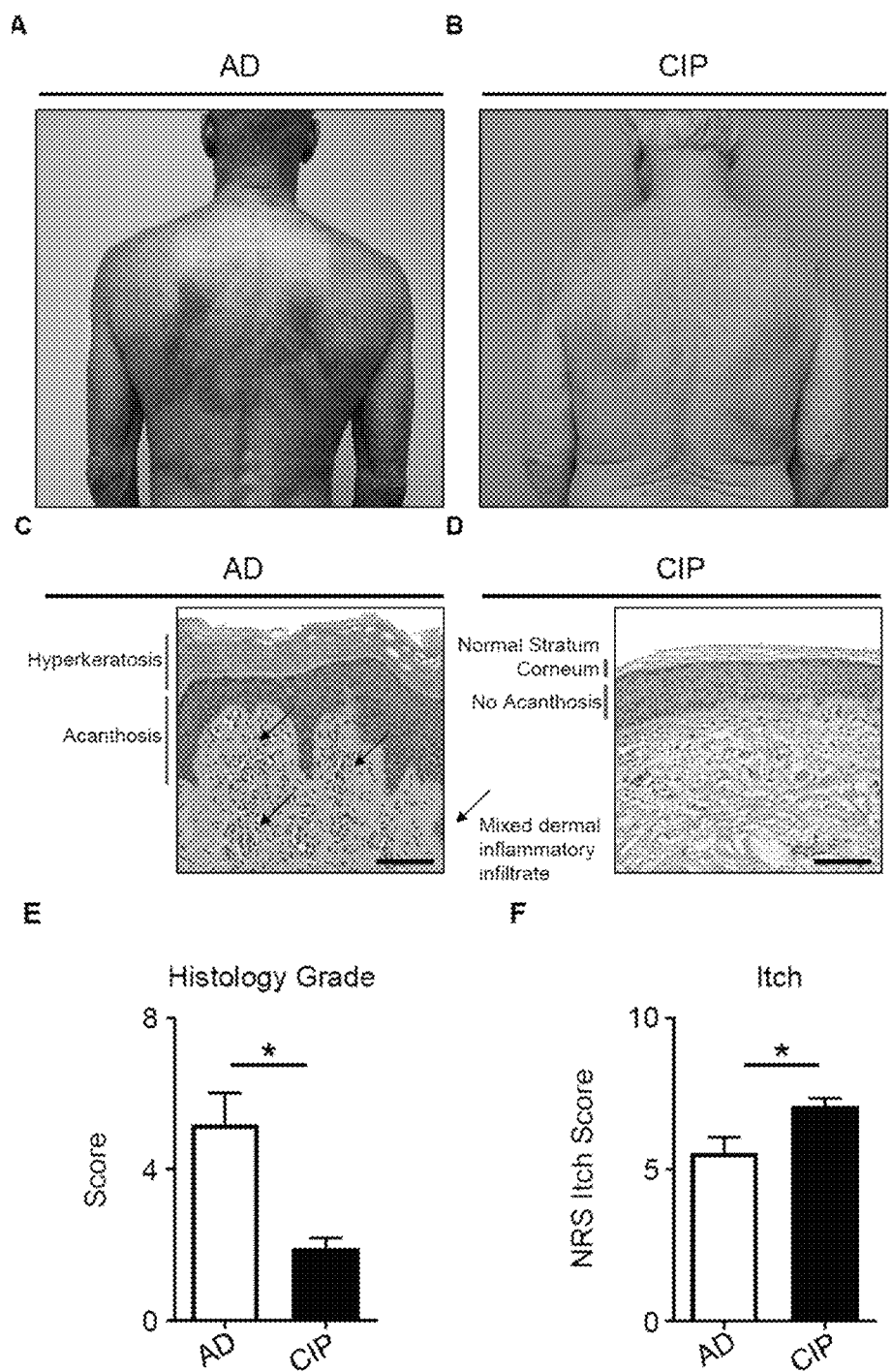
FIG. 10A-FIG. 10H shows CIP is a distinct chronic itch disorder that exhibits neuronal dysregulation and severe itch despite minimal skin inflammation.

Unlike AD, a characteristic inflammatory skin disease (see e.g., FIG. 10A), CIP presents with grossly normal skin findings (see e.g., FIG. 10B). Further, AD histopathology demonstrates clear features of skin inflammation including hyperkeratosis, acanthosis, and a robust mixed dermal inflammatory infiltrate (see e.g., FIG. 10C). However, histopathology of CIP patients exhibits only minimal inflammation upon biopsy from even the most pruritic cutaneous sites, as evidenced by a normal epidermis (no acanthosis) with an overlying healthy "basket weave-patterned" stratum corneum (no hyperkeratosis) (see e.g., FIG. 10D). Indeed, histologic grading of patient biopsies confirmed that CIP patients exhibit markedly lower levels of skin inflammation compared to AD patients (see e.g., FIG. 10E). Remarkably, despite much milder skin inflammation, CIP patients exhibit a higher Numerical Rating Scale (NRS) itch score compared to AD patients (AD NRS itch score: 5.55±0.51, CIP NRS itch score: 7.07±0.26) (see e.g., FIG. 10F). Taken together, these findings demonstrate that despite reduced skin inflammation in comparison to AD patients, CIP patients have more debilitating symptoms of itch. Thus, these findings show that chronic itch can manifest both in the setting of robust skin inflammation as well as in the absence of notable inflammatory processes.

Figure 10G:
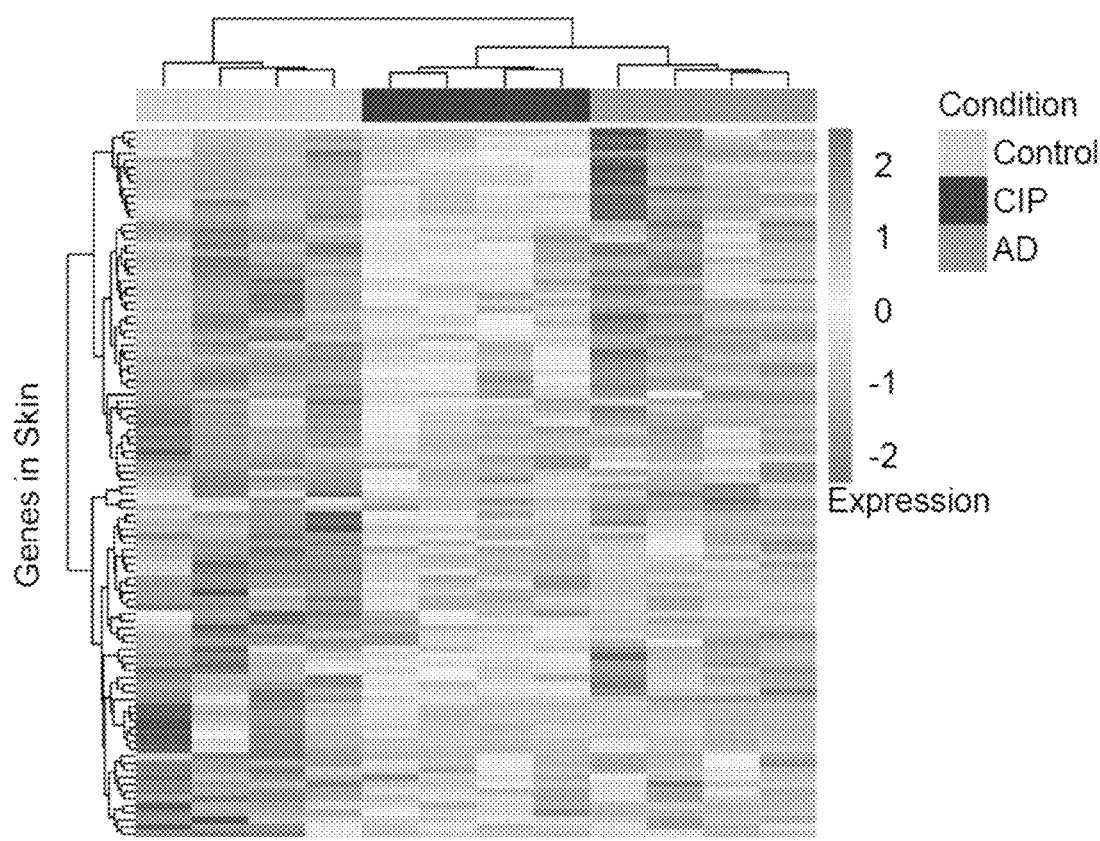
Figure 10H:
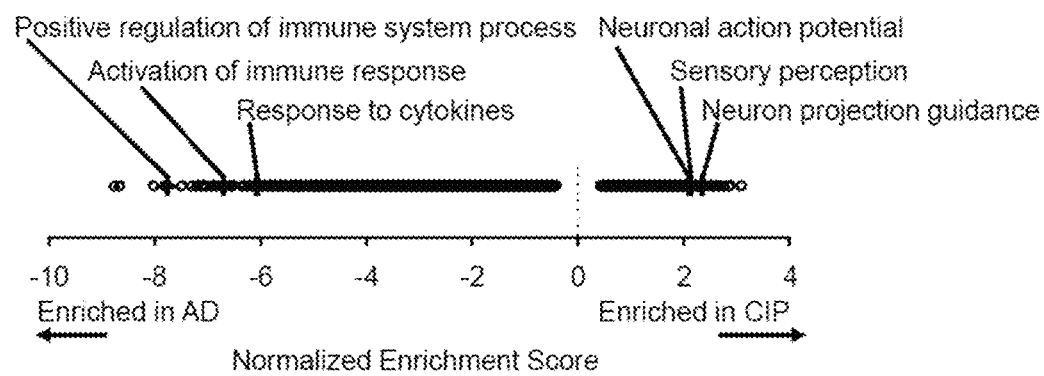

To characterize CIP at the molecular level, we performed RNA-sequencing on skin from four CIP patients, on lesional skin from four AD patients, and on healthy skin from four control subjects. Clustering of each group by expression of the top 100 most differentially expressed genes between control and AD skin revealed that CIP skin is more closely related to AD skin than control skin (see e.g., FIG. 10G). These findings suggest that CIP exhibits molecular signatures that are shared with AD despite marked differences in terms of skin inflammation. However, gene set enrichment analysis (GSEA) (Subramanian et al., 2005) comparing CIP and AD skin revealed specific transcriptional programs that distinguish CIP from AD. This analysis showed that AD skin is associated with broad activation of immune responses (see e.g., FIG. 10H, TABLE 3) and that CIP skin is associated with dysregulation of neuronal processes and sensory perception (see e.g., FIG. 10H, TABLE 4). Collectively, these data demonstrate that, in contrast to the marked proinflammatory signature of AD, CIP is a primary itch condition characterized predominantly by a profile of neuronal dysfunction in association with minimal inflammation. As such, JAK1 is shown to be a therapeutically relevant target chronic itch disorders that presents in the absence of an inflammatory etiology or minimal inflammatory etiology.

TABLE 3

AD skin demonstrates enrichment of immune activation pathways. Relates to FIG. 10. List of top 50 biological process GO terms enriched in AD in a direct comparison of CIP and AD as determined by gene set enrichment analysis (GSEA). Normalized enrichment score (NES) and false discovery rate (FDR) q-value of individual GO terms are provided.

| GO Accession Number | Name | NES | FDR q-value |
|---|---|---|---|
| GO:0002682 | regulation of immune system process | −8.77036 | $<10^{-5}$ |
| GO:0002376 | immune system process | −8.66961 | $<10^{-5}$ |
| GO:0080134 | regulation of response to stress | −8.02582 | $<10^{-5}$ |
| GO:0050776 | regulation of immune response | −7.8129 | $<10^{-5}$ |
| GO:0022613 | ribonucleoprotein complex biogenesis | −7.7964 | $<10^{-5}$ |
| GO:0002684 | positive regulation of immune system process | −7.77017 | $<10^{-5}$ |
| GO:0006952 | defense response | −7.49978 | $<10^{-5}$ |
| GO:0044403 | symbiosis, encompassing mutualism through parasitism | −7.30644 | $<10^{-5}$ |
| GO:0050778 | positive regulation of immune response | −7.20636 | $<10^{-5}$ |
| GO:0044419 | interspecies interaction between organisms | −7.18966 | $<10^{-5}$ |
| GO:0042254 | ribosome biogenesis | −7.11062 | $<10^{-5}$ |
| GO:0031347 | regulation of defense response | −7.10497 | $<10^{-5}$ |
| GO:0048584 | positive, regulation of response to stimulus | −7.05507 | $<10^{-5}$ |
| GO:0006396 | RNA processing | −7.04048 | $<10^{-5}$ |
| GO:0009607 | response to biotic stimulus | −6.93027 | $<10^{-5}$ |
| GO:0043604 | amide biosynthetic process | −6.89239 | $<10^{-5}$ |
| GO:0034660 | ncRNA metabolic process | −6.8318 | $<10^{-5}$ |
| GO:0006955 | immune response | −6.73395 | $<10^{-5}$ |
| GO:0002253 | activation of immune response | −6.70878 | $<10^{-5}$ |

TABLE 3-continued

AD skin demonstrates enrichment of immune activation pathways. Relates to FIG. 10. List of top 50 biological process GO terms enriched in AD in a direct comparison of CIP and AD as determined by gene set enrichment analysis (GSEA). Normalized enrichment score (NES) and false discovery rate (FDR) q-value of individual GO terms are provided.

| GO Accession Number | Name | NES | FDR q-value |
|---|---|---|---|
| GO:0006518 | peptide metabolic process | −6.6791 | $<10^{-5}$ |
| GO:0016072 | rRNA metabolic process | −6.56767 | $<10^{-5}$ |
| GO:1901564 | organonitrogen compound metabolic process | −6.55732 | $<10^{-5}$ |
| GO:0019058 | viral life cycle | −6.53858 | $<10^{-5}$ |
| GO:0031349 | positive regulation of defense response | −6.52802 | $<10^{-5}$ |
| GO:0034470 | ncRNA processing | −6.35599 | $<10^{-5}$ |
| GO:1901566 | organonitrogen compound biosynthetic process | −6.31783 | $<10^{-5}$ |
| GO:0043603 | cellular amide metabolic process | −6.24033 | $<10^{-5}$ |
| GO:0061024 | membrane organization | −6.19839 | $<10^{-5}$ |
| GO:0032101 | regulation of response to external stimulus | −6.11073 | $<10^{-5}$ |
| GO:0045184 | establishment of protein localization | −6.09473 | $<10^{-5}$ |
| GO:0071310 | cellular response to organic substance | −6.08981 | $<10^{-5}$ |
| GO:0002218 | activation of innate immune response | −6.07281 | $<10^{-5}$ |
| GO:0034097 | response to cytokine | −6.07209 | $<10^{-5}$ |
| GO:0009057 | macromolecule catabolic process | −6.07098 | $<10^{-5}$ |
| GO:0045089 | positive regulation of innate immune response | −6.04607 | $<10^{-5}$ |
| GO:0051649 | establishment of localization in cell | −6.03101 | $<10^{-5}$ |
| GO:0007005 | mitochondrion organization | −6.02195 | $<10^{-5}$ |
| GO:0008104 | protein localization | −6.0172 | $<10^{-5}$ |
| GO:0045088 | regulation of innate immune response | −5.9712 | $<10^{-5}$ |
| GO:0065003 | macromolecular complex assembly | −5.95253 | $<10^{-5}$ |
| GO:0071822 | protein complex subunit organization | −5.90784 | $<10^{-5}$ |
| GO:1902580 | single-organism cellular localization | −5.87975 | $<10^{-5}$ |
| GO:0070727 | cellular macromolecule localization | −5.83766 | $<10^{-5}$ |
| GO:0010941 | regulation of cell death | −5.80849 | $<10^{-5}$ |
| GO:0031399 | regulation of protein modification process | −5.80517 | $<10^{-5}$ |
| GO:0009617 | response to bacterium | −5.7918 | $<10^{-5}$ |
| GO:0006413 | translational initiation | −5.75062 | $<10^{-5}$ |
| GO:0051247 | positive regulation of protein metabolic process | −5.73842 | $<10^{-5}$ |
| GO:0009605 | response to external stimulus | −5.73487 | $<10^{-5}$ |

TABLE 4

CIP skin demonstrates enrichment of transcriptional programs associated with neuronal processes and sensory perception. Relates to FIG. 10. List of top 50 biological process GO terms enriched in CIP in a direct comparison of CIP and AD as determined by gene set enrichment analysis (GSEA). Normalized enrichment score (NES) and false discovery rate (FDR) q-value of individual GO terms are provided.

| GO Accession Number | Name | NES | FDR q-value |
|---|---|---|---|
| GO:0032990 | cell part morphogenesis | 3.093461 | 0.002029 |
| GO:0044782 | cilium organization | 2.879501 | 0.002522 |
| GO:0060271 | cilium morphogenesis | 2.867324 | 0.002018 |
| GO:0008589 | regulation of smoothened signaling pathway | 2.766102 | 0.003024 |
| GO:0016054 | organic acid catabolic process | 2.669138 | 0.006637 |
| GO:0046395 | carboxylic acid catabolic process | 2.666201 | 0.005615 |
| GO:0051965 | positive regulation of synapse assembly | 2.584534 | 0.010122 |
| GO:0016339 | calcium-dependent cell-cell adhesion via plasma membrane cell adhesion molecules | 2.545489 | 0.011865 |
| GO:0033539 | fatty acid beta-oxidation using acyl-CoA dehydrogenase | 2.528827 | 0.012158 |
| GO:0010927 | cellular component assembly involved in morphogenesis | 2.521315 | 0.011644 |
| GO:0048667 | cell morphogenesis involved in neuron differentiation | 2.399559 | 0.028197 |
| GO:0072329 | monocarboxylic acid catabolic process | 2.391039 | 0.027353 |
| GO:0007156 | homophilic cell adhesion via plasma membrane adhesion molecules | 2.374797 | 0.027991 |
| GO:0097485 | neuron projection guidance | 2.356602 | 0.029745 |
| GO:0098742 | cell-cell adhesion via plasma-membrane adhesion molecules | 2.32599 | 0.035653 |
| GO:0051298 | centrosome duplication | 2.27191 | 0.048845 |
| GO:0009062 | fatty acid catabolic process | 2.266665 | 0.047421 |
| GO:0061512 | protein localization to cilium | 2.250689 | 0.050193 |
| GO:0030030 | cell projection organization | 2.228846 | 0.055343 |
| GO:0003002 | regionalization | 2.225651 | 0.053408 |
| GO:0050807 | regulation of synapse organization | 2.176872 | 0.069665 |
| GO:0007224 | smoothened signaling pathway | 2.16341 | 0.072499 |
| GO:0048812 | neuron projection morphogenesis | 2.149574 | 0.076482 |
| GO:0019228 | neuronal action potential | 2.135246 | 0.080783 |
| GO:0071236 | cellular response to antibiotic | 2.118108 | 0.08638 |
| GO:0021915 | neural tube development | 2.111597 | 0.086502 |
| GO:0021522 | spinal cord motor neuron differentiation | 2.103877 | 0.087523 |
| GO:0007600 | sensory perception | 2.094911 | 0.089596 |
| GO:0007389 | pattern specification process | 2.093567 | 0.087319 |
| GO:0050953 | sensory perception of light stimulus | 2.082521 | 0.090076 |
| GO:0021510 | spinal cord development | 2.050129 | 0.106422 |
| GO:0000732 | strand displacement | 2.047653 | 0.104586 |
| GO:0045494 | photoreceptor cell maintenance | 2.045306 | 0.103041 |
| GO:0032989 | cellular component molphogenesis | 2.042259 | 0.10153 |
| GO:0021515 | cell differentiation in spinal cord | 2.028853 | 0.107171 |
| GO:0019748 | secondary metabolic process | 2.026103 | 0.10577 |
| GO:1903825 | organic acid transmembrane transport | 2.017675 | 0.108687 |
| GO:0035058 | nonmotile primary cilium assembly | 2.012586 | 0.108942 |
| GO:0060401 | cytosolic calcium ion transport | 1.995952 | 0.117028 |
| GO:0097553 | calcium ion transmembrane import into cytosol | 1.986171 | 0.121127 |
| GO:0031023 | microtubule organizing center organization | 1.977455 | 0.124149 |
| GO:0007517 | muscle organ development | 1.97117 | 0.125907 |
| GO:1902656 | calcium ion import into cytosol | 1.96663 | 0.123353 |
| GO:0007098 | centrosome cycle | 1.96972 | 0.121292 |
| GO:0086010 | membrane depolarization during action potential | 1.964156 | 0.122664 |
| GO:0098534 | centriole assembly | 1.960917 | 0.122407 |
| GO:0070509 | calcium ion import | 1.959427 | 0.121073 |
| GO:0009953 | dorsal/ventral pattern formation | 1.955245 | 0.121612 |
| GO:0097237 | cellular response to toxic substance | 1.954725 | 0.119552 |

Example 8: JAK Inhibition Improves Pruritus in Patients with CIP

Recent proof-of-concept pilot studies and Phase II clinical trials in patients with atopic dermatitis (AD) have demonstrated rapid and significant reduction of itch symptoms in response to treatment with the commercially available JAK inhibitor tofacitinib (Bissonnette et al., 2016; Levy et al., 2015). Whereas these studies sought to investigate JAK inhibition as an anti-inflammatory treatment for AD, our preclinical findings that both pharmacologic JAK inhibition (see e.g., FIG. 9A-J) and lineage-specific neuronal JAK1 deletion (see e.g., FIG. 9K-O) limit itch suggest that JAK inhibition represents a novel neuromodulatory approach to selectively target itch. Therefore, despite the absence of overt skin inflammation in CIP, we hypothesized that CIP patients may benefit from JAK blockade.

Figures 11A, 11B:
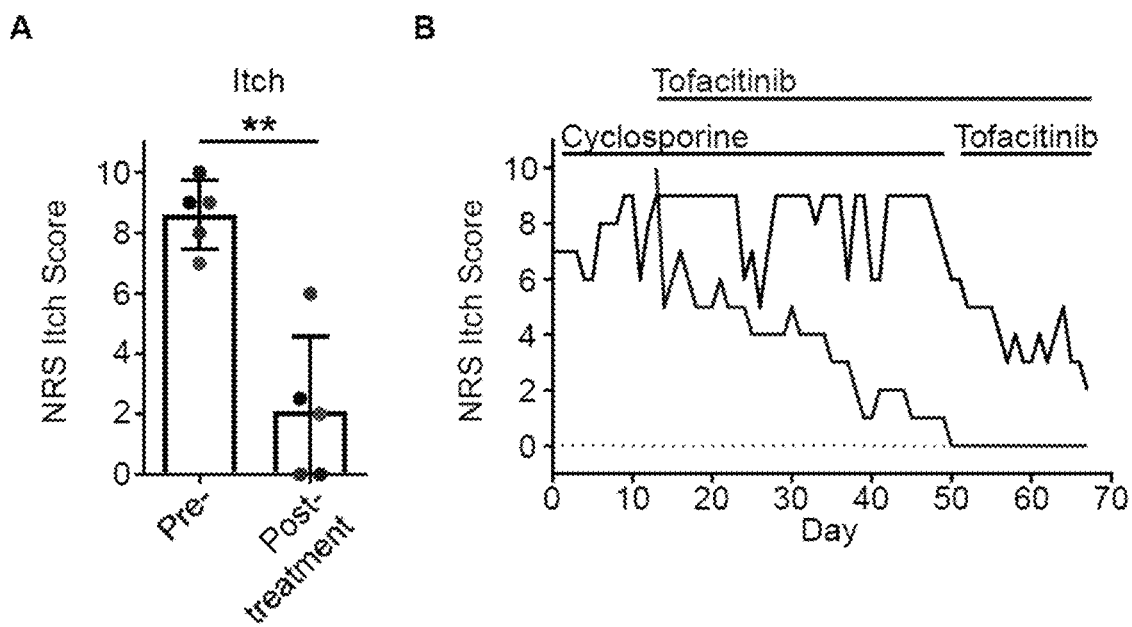
FIG. 11A-FIG. 11B shows patients with refractory CIP improve when treated with JAK inhibitors.

Due to the lack of FDA-approved therapeutics specifically for the indication of CIP, we prescribed off-label treatment with the JAK inhibitor tofacitinib to five patients with severe CIP. All of these patients had previously failed multiple other off-label treatments including potent immunosuppression (TABLE 5). However, one month following treatment with oral tofacitinib, all five patients demonstrated marked improvement in their NRS itch scores (see e.g., FIG. 11A). Strikingly, patients reported rapid onset of itch relief with JAK blockade despite previous immunosuppressive therapy (see e.g., FIG. 11B). Thus, these findings suggest that JAK inhibition may represent a novel therapeutic strategy for patients with chronic itch disorders that are resistant to conventional anti-inflammatory agents alone. Taken together, our studies reveal that classical immune signaling pathways function in the sensory nervous system to mediate chronic itch. Although there are currently no FDA-approved treatments specifically for chronic itch, our discovery of the significance of these immune signaling pathways in the sensory nervous system may promote the development of new therapies that target these shared pathways.

cytokines, elicit itch remain poorly understood. As described herein, three conceptual advances that broaden our understanding of chronic itch were provided. First, it was demonstrated that the classical immune signaling molecules IL-4 and IL-13 directly activate itch-sensory neurons and that sensory neuron-specific deletion of IL-4Rα is sufficient to abate chronic itch in vivo. Second, we show that sensory neuron-specific deletion of JAK1, a key downstream signaling molecule for type 2 cytokines in immune cells, reduces chronic itch. Third, we demonstrate that, regardless of the level of skin inflammation, pharmacologic JAK inhibition is sufficient to abate itch. Importantly, we show that patients with even idiopathic forms of chronic itch who are recalcitrant to standard immunosuppressive therapy improve on systemic JAK inhibitors. Taken together, the current study identifies novel functions of classical immune signaling pathways that regulate sensory perception.

Classically, the dominant source of type 2 cytokines in AD lesional skin was believed to be the adaptive immune system via T helper type 2 (Th2) cells (Weidinger and Novak, 2016). Further, recent studies have shown that Th2 cell-derived IL-31 can elicit scratching in vivo (Cevikbas et al., 2014; Dillon et al., 2004; Sonkoly et al., 2006). Thus, both AD-associated inflammation and itch were largely believed to be mediated by the adaptive immune system. However, we and others have recently shown that innate immune cell populations such as group 2 innate lymphoid cells (ILC2s) and basophils critically mediate skin inflammation independently of the adaptive immune system (Imai et al., 2013; Kim et al., 2013a, 2014; Roediger et al., 2013;

TABLE 5

Characteristics of CIP patients treated with tofacitinib. Relates to FIG. 11. Demographics and relevant medical history including previously failed treatments of CIP patients given tofacitinib.

| | | | | | | | Previously failed treatments | | | | |
|---|---|---|---|---|---|---|---|---|---|---|---|
| Patient | Age | Sex | History of AD | History of malignancy | Topical steroids | Oral steroids | Additional Immuno-suppression[a] | Gaba-pentin | Anti-histamines | Anti-depressents | Photo-therapy |
| 1 | 79 | M | None | None | Yes | Yes | Yes | Yes | Yes | Yes | N/A |
| 2 | 50 | F | None | None | Yes | Yes | N/A | N/A | Yes | N/A | N/A |
| 3 | 60 | M | None | None | Yes | Yes | N/A | N/A | Yes | N/A | Yes |
| 4 | 79 | M | None | Yes | Yes | Yes | Yes | Yes | N/A | Yes | N/A |
| 5 | 75 | F | None | Yes | Yes | Yes | N/A | N/A | N/A | N/A | Yes |

Discussion

Chronic itch is a common example of pathologic dysregulation of sensory responses that are normally employed by mammals to remove invading pathogens. It is a highly debilitating symptom of multiple dermatologic, neurologic, and systemic medical conditions. Moreover, chronic itch can also present in the absence of a clearly defined disorder as in CIP (Berger and Steinhoff, 2011; Mollanazar et al., 2016; Xu et al., 2016; Yosipovitch and Bernhard, 2013). Although itch is an often overlooked symptom in patient care, clinical studies have established that chronic itch has a profoundly negative impact on quality of life (Kini S P et al., 2011; Matterne et al., 2011; Ständer et al., 2007; Yosipovitch and Bernhard, 2013). However, despite its substantial burden on society, there are currently no specific treatments indicated for chronic itch.

In the setting of AD, the type 2 cytokines IL-4, IL-5, and IL-13 coordinate a complex inflammatory response that is critical for disease pathogenesis. This inflammatory cascade leads to debilitating chronic itch. However, the mechanisms by which proinflammatory mediators, such as the type 2 Salimi et al., 2013). In support of this, multiple studies have demonstrated that both ILC2s and basophils are critical sources of type 2 cytokines in vivo (Imai et al., 2013; Kim et al., 2013a, 2014; Roediger et al., 2013; Salimi et al., 2013). Based on our new data demonstrating that neuronal IL-4/13 signaling critically mediates chronic itch, we speculate that, in addition to adaptive Th2 cells, innate immune cells such as ILC2s and basophils play critical roles in mediating itch. Future studies will be performed to fully define the functional contributions of both adaptive and innate immune cells to the development of chronic itch.

Upstream of the type 2 cytokine-associated immune response, the predominately epithelial cell-derived cytokines thymic stromal lymphopoietin (TSLP) and IL-33 have been shown to be master initiators of type 2 inflammation via their effects on a variety of cells including Th2 cells as well as ILC2s and basophils (Hammad and Lambrecht, 2015; Kim and Artis, 2015; Kim et al., 2013b; Oetjen et al., 2016; Siracusa et al., 2013a). Strikingly, two recent studies have demonstrated that TSLP and IL-33 can act directly on sensory neurons and function as pruritogens (Liu et al., 2016; Wilson et al., 2013). Indeed, we and others have shown that TSLP and IL-33 are highly expressed in the setting of MC903-induced AD-like disease (Kim et al., 2013a; Li et al., 2006, 2009; Salimi et al., 2013). Despite high expression of these cytokines and robust activation of numerous downstream cytokine pathways in AD, our study identifies that sensory neuron-specific deletion of IL-4Rα alone is sufficient to abate itch. Thus, it appears that neuronal IL-4Rα signaling is an exquisitely robust target for AD-associated itch. However, whether IL-4Rα represents a novel itch-sensory pathway or modulates the responsiveness of sensory neurons to previously identified pruritogens such as IL-31, TSLP, and IL-33 remains to be determined.

In addition to transmission of itch sensation, the marked reduction of disease severity in IL-4Rα$^{\Delta neuron}$ mice provokes the hypothesis that neuronal activation by type 2 cytokines may also mediate neurogenic inflammation. Strikingly, clinical reports have described improvements in both AD and psoriasis lesions after denervation of the lesional skin, suggesting neurogenic components of both diseases (Amon and Wolff, 1994; Azimi et al., 2015; Raychaudhuri and Farber, 1993). In support of this possibility, recent studies have shown that sensory neurons in the skin can promote Th17-associated inflammation and psoriasis (Kashem et al., 2015; Riol-Blanco et al., 2014). Whether neurogenic processes can regulate type 2 inflammation in the skin remains to be definitively determined. In the lung, Talbot et al. have recently shown that the type 2 cytokine IL-5 stimulates neurons projecting from the nodose ganglia to mediate allergic airway inflammation via release of vasoactive intestinal peptide (VIP) (Talbot et al., 2015). However, we were not able to find evidence that IL-5 activates sensory neurons that innervate the skin. Thus, the mechanisms and functional consequences of sensory neuron activation by type 2 inflammation may be tissue-specific. Future studies will be required to determine what paradigms apply in the skin and the molecular mechanisms that underlie neurogenic type 2 skin inflammation.

Phase II and III clinical trials for dupilumab, an anti-IL-4Rα monoclonal antibody, have repeatedly demonstrated remarkable improvement in itch symptoms in patients (Beck et al., 2014; Simpson et al., 2016; Thaçi et al., 2016). Further, early clinical studies employing JAK inhibitors have demonstrated significant improvement of itch in patients with AD (Bissonnette et al., 2016; Levy et al., 2015). Until now, these changes have been ascribed to the anti-inflammatory properties of IL-4Rα and JAK blockade. However, our study suggests that such improvements of itch symptoms may occur independently of specific anti-inflammatory properties of these therapies and rather be attributable to their previously unrecognized neuromodulatory effects. Based on the potent neuromodulatory effects of JAK inhibition and conditional genetic deletion in mice, we hypothesized that JAK inhibition would work as an anti-itch therapy even in the absence of robust skin inflammation. In support of this, we found that patients with CIP, which presents without overt skin inflammation, improved significantly when treated with tofacitinib. Taken together, these findings suggest that JAK inhibition can serve dual anti-inflammatory and neuromodulatory roles. Importantly, our current studies have allowed us to design a prospective clinical trial exploring the use of a novel JAK1-selective inhibitor (INCB039110) in patients with CIP (clinicaltrials.gov ID: NCT02909569). However, larger prospective randomized-controlled trials will be required to fully determine the efficacy of such treatments.

Immunity at epithelial barrier surfaces is believed to have evolved to mediate rapid expulsion of pathogens as well as potential toxins. Whereas the epithelium was previously thought to be solely a physical barrier, recent advances have highlighted its direct role in a variety of immune functions (Artis and Spits, 2015; Hammad and Lambrecht, 2015; Palm et al., 2012). In addition to the immune system and the epithelial barrier itself, the mammalian host also employs behavioral responses such as coughing and scratching to mechanically remove noxious stimuli prior to tissue damage. Our current study demonstrates that classical immune mediators play an essential part in the sensory circuit to modulate host behavior. By identifying previously unrecognized neuroimmunologic pathways, we have uncovered novel therapeutic approaches for the treatment of pathologic sensory disorders such as chronic itch.

Example 9: Methods

The following example describes the methods used in the previous Examples 2-8 unless expressed otherwise.

Mice

All mice were housed in standard environmental conditions (12 hour light-dark cycle; 23° C.; food and water ad libitum) at Washington University School of Medicine. C57Bl/6 and Rosa26-tdTomato mice were purchased from The Jackson Laboratory. Na$_v$1.8-Cre mice were provided by Dr. Rohini Kuner (Heidelberg University). IL-4-eGFP (4get) mice were provided by Dr. Edward Pearce (MPI-IE). Il4ra$^{flox}$ mice were provided by Dr. Ajay Chawla (UCSF). JAK1$^{flox}$ mice were purchased from Nanjing Biomedical Research Institute of Nanjing University. Na$_v$1.8-tdTomato$^+$ IL-4-eGFP$^+$ reporter mice were generated by first crossing Na$_v$1.8-Cre$^+$ and Rosa26-tdTomato$^+$ mice and then crossing the progeny to the IL-4-eGFP$^+$ mice. IL-4Rα$^{\Delta neuron}$ (Na$_v$1.8-Cre$^+$ Il4ra$^{fl/fl}$) mice were generated by crossing the Na$_v$1.8-Cre$^+$ and Il4ra$^{flox}$ mice. JAK1$^{\Delta neuron}$ (Na$_v$1.8-Cre$^+$ JAK1$^{fl/fl}$) mice were generated by crossing the Na$_v$1.8-Cre$^+$ and Jak1$^{flox}$ mice. Genotyping of mice was performed using standard PCR. All murine work was performed in accordance with the guidelines of the Washington University School of Medicine Department of Comparative Medicine Animal Care and Use Committee (Protocol #20140170).

RNA Isolation from Murine DRG and TG and RT-qPCR

For RNA isolation, murine dorsal root ganglia (DRG) or trigeminal ganglia (TG) were harvested, cleaned of connective tissues, and homogenized in 1 mL Trizol Reagent (Life Technologies). Total RNA was extracted with the RNeasy Mini Kit (Qiagen) following the manufacturer's instructions. Following extraction, samples were treated with DNase (Turbo DNA-Free Kit, Thermo Scientific) following the manufacturer's instructions. Next, cDNA was synthesized using the High-Capacity cDNA Reverse Transcription Kit (Applied Biosystems). Gene expression levels were determined by RT-qPCR (StepOnePlus; Applied Biosystems). Briefly, gene expression was normalized to Gapdh and relative expression was calculated using either the $\Delta C_t$ or $\Delta\Delta C_t$ method where appropriate. For gel electrophoresis, products from RT-qPCR reactions were loaded onto a 2% agarose gel with ethidium bromide (1 µg/mL) and run at 140 V for 25 minutes. Primer and probe sequences used for each gene were selected from pre-validated PrimeTime qPCR Assays (Integrated DNA Technologies). Primer and probe sequences used were:

1. Gapdh -
Probe:
(SEQ ID NO: 1)
/56-FAM/TGCAAATGG/ZEN/CAGCCCTGGTG/3IABkFQ/

Primer 1:
(SEQ ID NO: 2)
GTGGAGTCATACTGGAACATGTAG

Primer 2:
(SEQ ID NO: 3)
AATGGTGAAGGTCGGTGTG

2. Il4ra -
Probe:
(SEQ ID NO: 4)
/56-FAM/CAGAACCAG/ZEN/CAAGCACGCAGA/3IABkFQ/

Primer 1:
(SEQ ID NO: 5)
GTTACAGGAACAAGACCAGCA

Primer 2:
(SEQ ID NO: 6)
TGGAGCCTGAACTCGCA

3. Il5ra -
Probe:
(SEQ ID NO: 7)
/56-FAM/TGAGCAAGC/ZEN/TTCTCCCACTGAGC/3IABkFQ/

Primer 1:
(SEQ ID NO: 8)
AGAATTAGTAACACAGGCACCA

Primer 2:
(SEQ ID NO: 9)
CAAGGATCTAACCAGGGTCTTC

4. Il13ra1 -
Probe:
(SEQ ID NO: 10)
/56-FAM/ACAGGTGGC/ZEN/TGAACTTCTGTGGC/3IABkFQ/

Primer 1:
(SEQ ID NO: 11)
GAGATTTTCGACAGAGACGCT

Primer 2:
(SEQ ID NO: 12)
CTGTTGGTGCTGCTACTGT

5. Il31ra -
Probe:
(SEQ ID NO: 13)
/56-FAM/TCGTCATCT/ZEN/GAGAGGCCATAAACAACTC/3IABkFQ/

Primer 1:
(SEQ ID NO: 14)
GATCGTCTGCTTCTCTTACACC

Primer 2:
(SEQ ID NO: 15)
TAGTGCCGTTCTGTGATCAG

RNA Isolation from Human DRG and RT-PCR

Human dorsal root ganglia (hDRG) were acquired from de-identified US transplant donors under an IRB-exempt protocol. After hDRG extraction, fat, dura, and connective tissues were removed as previously described (Valtcheva et al., 2016). The hDRG were subsequently stored in RNAlater (Life Technologies) at −80° C. until RNA isolation was performed. For RNA isolation, tissue from one half of one hDRG was homogenized in 1 mL Trizol Reagent (Life Technologies) following the manufacturer's instructions. Following total RNA extraction, genomic DNA was eliminated and cDNA synthesized using the Maxima H Minus First Strand cDNA Synthesis Kit with dsDNase (Thermo Scientific) following the manufacturer's instructions. RT-PCR product was loaded onto a 2% agarose gel with ethidium bromide (1 μg/mL) and run at 100 V for 45 minutes. RT-PCR was performed using the following primer sets:

1. IL4RA -
Primer 1:   GACGTGGTCAGTGCGGATAA   (SEQ ID NO: 16)
Primer 2:   CTGAAATCTGCCGGGTCGTT   (SEQ ID NO: 17)

2. IL5RA -
Primer 1:   CTTGCGGTGCTTGTTAACGG   (SEQ ID NO: 18)
Primer 2:   CGAGTGAACGGGTACGTTTCT  (SEQ ID NO: 19)

3. IL13RA1 -
Primer 1:   CCTACGGAAACTCAGCCACC   (SEQ ID NO: 20)
Primer 2:   CGAGTGAACGGGTACGTTTCT  (SEQ ID NO: 21)

4. IL31RA -
Primer 1:   CACAAGAAAAGCTCGCAGACA  (SEQ ID NO: 22)
Primer 2:   GGTGGTTCAGTTTTCGCTATGTT (SEQ ID NO: 23)

Overnight Murine DRG Neuron Culture

Murine DRG neurons were isolated and cultured using a previously published protocol with slight modification (Malin et al., 2007). Briefly, laminectomies were performed on mice and bilateral DRG were removed. After removal of connective tissues, DRG were transferred to 1 mL $Ca^{2+}$/$Mg^{2+}$-free Hank's Balanced Salt Solution (HBSS) containing 1 μL saturated $NaHCO_3$, 0.35 mg L-cysteine, and 20 U papain (Worthington) and incubated at 37° C. for 20 min. The suspension was centrifuged, and the supernatant was removed and replaced with 1 mL $Ca^{2+}$/$Mg^{2+}$-free HBSS containing 3.75 mg collagenase type II (Worthington) and 7.5 mg dispase (Worthington) and incubated at 37° C. for 20 min. After digestion, neurons were gently triturated, pelleted, and then resuspended in Neurobasal-A medium containing 2% B-27 supplement (Gibco), 100 U/mL penicillin plus 100 μg/mL streptomycin (Sigma), 100 ng/mL nerve growth factor (Sigma), and 10% heat-inactivated FBS (Sigma). Neurons were then plated on a 12 mm glass coverslip pre-coated with poly-L-lysine (Sigma) and laminin (Sigma) and cultured under a humidified atmosphere of 5% $CO_2$ at 37° C. for 18-24 hours before use.

Calcium Imaging

Cultured DRG neurons were loaded with 4 μM Fura-2 AM (Life Technologies) in overnight DRG culture medium at 37° C. for 45 minutes. Cells were then washed three times and incubated in calcium imaging buffer (130 mM NaCl, 3 mM KCl, 2.5 mM $CaCl_2$, 0.6 mM $MgCl_2$, 10 mM HEPES, 10 mM glucose, 1.2 mM $NaHCO_3$, pH 7.45) at room temperature for 30 minutes before use. All recombinant murine cytokines (IL-4, IL-5, and IL-13: Peprotech, IL-31: Bristol-Myers Squibb) were used at 300 nM, while histamine (Sigma) and capsaicin (Sigma) were used at 50 μM and 300 nM, respectively. Only sensory neurons that responded to a final challenge of 100 mM KCl were used in analyses. Fluorescence was recorded at 340 nm and 380 nm excitation wavelengths (F340, F380) using an inverted Nikon Ti-E microscope with NIS-Elements imaging software (Nikon Instruments). Fluorescence ratios (F340/F380) were normalized to baseline and used to reflect changes in intracellular $Ca^{2+}$ and neuronal activation upon stimulation. Cells were considered responsive if they demonstrated a change in fluorescence ratio >10% of baseline. Data were derived from two to three independent experiments.

MC903 Treatment and Pathology Assessment

For induction of AD-like inflammation and itch, mice were topically treated once daily with 2 nmol of MC903 (calcipotriol, Tocris Bioscience) for 7 days or 1 nmol of MC903 for 12 days on both ears in 20 µL of ethanol (vehicle) as previously described (Kim et al., 2013a, 2014, Siracusa et al., 2011, 2013b). Ear thickness measurements were performed daily with dial calipers as previously described (Kim et al., 2013a, 2014). At the end of the MC903 treatment, murine ear skin tissues were fixed in 4% paraformaldehyde (PFA) and embedded in paraffin before sectioning and staining with Hematoxylin & Eosin (H&E). Histology score was determined by the following formula using ImageJ analysis software (NIH) as previously described: (total number of lymphocytes per high power field (HPF)+thickness of the epidermis measured in microns from the basement membrane to the top of the stratum corneum) divided by 100 (Kim et al., 2014). All images were captured with a NanoZoomer 2.0-HT System (Hamamatsu). Murine disease and behavioral assessment data (below) were derived from two to three independent experiments.

Behavioral Assessment

For behavioral assessments, mice were first acclimated to the recording room and behavior chambers at least one day prior to testing. On the day of testing, mice were again acclimated to the recording room and behavior chambers and then video recorded. The video recordings were then manually scored for number of scratching bouts per 30 minute block. One scratching bout was defined as one instance of lifting the hind paw from the floor, scratching, and returning the paw to the floor or placing the paw in the animal's mouth. All behavioral tests were performed on sex- and age-matched adult mice (8-12 weeks old).

Murine and Human Skin RNA Extraction

Samples of murine skin were obtained and stored in RNAlater (Sigma) at −80° C. before processing following the manufacturer's instructions. Human skin tissues were obtained as 4-mm punch biopsies and stored in RNAlater (Sigma) at −80° C. before processing. To extract whole tissue RNA, samples were homogenized using a bead homogenizer and processed using the Qiagen RNeasy kit following the manufacturer's instructions. Following total RNA extraction, samples were treated with DNase (Turbo DNA-Free Kit, Thermo Scientific) following the manufacturer's instructions before sequencing library preparation. All human skin samples for RNA-sequencing analysis were acquired under protocols approved by the Washington University in St. Louis IRB (Protocols #201410014, #201412117, and #201507042).

Library Preparation and RNA-Sequencing

Library preparation, sequence alignment, and determination of transcript abundance were carried out by the Genome Technology Access Center (GTAC) at Washington University School of Medicine. Briefly, library preparation was performed with 1 ug of total RNA, and RNA integrity was determined using an Agilent Bioanalyzer. Ribosomal RNA was removed by a hybridization method using Ribo-ZERO kits (Illumina-EpiCentre). mRNA was then fragmented in buffer containing 40 mM Tris Acetate (pH 8.2), 100 mM Potassium Acetate, and 30 mM Magnesium Acetate and heated to 94° C. for 150 seconds. mRNA was reverse transcribed to yield cDNA using SuperScript III RT enzyme (Life Technologies, per manufacturer's instructions) and random hexamers. A second strand reaction was performed to yield ds-cDNA. cDNA was blunt ended, had an A base added to the 3' ends, and then had Illumina sequencing adapters ligated to the ends. Ligated fragments were then amplified for 12 cycles using primers incorporating unique index tags. Fragments were sequenced on an Illumina HiSeq-3000 using single reads extending 50 bases.

RNA-sequencing reads were aligned to the Ensembl release 76 assembly with STAR version 2.0.4b. Gene counts were derived from the number of uniquely aligned unambiguous reads by Subread:featureCount version 1.4.5. Transcript counts were produced by Sailfish version 0.6.3. Sequencing performance was assessed for total number of aligned reads, total number of uniquely aligned reads, genes and transcripts detected, ribosomal fraction, known junction saturation, and read distribution over known gene models with RSeQC version 2.3.

Differential Gene Expression and Gene Set Enrichment Analysis

Differential gene expression analysis and sample clustering from RNA-sequencing data were performed with the DESeq2 package available in R using default configurations. Genes with a two-fold or greater fold change and an adjusted p-value <0.1 were considered significant. Dendrograms in heat maps were formed by hierarchical clustering on the Euclidean distances between samples. Gene set enrichment analysis (GSEA) was carried out using the preranked gene list feature available in the javaGSEA application available online (http://www.broadinstitute.org/gsea/downloads.jsp). Genes were preranked by the product of the fold change and the inverse of the adjusted p-value of differential expression as determined by DESeq2. Gene sets were derived from the Biological Process Ontology.

Intravital Two-Photon Imaging

Time-lapse imaging was performed with a custom built two-photon microscope equipped with a 1.0 NA 20× water dipping objective (Olympus) running ImageWarp acquisition software (A&B Software) as previously described (Zinselmeyer et al., 2009). In brief, mice were anesthetized and VetBond (3M) was used to attach the ear to a plastic cover glass that was secured to a heated support. Mice were placed on a warming pad and given intraperitoneal (i.p.) saline for hydration for imaging experiments lasting more than 90 minutes. A drop of water was placed on the skin and the ears were imaged directly with the water dipping objective. Video-rate imaging was used to identify sites with $Na_v1.8$-tdTomato$^+$ nerve fibers. IL-4-eGFP$^+$ cell migration dynamics were analyzed using 3D time-lapse imaging for up to 3 hours for each time point. Tissue was imaged with a Chameleon Vision II Ti:Sapphire laser (Coherent) tuned to 915 nm and fluorescence emission detected by PMTs simultaneously using 495 nm and 560 nm dichroic filters: Blue (<495 nm, SHG collagen), green (495-560 nm, eGFP) and red (>560 nm, tdTomato). Autofluorescence of the epidermis appears as mix of color (495-600 nm) and thus can be discriminated from IL-4-eGFP$^+$ cells. For time-lapse imaging, we acquired a 220×240×75 µm volume as 31 sequential 2.5 µm z-steps with a time resolution of approximately 42 seconds. X,Y was resolution 0.75 µm/pixel, which is adequate to resolve individual IL-4-eGFP$^+$ cells and nerve fibers. Multi-dimensional data sets were rendered in 3D using Imaris (Bitplane). Cell tracking and data analysis were performed using Imaris and Motility Lab (2ptrack.net). IL-4-eGFP$^+$ cells were defined as sensory fiber-associated if they overlapped with sensory fibers and the contacts between IL-4-eGFP$^+$ cells and $Na_v1.8$-tdTomato$^+$ nerve fibers were confirmed manually in 3D images.

Pharmacologic JAK Inhibition

Stock ruxolitinib (Selleck Chemicals) solutions were prepared in DMSO (Sigma) per the manufacturer's instructions. For systemic treatments, mice treated twice daily with 100

μg ruxolitinib diluted in 100 μl PBS by intraperitoneal (i.p.) injection. For intrathecal (i.t.) ruxolitinib treatments, mice were injected 24 hours before behavioral assays with 10 μg ruxolitinib diluted in 10 μl PBS. Control mice were injected with appropriate vehicle controls (DMSO in PBS) of equivalent volumes.

Human Histopathology

Human skin tissues were obtained as 4-mm punch biopsy specimens then fixed in 10% paraformaldehyde (PFA) and embedded in paraffin. Sections were stained with H&E. Clinical analyses of patient biopsies were carried out by the Washington University Dermatopathology Center. All samples were collected from fully consented individuals, and human studies were approved by the Washington University in St. Louis IRB (Protocols #201410014 and #201412117). Histology score was determined by the following formula using ImageJ analysis software (NIH) as previously described: (total number of lymphocytes per high power field (HPF)+thickness of the epidermis measured in microns from the basement membrane to the top of the stratum corneum) divided by 100 (Kim et al., 2014).

Numerical Rating Scale (NRS) Itch Scoring

Patients in the specialty Itch Clinic at the Center for Advanced Medicine (CAM) at Washington University School of Medicine are routinely assessed prospectively for their NRS itch score. Briefly, patients were asked to rate their itch intensity over the past 24 hours from 0 to 10 where 0 represents "no itch" and 10 represents the "worst itch imaginable". For AD and CIP patient comparisons, NRS itch scores were obtained by retrospective analysis of charts from patients seen between August 2014 and February 2016. For patients who received treatment with tofacitinib 5 mg by mouth twice daily, NRS itch scores were obtained prospectively from the beginning of treatment. Recordings of daily NRS itch scores of two patients are reported in FIG. 7B during tofacitinib treatment. These analyses were approved by the Washington University in St. Louis IRB (Protocol #201605144).

Statistical Analysis

Data are presented as mean±SEM unless indicated otherwise. Statistical significance was determined by unpaired Student's t-test with Welch's correction unless noted otherwise. Statistical analyses were performed using Prism GraphPad software v7.0. Significance is labeled as: *$p<0.001$, $p<0.01$, *$p<0.05$, N.S., Not Significant.

---

What is claimed is:

1. A method for treating pruritus in a subject in need thereof, the method comprising administering to the subject a therapeutically effective amount of a JAK1 inhibitor.

2. The method of claim 1, wherein the subject is diagnosed with pruritus or chronic idiopathic pruritus and treatment prevents or reduces pruritus in the subject.

3. The method of claim 1, wherein the subject has extremely severe itching or severe itching; or
the subject has moderate or mild itching.

4. The method of claim 1, wherein
the pruritus has lasted for at least at least seven weeks;
the pruritus has lasted for at least at least eight weeks;
the pruritus has lasted for at least at least nine weeks; or
the pruritus has lasted for at least at least ten weeks.

5. The method of claim 1, wherein treatment reduces severity of itching in a subject, increases number of itch-free days in the subject, improves quality of life of the subject, or any combination thereof.

6. The method of claim 1, wherein the subject is predisposed to pruritus or chronic idiopathic pruritus and treatment with the JAK inhibitor prevents a reoccurrence of chronic pruritus in the subject or reduces frequency of acute pruritus in the subject.

7. The method of claim 1, wherein the JAK inhibitor is selected from one or more of the group consisting of: tofacitinib, ruxolitinib, baricitinib, itacitnib (INCB039110), oclacitinib, AZD1480, fedratinib, AT9283, AG-490, momelotinib, TG101209, gandotinib, NVP-BSK805, AZ 960, CEP-33779, Pacritinib, XL019, S-Ruxolitinib, ZM 39923, Decernotinib, Cerdulatinib, filgotinib, FLLL32, BMS-911543, peficitinib, GLPG0634, GLPG0634 analogue, Go6976, curcumol, cucurbitacin, lestaurtinib, upadacitinib, CHZ868, Solcitinib (GSK 2586184), NS-018; or a derivative thereof; or pharmaceutically acceptable salt thereof.

8. The method of claim 1, wherein the JAK inhibitor is

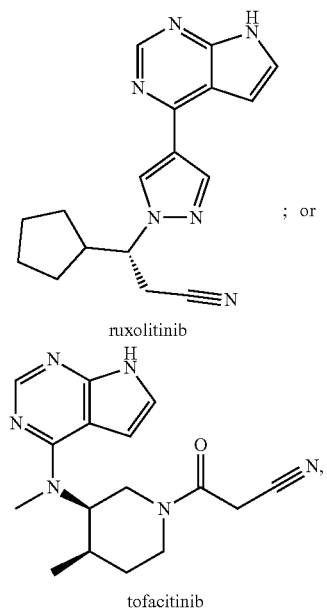

ruxolitinib tofacitinib or a combination thereof.

9. The method of claim 1, where the JAK inhibitor is administered parenterally, intrathecally, intranasally, or orally.

10. The method of claim 1, wherein the JAK inhibitor is administered on a daily basis, administered on a daily basis for at least 7 consecutive days, at least 14 consecutive days, or at least 30 consecutive days.

11. The method of claim 1, wherein the pruritus is a symptom of broad activation of immune responses or dysregulation of neuronal processes and sensory perception.

12. The method of claim 1, wherein the subject is diagnosed with, or the pruritus is a symptom of, a disease or condition selected from one or more of the group consisting of: allergic reaction, arthropod bites, athlete's foot, atopic dermatitis (AD), atopic itch, atopic dermatitis-associated itch, autoimmune connective tissue disease, bacterial infection, biliary itch, broad activation of immune responses, body louse, bullous diseases, brachioradial pruritus, brain tumors, chronic idiopathic pruritus, contact dermatitis, cholestasis, cutaneous larva migrans, cutaneous T-cell lymphoma, nervous system damage, dandruff, delusional parasitosis, dermatomyositis, dermatosis of pregnancy, diabetes mellitus, drug eruptions, dysregulation of neuronal processes and sensory perception, eczema, eosinophilic folliculitis, foreign objects or devices on skin, fungal infection, gestational pemphigoid, head lice, herpes, hidradenitis suppurativa, hives, Hodgkin's disease, hyperparathyroidism, idiopathic chronic itch, inflammation, insect infestation, insect bites, insect stings, intrahepatic cholestasis of pregnancy, iron deficiency anemia, increased accumulation of exogenous opioids or synthetic opioids, internal cancer, jaundice, lichen planus, lichen sclerosus, lupus erythematosus, lymphoma, lymphoma-associated itch, leukemia-associated itch, malignancy, mastocytosis, menopause, multiple sclerosis, neoplasm, nerve irritation, neurogenic itch, neuropathic itch, notalgia paresthetica, notalgia obsessive-compulsive disorders, paresthetica, parasitic infection, papular urtcaria, pediculosis, peripheral neuropathy, photodermatitis, polycythemia vera, psychiatric disease, psychogenic itch, pruritic popular eruption of HIV, pruritic urticarial papules and plaques of pregnancy (PUPPP), psoriasis, psoriasis-associated itch, psoriatic itch, pubic lice, punctate palmoplantar keratoderma, renal itch, rheumatoid arthritis, scabies, scar growth, shaving, seborrheic dermatitis, stasis dermatitis, sunburn, swimmer's itch, systemic immune senescence, tactile hallucinations, Th17-associated inflammation, thyroid illness, uraemia, pruritus or uremic itch, urticaria, urticarial itch, varicella, viral infection, wound or scab healing, and xerosis.

13. The method of claim 1, wherein
the pruritus has an inflammatory etiology;
the pruritus has neuronal dysfunction etiology; or
the pruritus has an unknown etiology.

14. The method of claim 1, wherein the JAK inhibitor is a TRPV1 inhibitor;
modulates signaling of IL-4 or IL-13 pathway; or
targets an IL-4Ra signaling pathway.

15. The method of claim 1, further comprising administration of a TRPV1 inhibitor, dupilumab, or secukinumab.

16. The method of claim 1, wherein the pruritus is chronic idiopathic pruritus.

17. The method of claim 16, wherein the JAK inhibitor is selected from Tofacitinib or Ruxolitinib or a combination thereof.

18. The method of claim 16, wherein the JAK inhibitor is not oclacitinib.

19. A method of treating chronic idiopathic pruritus in a human subject comprising administering to the subject a therapeutically effective amount of a JAK inhibitor selected from the group consisting of Tofacitinib and Ruxolitinib or a combination thereof.

20. The method of claim 1, wherein the pruritus is not associated with atopic dermatitis.

21. The method of claim 1, wherein the pruritus comprises a neurogenic itch component.

* * * * *